US009345677B2

(12) United States Patent
Friedman et al.

(10) Patent No.: US 9,345,677 B2
(45) Date of Patent: *May 24, 2016

(54) COMPOSITIONS, METHODS AND KITS RELATING TO HER-2 CLEAVAGE

(75) Inventors: Steven M. Friedman, West Chester, PA (US); Peggy A. Scherle, Media, PA (US); Xiangdong Liu, Metchuen, NJ (US); Krishna Vaddi, Hockessin, DE (US); Jordan S. Fridman, Newark, DE (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 69 days.

This patent is subject to a terminal disclaimer.

(21) Appl. No.: 13/336,587

(22) Filed: Dec. 23, 2011

(65) Prior Publication Data

US 2012/0263676 A1    Oct. 18, 2012

Related U.S. Application Data

(63) Continuation of application No. 10/817,718, filed on Apr. 2, 2004, now Pat. No. 8,088,737.

(60) Provisional application No. 60/460,678, filed on Apr. 4, 2003, provisional application No. 60/472,494, filed on May 22, 2003, provisional application No. 60/532,030, filed on Dec. 22, 2003, provisional application No. 60/548,986, filed on Mar. 1, 2004.

(51) Int. Cl.
*A61K 31/19*    (2006.01)
*A61K 31/395*    (2006.01)

(52) U.S. Cl.
CPC .............. *A61K 31/19* (2013.01); *A61K 31/395* (2013.01)

(58) Field of Classification Search
CPC ....... A61K 6/00; A61K 31/00; A61K 31/185; A61K 31/19; A61K 31/395; A61K 31/397; A61K 31/40; A61K 31/403; A61K 31/404; A61K 31/41; A61K 31/435; A61K 31/438; A61K 31/44; A61K 31/445; A61K 31/495; A61K 31/55; A61K 39/00; A61K 39/395; A61K 2239/505; C07K 1/00; C07K 16/00; C07K 16/18; C07K 16/28; C07K 16/2851
See application file for complete search history.

(56) References Cited

U.S. PATENT DOCUMENTS

| | | | |
|---|---|---|---|
| 5,023,243 A | 6/1991 | Tullis | |
| 5,168,053 A | 12/1992 | Altman et al. | |
| 5,190,931 A | 3/1993 | Inouye | |
| 5,296,506 A | 3/1994 | Kingston et al. | |
| 5,405,972 A | 4/1995 | Holton et al. | |
| 5,411,984 A | 5/1995 | Kingston et al. | |
| 5,422,364 A | 6/1995 | Nicolaou et al. | |
| 5,440,057 A | 8/1995 | Nicolaou et al. | |
| 5,461,169 A | 10/1995 | Nicolaou et al. | |
| 5,468,769 A | 11/1995 | Klein et al. | |
| 5,475,120 A | 12/1995 | Rao | |
| 5,478,736 A | 12/1995 | Nair | |
| 5,478,854 A | 12/1995 | Farina et al. | |
| 5,484,809 A | 1/1996 | Hostetler et al. | |
| 5,488,116 A | 1/1996 | Danishefsky et al. | |
| 5,489,589 A | 2/1996 | Wittman et al. | |
| 5,508,447 A | 4/1996 | Magnus | |
| 5,527,924 A | 6/1996 | Danishefsky et al. | |
| 5,530,020 A | 6/1996 | Gunawardana et al. | |
| 5,565,478 A | 10/1996 | Kohn et al. | |
| 5,569,729 A | 10/1996 | Leclerc | |
| 5,646,176 A | 7/1997 | Golik et al. | |
| 5,872,152 A | 2/1999 | Brown et al. | |
| 6,004,490 A | 12/1999 | Tsai | |
| 6,270,989 B1 | 8/2001 | Treco et al. | |
| 6,387,371 B1 | 5/2002 | Hudziak et al. | |
| 6,492,422 B2 | 12/2002 | O'Brien et al. | |
| 6,495,565 B2 | 12/2002 | Duan et al. | |
| 6,495,578 B1 | 12/2002 | Watanabe et al. | |
| 6,495,699 B2 | 12/2002 | Bender et al. | |
| 6,500,847 B2 | 12/2002 | VanZandt et al. | |

(Continued)

FOREIGN PATENT DOCUMENTS

| WO | WO 92/07065 | 4/1992 |
|---|---|---|
| WO | WO 94/17810 | 8/1994 |

(Continued)

OTHER PUBLICATIONS

Ali, et al, "Relationship of serum HER2/neu and serum CA 15-3 in patients with metastatic breast cancer," *Clin, Chem.*, 48:1314-1320, (2002).
Amour, et al., "The in vitro activity of ADAM-10 is inhibited by TIMP-1 and TIMP-3," *FEBS Letters*, 473(3):275-279, (2000).
Arribas et al., "Protein ectodomain shedding," *Chem Rev.*, 102(12):4627-4638, (2002).
Azios, et al., "Expression of heratatin, an autoinhibitor of HER-2/neu, inhibits transactivation of HER-3 by HER-2 and blocks EGF activation of the EGF receptor," *Oncogene*, 20:5199-5209, (2001).
Babine, et al., "Molecular Recognition of Proteinminus signLigand Complexes: Applications to Drug Design," *Chem. Rev.*, 97(5):1359-1472, (1997).
Baselga and Albanell, "Mechanism of action of anti-HER2 monoclonal antibodies," *Ann Oncol.*, 12(1):S35-S41, (2001).
Baselga, et al, "Mechanism of action of trastuzumab and scientific update," *Sem. Oncol.*, 28(16):4-11, (2001).

(Continued)

*Primary Examiner* — Alana Harris Dent
(74) *Attorney, Agent, or Firm* — Fish & Richardson P.C.

(57) ABSTRACT

The present invention relates to compositions, methods and kits based on the ADAM-mediated cleavage of Her-2. The present invention also relates to treatments for cancer, and in particular, breast cancer, by modulating the ADAM-mediated cleavage of Her-2. Further, the invention relates to compositions, methods and kits based on the surprising synergistic effect between inhibition of Her-2 cleavage by an ADAM and certain cytostatic (e.g., Herceptin) and cytotoxic (e.g., Taxol) compounds in, among other things, inhibiting tumor cell proliferation and inducing cell death. Additionally, the invention relates to novel variants of ADAM15, designated ADAM15 variant 1 and ADAM15 variant 2, now identified and isolated.

15 Claims, 36 Drawing Sheets

(56) References Cited

U.S. PATENT DOCUMENTS

| | | |
|---|---|---|
| 6,500,948 B1 | 12/2002 | Zook et al. |
| 6,506,764 B1 | 1/2003 | Baxter et al. |
| 6,511,993 B1 | 1/2003 | Dack et al. |
| 6,534,491 B2 | 3/2003 | Levin et al. |
| 6,541,214 B1 | 4/2003 | Clinton |
| 6,541,489 B1 | 4/2003 | Barta et al. |
| 6,541,521 B1 | 4/2003 | Purchase, Jr. et al. |
| 6,541,638 B2 | 4/2003 | Aebi et al. |
| 6,544,980 B2 | 4/2003 | Warshawsky et al. |
| 6,545,038 B1 | 4/2003 | De et al. |
| 6,548,524 B2 | 4/2003 | Levin et al. |
| 6,548,667 B2 | 4/2003 | Park et al. |
| 6,555,535 B2 | 4/2003 | O'Brien et al. |
| 6,559,142 B2 | 5/2003 | O'Brien et al. |
| 6,563,002 B2 | 5/2003 | Lino et al. |
| 6,566,116 B1 | 5/2003 | Koji et al. |
| 6,566,381 B1 | 5/2003 | Cheng et al. |
| 6,569,855 B2 | 5/2003 | Natchus et al. |
| 6,569,899 B1 | 5/2003 | Takahashi et al. |
| 6,576,628 B1 | 6/2003 | Grams et al. |
| 6,579,890 B1 | 6/2003 | Horne et al. |
| 6,579,982 B1 | 6/2003 | Blagg |
| 6,583,299 B1 | 6/2003 | Hockerman et al. |
| 6,605,742 B2 | 8/2003 | Hoyer et al. |
| 6,608,104 B2 | 8/2003 | Noe |
| 6,620,813 B1 | 9/2003 | Wang et al. |
| 6,620,823 B2 | 9/2003 | Maduskuie et al. |
| 6,620,835 B2 | 9/2003 | O'Brien et al. |
| 6,624,144 B1 | 9/2003 | Koivunen et al. |
| 6,624,177 B1 | 9/2003 | O'Brien et al. |
| 6,624,196 B2 | 9/2003 | Purchase, Jr. et al. |
| 6,638,952 B1 | 10/2003 | Li et al. |
| 6,642,255 B2 | 11/2003 | Xue et al. |
| 6,656,448 B1 | 12/2003 | Carpenter, Jr. et al. |
| 6,656,954 B2 | 12/2003 | Bedell et al. |
| 6,660,738 B2 | 12/2003 | Aebi et al. |
| 6,667,316 B1 | 12/2003 | Man et al. |
| 6,667,388 B2 | 12/2003 | Bein et al. |
| 6,677,321 B1 | 1/2004 | Levin |
| 6,677,355 B1 | 1/2004 | Conrad et al. |
| 6,683,060 B2 | 1/2004 | Hsu et al. |
| 6,683,093 B2 | 1/2004 | Barta et al. |
| 6,683,155 B1 | 1/2004 | Silbiger et al. |
| 6,686,348 B2 | 2/2004 | De Nanteuil et al. |
| 6,689,771 B2 | 2/2004 | Duan et al. |
| 6,689,794 B2 | 2/2004 | Freskos et al. |
| 6,696,449 B2 | 2/2004 | Barta et al. |
| 6,696,456 B1 | 2/2004 | Pikul et al. |
| 6,703,379 B2 | 3/2004 | Iino et al. |
| 6,703,415 B2 | 3/2004 | Mobashery et al. |
| 6,706,723 B2 | 3/2004 | Noe et al. |
| 7,723,349 B2 | 5/2010 | Yao et al. |
| 2002/0182702 A1 | 12/2002 | Ruben et al. |
| 2004/0259896 A1 | 12/2004 | Yao et al. |
| 2005/0113344 A1 | 5/2005 | Li et al. |
| 2005/0250789 A1 | 11/2005 | Burns et al. |
| 2007/0117809 A1 | 5/2007 | Fridman |
| 2007/0280943 A1 | 12/2007 | Friedman et al. |

FOREIGN PATENT DOCUMENTS

| | | |
|---|---|---|
| WO | WO 94/23744 | 10/1994 |
| WO | WO00/29609 | 5/2000 |
| WO | WO03/051825 | 6/2003 |
| WO | WO03/106381 | 12/2003 |
| WO | WO2004/096139 | 11/2004 |
| WO | WO2005/037826 | 4/2005 |
| WO | WO2005/117882 | 12/2005 |

OTHER PUBLICATIONS

Baselga, et al., "Phase II Study of weekly intravenous recombinant humanized anti-p185 HER2 monoclonal antibody in patients with HER2/neu-overexpressing metastatic breast cancer," *J. Clinical Oncology*, 14(3):737-744, (1996).

Baselga, et al., "Phase II Study of weekly intravenous recombinant humanized anti-p185 HER2 monoclonal antibody in patients with HER2/neu-overexpressing metastatic breast cancer," *J. Clinical Oncology*, 14:737-744, (1997).

Basu, et al., "Inhibition of tyrosine kinase activity of the epidermal growth factor (EGF) receptor by a truncated receptor form that binds to EGF: role for interreceptor interaction in kinase regulation," *Mol. Cell Biol.*, 9:871-877, (1989).

Brodowicz, et al, "Soluble HER-2/neu neutralizes biologic effects of anti-HER-2/neu antibody on breast cancer cells in vitro," *Int. J. Cancer*, 73:8750879, (1997).

Carney, et al., "Potential clinical utility of serum HER-2/neu oncoprotein concentrations in patients with breast cancer," *Clinical Chemistry*, 49(10):1579-1598, (2003).

Chandler, et al., "Matrix metalloproteinases degrade myelin basic protein," *Neuroscience Lett.*, 201(3):223-226, (1995).

Chang and Werb, "The many faces of metalloproteases: cell growth, invasion, angiogenesis and metastasis," *Trends Cell Biol.*, 11:537-543, (2001).

Christianson, et al., "NH2-terminally truncated HER-2/neu protein: relationship with shedding of the extracellular domain and with prognostic factors in breast cancer," *Cancer Res.*, 58:5123-5129, (1998).

Codony-Servat, et al., "Cleavage of the HER2 ectodomain is a pervanadate-activable process that is inhibited by the tissue inhibitor of metalloproteases-1 in breast cancer cells," *Cancer Research*, 59(6):1196-1201, (1999).

Coussens, et al., "Matrix metalloproteinase inhibitors and cancer: trials and tribulations," *Science*, 295:2387-2392, (2002).

Doherty, et al, "The HER2/neu receptor tyrosine kinase gene encodes a secreted autoinhibitor," *Proc. Natl. Acad. Sci. USA*, 96:10869-10874, (1999).

Flickinger, et al., "An alternatively processed mRNA from the avian c-erbB gene encodes a soluble, truncated form of the receptor that can block ligand-dependent transformation," *Mol. Cell. Biol.*, 12:883-893, (1992).

Friedman, et al., "Clinical Benefit of INCB7839, a Potent and Selective Inhibitor of ADAM10 and ADAM17, in Combination with Trastuzumab in Metastatic HER2 Positive Breast Cancer Patients." Abstract and slide presentation from the 32nd Annual San Antonio Breast Cancer Symposium; Dec. 9-13, 2009, San Antonio, Texas; Incyte Corporation; 20 pgs.

Handsley, et al., Metalloproteinases and their inhibitors in tumor angiogenesis, *Int. J. Cancer*, 115:849-860, (2005).

Horiuchi, et al, "Potential role for ADAM15 in pathological neovascularization in mice," *Mol. Cell. Biol.*, 23:5614-5624, (2003).

Justman and Clinton, "Herstatin, an autoinhibitor of the human epidermal growth factor receptor 2 tyrosine kinas, modulates epidermal growth factor signalling pathways resulting in growth arrest," *J. Biol. Chem*, 277:20618-20624, (2002).

Kuipers, et al., "N4-unsubstituted N1-arylpiperazines as high-affinity 5-HT1A receptor ligands," *J. Med. Chem.*, 38(11):1942-1954, (1995).

Lee and Maihle, "Isolation and characterization of four alternate c-erbB3 transcripts expressed in ovarian carcinoma-derived cell lines and normal human tissues," *Oncogene*, 16:3243-3252, (1998).

Leitzel, et al., "Elevated soluble c-erbB-2 antigen levels in the serum and effusions of a proportion of breast cancer patients," *J. Clin. Oncol.* 10:1438-1443, (1992).

Liu, et al., *Cancer Bio. Ther.*, 5(6):www.landesbioscience.com/journals/cbt/abstract.php?id=2708, (2006).

Liu, et al., "Selective inhibition of ADAM metalloproteases blocks HER-2 extracellular domain (ECD) cleavage and potentiates the anti-tumor effects of trastuzumab", *Cancer Biology & Therapy*, 5(6):648-656 (2006).

Low, et al., "The matrix metalloproteinase inhibitor batimastat (BB-94) retards human breast cancer solid tumor growth but not ascites formation in nude mice", *Clinical Cancer Research*, 2:1207-1214, (1996).

Molina, et al., "NH(2)-terminal truncated HER-2 protein but not full-length receptor is associated with nodal metastasis in human breast cancer," *Clinical Cancer Research*, 8(2):347-353, (2002).

(56) References Cited

OTHER PUBLICATIONS

Molina, et al, "Trastuzumab (herceptin), a humanized anti-HER2 receptor monoclonal antibody, inhibits basal and activated HER2 ectodomain devage in breast cancer cells," Cancer Res. 61:4744-4739, (2001).

Moss and Lambert, "Shedding of membrane proteins by ADAM family proteases," Essays in Biochemistry, 38:141-153, (2002).

Pegram, et al., "Phase-2 study of receptor-enhanced chemosensitivity using recombinant humanized anti-p185 her2/neu monoclonal antibody plus cisplatin in patients with HER2/neu overexpressing metastatic breast cancer refractory to chemotherapy treatment," J. Clin. Oncol., 16:2659-2671, (1998).

Petch, et al., "A truncated, secreted form of the epidermal growth factor receptor is encoded by an alternatively spliced transcript in normal rat tissue," Mol. Cell. Biol, 10:2973-2982, (1990).

Rosendahl, et al., "Identification and characterization of a pro-tumor necrosis factor-alpha-processing enzyme from the ADAM family of zinc metalloproteases," Biol. Chem., 272(39):24588-24593, (1997).

Saus, et al., "The complete primary structure of human matrix metalloproteinase-3. Identity with stromelysin," J. Biol. Chem., 263(14):6742-6745, (1988).

Scott, et al., "A truncated intracellular HER2/neu receptor produced by alternative RNA processing affects growth of human carcinoma cells," Mol. Cell. Biol, 13:2247-2257, (1993).

Seals and Courtneidge, "The ADAMs family of metalloproteases: multidomain proteins with multiple functions," Genes Dev., 17:7-30, (2003).

Shepherd, F. A., "Targeted therapy for lung cancer at the clinical level." Proceedings of the American Association for Cancer Research, 43:1167-1168, (2002).

Sledge, et al., "Angiogenesis and Antiangiogenic Therapy," Current Problems in Cancer, Mosby, St. Louis, MO, US, 26(1):6-59, (2002).

Templeton, et al., "Cloning and characterization of human tumor cell interstitial collagenase," Cancer Research, 50(17):5431-5437, (1990).

Xue, et al., "Rational design, synthesis and structure-activity relationships of a cyclic succinate series of TNF-alpha converting enzyme inhibitors. Part 1: lead identification," Biorg. Med. Chem. Left., 13(24):4293-4297, (2003).

Xue, et al., "Rational design, synthesis and structure-activity relationships of a cyclic succinate series of TNF-alpha converting enzyme inhibitors. Part 2: lead optimization," Biorg. Med. Chem. Lett., 13(24):4299-4304, (2003).

Yamamoto, et al, "Similarity of protein encoded by the human c-erb-B-2 gene to epidermal growth factor receptor," Nature, 319:230-234, (1986).

Yoshiizumi, et al., "Synthesis and structure-activity relationships of 5,6,7,8 tetrahydropyrido[3,4-b]pyrazine-based hydroxamic acids as HB-EGF shedding inhibitors," Biorg. Med. Chem., 11(3):433-450, (2003).

Zhou, et al., Expert Opin. Incestig. Drugs, 14(6):591-606 (2005).

Zhou, et al., "Targeting ADAM-mediated ligand cleavage to inhibit HER3 and EGFR pathways in non-small cell lung cancer," Cancer Cell 10(1): 39-50, (2006).

Alana M. Harris, Ph.D. (Authorized Officer); International Search Report for Application PCT/US04/10278 (WO2044/089294); Dec. 2, 2005.

Alana M. Harris, Ph.D. (Authorized Officer); Written Opinion for Application PCT/US04/10278 ; (WO2044/089294); Dec. 2, 2005.

Alana M. Harris, Ph.D. (Authorized Officer); International Preliminary Report on Patentability for Application PCT/US04/10278 (WO2044/089294); May 8, 2006.

Supplementary Partial European Search Report dated Aug. 19, 2009 for European Appln. No. EP04758815 (8 pgs.).

Altschul et al., "Basic local alignment search tool," J. Mol. Biol., 1990, 215: 403-410.

Altschul et al., "Gapped Blast and Psi-Blast: a new generation of protein database search programs," Nucleic Acids Research, 1997, 25(17): 3389-3402.

Barbas, "Synthetic human antibodies," Nature Medicine, 1995, 1:837-839.

Beerli et al , "Inhibition of signaling from Type 1 receptor tyrosine kinases via intracellular expression of single-chain antibodies," Breast Cancer Res Treat, 1996, 38: 11-17.

Blume-Jensen et al., "Oncogenic kinase signaling," Nature, 2001, 411: 355-365.

Bulinksi et al., "Overexpression of MAP4 inhibits organelle motility and trafficking in vivo," J Cell Sci, Dec. 1997, 110: 3055-3064.

Burton et al., "Human antibodies from combinatorial libraries," Adv Immunol 1994, 57: 191-280.

Carraway and Cantley, "A neu acquaintance for erbB3 and erbB4: a role for receptor heterodimerization in growth signaling," Cell, Jul. 1994, 78: 5-8.

Cech et al., "RNA catalysis by a group I ribozyme. Developing a model for transition state stabilization," J Biol Chem, Sep. 1992, 267: 17479-17482.

Cech, "Ribozymes and their medical implications," JAMA, Nov. 1988, 260: 3030.

Coussens et al., "Tyrosine kinase receptor with extensive homology to EGF receptor shares chromosomal location with neu oncogene," Science, Dec. 1985, 230: 1132-1139.

Cranage et al., "Identification of the human cytomegalovirus glycoprotein B gene and induction of neutralizing antibodies via its expression in recombinant vaccinia virus," Embo J, Nov. 1986, 5: 3057-3063.

Datta, S.R., et al., "Cellular survival: a play in three Akts," Genes Dev, Nov. 1999, 13: 2905-2927.

De Kruif et al., "Selection and Application of Human Single Chain Fv Antibody Fragments from a Semi-synthetic Phage Antibody Display Library with Designed CDR3 Regions," J. Mol. Biol., 1995, 248:97-105.

DiFiore et al., "erbB-2 Is a Potent Oncogene When Overexpressed in NIH/3T3 Cells," Science, 1987, 237: 178-182.

Dougall et al., "The neu-oncogene: signal transduction pathways, transformation mechanisms and evolving therapies," Oncogene, 1994, 9: 2109-2123.

Earp et al., "Heterodimerization and functional interaction between EGF receptor family members: A new signaling paradigm with implications for breast cancer research," Breast Cancer Research and Treatment, 1995, 35:115-132.

Elbashir et al., "Duplexes of 21-nucleotide RNAs mediate RNA interference in cultured mammalian cells," Nature, 2001, 411: 494-498.

Paddison et al., "Stable suppression of gene expression by RNAi in mammalian cells," PNAS, Feb. 2002, 99: 1443-1448.

Fourie et al., "Catalytic Activity of Adams, ADAM15, and MDC-L (ADAM28) on Synthetic Peptide Substrates and in Ectodomain Cleavage of CD23*," J. Biol. Chem., Aug. 2003, 278(33):30469-77.

Gerhardt et al., eds., "Methods for General and Molecular Bacteriology," American Society for Microbiology, 1994, p. 574.

Gibson et al., "A Novel Method for Real Time Quantitative RT-PCR," Genome Research, 1996, 6: 995-1001.

Gu et al., "Construction and Expression of Mouse-human Chimeric Antibody SZ-51 Specific for Activated Platelet P-selectin," Thrombosis and Hematosis, 1997, 77:755-759.

Hampel et al., RNA Catalytic Properties of the Minimum (-)sTRSV Sequence, Biochemistry, 1989, 28: 4929-4933.

Hartmann et al., "The disintegrin/metalloprotease ADAM 10 is essential for Notch signaling but not for α-secretase activity in fibroblasts," Human Molecular Genetics, 2002, 11: 2615-24.

Hasselhoff and Gerlach, "Simple RNA enzymes with new and highly specific endoribonuclease activities," Nature, 1988, 334:585.

Hawkins, "New Anticancer Agents: Taxol, Camptothecin Analogs, and Anthrapyrazoles," Oncology, Dec. 1992, 12(6):17-30.

Hermanto et al., "ErbB2-overexpressing human mammary carcinoma cells display an increased requirement for the phosphatidylinositol 3-kinase signaling pathway in anchorage-independent growth," Oncogene, 2001, 20: 7551-7562.

Horwitz, "Mechanism of action of taxol," Trends Pharmacol. Sci, 1992, 13: 134-146.

(56) References Cited

OTHER PUBLICATIONS

Hudziak et al., "Increased expression of the putative growth factor receptor p185HER2 causes transformation and tumorigenesis of NIH 3T3 cells," Proc. Natl. Acad. Sci. USA, 1987, 84: 7159-7163.
Hynes and Steen, "The biology of erbB-2/neu/Her-2 and its role in cancer," Biochimica et Biophysica Acta, 1994, 1198: 165-184.
Karlin and Altschul, "Methods for assessing the statistical significance of molecular sequence features by using general scoring schemes," Proc. Natl. Acad. Sci. USA, Mar. 1990, 87:2264-2268.
Karlin and Altschul, "Applications and statistics for multiple high-scoring segments in molecular sequences," Proc. Natl. Acad. Sci. USA, Jun. 1993, 90: 5873-5877.
Lee et al., "Requirement for neuregulin receptor erbB2 in neural and cardiac development," Nature, Nov. 1995, 378: 394-398.
Levine et al., "Measurement of Specific Protease Activity Utilizing Fluorescence Polarization," Anal. Biochem., 1997, 247:83-88.
Lin and Clinton, "A soluble protein related to the HER-2 proto-oncogene product is released from human breast carcinoma cells," Oncogene, 1991, 6: 639-643.
Kay et al., "Gene therapy," Proc. Natl. Acad. Sci. USA, Nov. 1997, 94: 12744-12746.
Marcus-Sakura, "Techniques for Using Antisense Oligodeoxyribonucleotides to Study Gene Expression," Anal. Biochem., 1988, 172:289.
Marks et al., "By-Passing Immunication Human Antibodies from V-gene Libraries Displayed on Phage," J. Mol. Biol., 1991, 222: 581-597.
Martin et al., "The Role of ADAM 15 in Gomerular Mesangial Cell Migration," The Journal of Biological Chemistry, Sep. 2002, 277(37): 33683-33689.
Muhlradt and Sasse, "Epothilone B Stabilizes Microtubuli of Macrophages Like Taxol without Showing Taxol-like Endotoxin Activity," Cancer Research, Aug. 1997, 57: 3344-3346.
Muri et al., "Hydroxamic acids as pharmacological agents," Curr. Med. Chem. 2002, 9(17): 1631-53.
Nicolaou et al., "Synthesis of epothilones A and B in solid and solution phase," Nature, 1997, 387: 268-272.
Panda et al., "Differential Effects of Vinblastine on Polymerization and Dynamics at Opposite Microtubule Ends," The Journal of Biological Chemistry, Nov. 1996, 271(47): 29807-29812.
Panda et al., "Stabilization of microtubule dynamics by estramustine by binding to a novel site in tubulin: a possible mechanistic basis for its antitumor action," Proc. Natl. Acad. Sci. USA, Sep. 1997, 94: 10560-10564.
PCT/US04/10278: International Preliminary Report on Patentability, May 8, 2006, 3 pages.
PCT/US04/10278: International Search Report, Dec. 2, 2005, 3 pages.
PCT/US04/10278: Written Opinion, Dec. 2, 2005, 3 pages.
Poindexter et al., The identification of seven metalloproteinase-disintegrin (ADAM) genes from genomic libraries, Gene, 1999, 237: 61-70.
Ponder, "Cancer genetics," Nature, 2001, 411: 336-341.
Preaudator et al., "A Homogeneous Caspase-3 Activity Assay Using HTRF® Technology," J. Biomol. Screen, 2002, 7: 267-274.
Pupa et al., "The extracellular domain of the c-erbB-2 oncoprotein is released from tumor cells by proteolytic cleavage," Oncogene, 1993, 8:2917-2923.
Qian et al., "Intermolecular Association and Trans-phosphorylation of Different neu-Kinase Forms Permit SH2-dependent Signaling and Oncogenic Transformation," Oncogene, 1995, 10: 211-219.
Radtke and Raj, "The Role of Notch In Tumorigenesis: Oncogene or Tumour Suppressor?," Nat. Rev. Cancer, 2003, 3: 756-67.
Rio et al., "Tumor Necrosis Factor-a-converting Enzyme Is Required for Cleavage of erbB4/HER4*," The Journal of Biological Chemistry, Apr. 2000, 275(14): 10379-10387.
Rowinsky et al., "Taxol: A Novel Investigational Antimicrotubule Agent," Natl. Canc. Inst., 1990, 82: 1247-1259.
Seals and Courtneidge, "The ADAMs family of metalloproteases: multidomain proteins with multiple functions," Genes & Development, 2003, 17: 7-30.
Sharp, "RNA interference—2001," Genes & Development, 2001, 15: 485-490.
Slamon et al., "Human Breast Cancer: Correlation of Relapse and Survival with Amplification of the HER-2/neu Oncogene," Science, 1987, 235: 177-182.
Slamon et al., "Studies of the HER-2/neu Proto-oncogene in Human Breast and Ovarian Cancer," Science, 1989, 244:707-712.
Tuschl, "Expanding small RNA interference," Nature Biotech, 2002, 20: 446-448.
Tuszynski et al., "Thrombospondin Promotes Platelet Aggregation," Blood, Jul. 1988, 72(1): 109- 115.
Van Slooten et al., "Outgrowth of BT-474 human breast cancer cells in immune-deficient mice: a new in vivo model for homone-dependent breast cancer," British Journal of Cancer, 1995, 72: 22-30.
Vasquez et al., "Nanomolar Concentrations of Nocodazole Alter Microtubule Dynamic Instability In Vivo and in Vitro," Molecular Biology of the Cell, Jun. 1997, 8: 973-985.
Vecchi and Carpenter, "Constitutive Proteolysis of the ErbB-4 Receptor Tyrosine Kinase by a Unique, Sequential Mechanism," The Journal of Cell Biology, Nov. 1997, 139(4): 995-1003.
Weintraub, "Antisense RNA and DNA," Scientific American, 1990, 262:40-46.
Wilson et al., "Human Hypertension Caused by Mutations in WNK Kinases," Science, Aug. 2001, 293: 1107-1112.
Wright et al., "Genetically Engineered Antibodies: Progress and Prospects," Critical Rev. Immunol., 1992, 12: 125-168.
Yan et al., "The metalloprotease Kuzbanian (ADAM10) mediates the transactivation of EGF receptor by G protein-coupled receptors," The Journal of Cell Biology, Jul. 2002, 158(2): 221-226.
Zabrecky et al., "The Extracellular Domain of p185/neu Is Released from the Surface of Human Breast Carcinoma Cells, SK-BR-3*," The Journal of Biological Chemistry, Jan. 1991, 266(3): 1716-1720.
Fridman, J. et al., "Preclinical characterization of INCB7839, a Potent and Selective Inhibitor of ErbB Ligand and HER2 Receptor Shedding. Inhibition of ADAM10 and ADAM17 for the Treatment of Breast Cancer," 30th Annual San Antonio Breast Cancer Symposium, Dec. 13-16, 2007.
Infante, J. et al., "A Multicenter Phase Ib Study of the Safety, Pharmacokinetics, Biological Activity and Clinical Efficacy of INCB7839, a Potent and Selective Inhibitor of ADAM10 and ADAM17," 30th Annual San Antonio Breast Cancer Symposium, Dec. 13-16, 2007.

Figure 1

| Human ADAM family member | Encodes functional ADAM | Consensus sequences for active metalloproteinase | Expressed in HER2 shedding cell lines | HER2 sheddase candidates |
|---|---|---|---|---|
| ADAM1 | - | | | |
| ADAM2 | + | | | |
| ADAM3 | - | | | |
| ADAM6 | + | | | |
| ADAM7 | + | | | |
| ADAM8 | + | + | + | + |
| ADAM9 | + | + | + | + |
| ADAM10 | + | + | + | + |
| ADAM11 | + | | | |
| ADAM12 | + | + | - | -* |
| ADAM15 | + | + | + | + |
| ADAM17 | + | + | + | - |
| ADAM18 | + | | | |
| ADAM19 | + | + | - | - |
| ADAM20 | +/- | + | + | +/- |
| ADAM21 | + | + | + | + |
| ADAM22 | + | | | |
| ADAM23 | + | | | |
| ADAM28 | + | + | - | - |
| ADAM29 | + | | | |
| ADAM30 | + | + | - | - |
| ADAM32 | + | | | |
| ADAM33 | + | + | + | + |

Figure 2

| Gene | Forward Primer Sequence (5'-3') | Reverse Primer Sequence (5'-3') | Probe Sequence (5'-3') |
|---|---|---|---|
| ADAM8 | TGCTCCTCCGGTCACTGTG<br>SEQ ID NO:9 | TTGGCTTGATGACCTGCTTTG<br>SEQ ID NO:21 | CCCACCCTTCCCAGTTCCTGTCTACAC<br>SEQ ID NO:33 |
| ADAM9 | TGTCAAGTCATCTTTGGCTCAAA<br>SEQ ID NO:10 | AAATCTGTCACCTTTAGAATTCACTTCA<br>SEQ ID NO:22 | CAAGGCTGCCCCCAAAGATTGTTTC<br>SEQ ID NO:34 |
| ADAM10 | TCCAAAGTTGCCTCCTCCTAAA<br>SEQ ID NO:11 | GGGCCGCTGACGCTG<br>SEQ ID NO:23 | AGACCTCCACAGCCCATTCAGCAACC<br>SEQ ID NO:35 |
| ADAM12 | ATGAGGAAGCCGCCAGATT<br>SEQ ID NO:12 | CAACATTCTGACACTGCAGCAA<br>SEQ ID NO:24 | CTACCCACCGAAGGACAATCCCAGG<br>SEQ ID NO:36 |
| ADAM15 | ACAGGCACTGCTACTGTGAGGA<br>SEQ ID NO:13 | CCAAGCATCACCAGGACCA<br>SEQ ID NO:25 | TCAAAGCAACCAGCTCCCTGACCAC<br>SEQ ID NO:37 |
| ADAM17 | GCATGGATTCTGCATCGGT<br>SEQ ID NO:14 | TGCAGGCGGCCTGG<br>SEQ ID NO:26 | AAACCCTTTCCTGCGCCCCAGA<br>SEQ ID NO:38 |
| ADAM19 | TCTCAAATAGAGAGGACGGAGTCGTCC<br>SEQ ID NO:15 | GGGAAACGATGCAATTTGGT<br>SEQ ID NO:27 | TCCAAGCCGGCCAATTCCCC<br>SEQ ID NO:39 |
| ADAM20 | TGCAAGGACAAAGGCTATGGA<br>SEQ ID NO:16 | TTTCCCATCACATTTAATCCTTCC<br>SEQ ID NO:28 | TAGTGCTGATAGTGGCCCACCTCCTAAGAACA<br>SEQ ID NO:40 |
| ADAM21 | AAGTGAAAGATGGTACTGTGTGTGG<br>SEQ ID NO:17 | CAGGTCTCAGGAAGGCAGACAT<br>SEQ ID NO:29 | CAGGAAAGATCTGCATCCATAAGAAGTGTGTCAG<br>SEQ ID NO:41 |
| ADAM28 | GATGACTCCTCAGTGGTCTTCCA<br>SEQ ID NO:18 | GGTGCCGGATTACCATAGCA<br>SEQ ID NO:30 | CTGTTCCCAATGGCGGTCATTTTTGT<br>SEQ ID NO:42 |
| ADAM30 | CCATTTGTGGCCCAAGAGA<br>SEQ ID NO:19 | GCAGTTCCCCATGTTCTGTGA<br>SEQ ID NO:31 | CTGTTGCCCCGACATCTGCGC<br>SEQ ID NO:43 |
| ADAM33 | CTCGCACCGCACATGGT<br>SEQ ID NO:20 | GCTCCCCGACAAGTCACTTC<br>SEQ ID NO:32 | ACTCTACCGTTCACCTAGATGGCCA<br>SEQ ID NO:44 |

Figure 3

| Shedding | ++++ | + | ++++ | ++ | ++ |
|---|---|---|---|---|---|
| Annotation | BT474 | SKOV3 | SKBR3 | MDA | T47D |
| ADAM8 | + | + | + | + | + |
| ADAM9 | + | + | + | + | + |
| ADAM10 | + | + | + | + | + |
| ADAM12 | + | + | + | - | - |
| ADAM15 | + | + | + | + | + |
| ADAM17 | + | + | + | + | + |
| ADAM19 | + | + | + | - | + |
| ADAM20 | + | + | + | + | + |
| ADAM21 | + | + | + | + | + |
| ADAM28 | - | + | - | + | - |
| ADAM30 | - | - | - | - | - |
| ADAM33 | + | + | + | + | + |

Figure 5
A
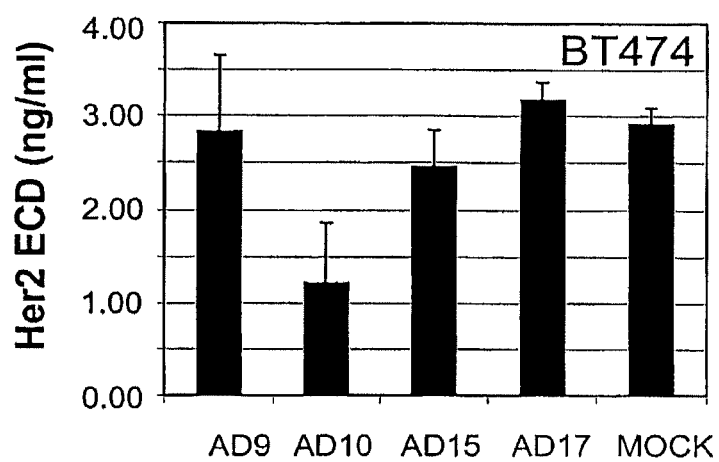
B
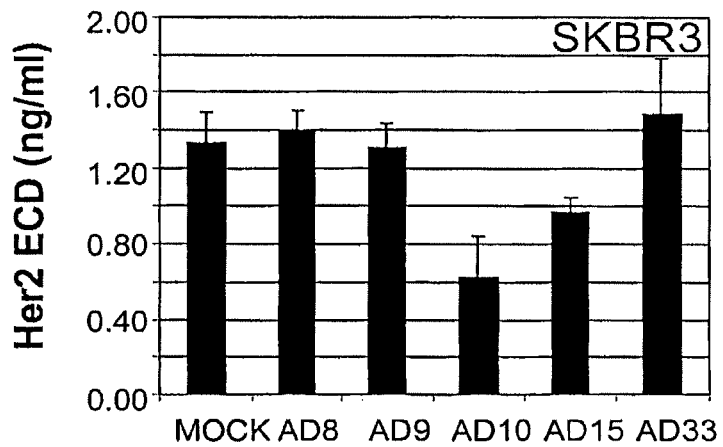

Human ADAM10    (SEQ ID NO:5)

GCGGCGGCAGGCCTAGCAGCACGGGAACCGTCCCCCG CGCGCATGCGCGCGCCCCTGAAGCG
CCTGGGGGACGGGTAGGGGCGGGAGGTAGGGGCGCGGCTCCGCGTGCCAGTTGGGTGCCCGC
GCGTCACGTGGTGAGGAAGGAGGCGGAGGTCTGAGTTTCGAAGGAGGGGGGAGAGAAGAGG
GAACGAGCAAGGGAAGGAAAGCGGGGAAAGGAGGAAGGAAACGAACGAGGGGGAGGGAGGTC
CCTGTTTTGGAGGAGCTAGGAGCGTTGCCGGCCCTGAAGTGGAG CGAGAGGGAGGTGCTTC
GCCGTTTCTCCTGCCAGGGGAGGTCCCGGCTTCCCGTGGAGGCTCCGGACCAAGCCCCTTCA
GCTTCTCCCTCCGGATCGATGTGCTGCTGTTAACCCGTGAGGAGGCGGCGGCGGCAGCG
GCAGCGGAAGATGGTGTTGCTGAGAGTGTTAATTCTGCTCCTCTCCTGGGCGGCGGGGATGG
GAGGTCAGTATGGGAATCCTTTAAATAAATATATCAGACATTATGAAGGATTA TCTTACAAT
GTGGATTCATTACACCAAAAACACCAGCGTGCCAAAAGAGCAGTCTCACATGAAGACCAATT
TTTACGTCTAGATTTCCATGCCCATGGAAGACATTTCAACCTACGAATGAAGAGGGACACTT
CCCTTTTCAGTGATGAATTTAAAGTAGAAACATCAAATAAAGTACTTGATTATGATACCTCT
CATATTTACACTGGACATATTTATGGTGAAGAAGGAAGTTTTAGCCATGGGTCTGTTATTG A
TGGAAGATTTGAAGGATTCATCCAGACTCGTGGTGGCACATTTTATGTTGAGCCAGCAGAGA
GATATATTAAAGACCGAACTCTGCCATTTCACTCTGTCATTTATCATGAAGATGATATTAAC
TATCCCCATAAATACGGTCCTCAGGGGGGCTGTGCAGATCATTCAGTATTTGAAAGAATGAG
GAAATACCAGATGACTGGTGTAGAGGAAGTAACACAGATACCTCAAGAAGAACATGCTGCTA
ATGGTCCAGAACTTCTGAGGAAAAAACGTACAACTTCAGCTGAAAAAAATACTTGTCAGCTT
TATATTCAGACTGATCATTTGTTCTTTAAATATTACGGAACACGAGAAGCTGTGATTGCCCA
GATATCCAGTCATGTTAAAGCGATTGATACAATTTACCAGACCACAGACTTCTCCGGAATCC
GTAACATCAGTTTCATGGTGAAACGCATAAGAATCAATACAACTGCTGATGAGAAGGACCCT
ACAAATCCTTTCCGTTTCCCAAATATTGGTGTGGAGAAGTTTCTGGAATTGAATTCTGAGCA
GAATCATGATGACTACTGTTTGGCCTATGTCTTCACAGACCGAGATTTTGATGATGGCGTAC
TTGGTCTGGCTTGGGTTGGAGCACCTTCAGGAAGCTCTGGAGGAATATGTGAAAAAAGTAAA
CTCTATTCAGATGGTAAGAAGAAGTCCTTAAACACTGGAATTATTACTGTTCAGAACTATGG
GTCTCATGTACCTCCCAAAGTCT CTCACATTACTTTTGCTCACGAAGTTGGACATAACTTTG
GATCCCCACATGATTCTGGAACAGAGTGCACACCAGGAGAATCTAAGAATTTGGGTCAAAAA
GAAAATGGCAATTACATCATGTATGCAAGAGCAACATCTGGGGACAAACTTAACAACAATAA
ATTCTCACTCTGTAGTATTAGAAATATAAGCCAAGTTCTTGAGAAGAAGAGAAACAACTGTT
TTGTTGAATCTGGCCAACCTATTTGTGGAAA TGGAATGGTAGAACAAGGTGAAGAATGTGAT
TGTGGCTATAGTGACCAGTGTAAAGATGAATGCTGCTTCGATGCAAATCAACCAGAGGGAAG
AAAATGCAAACTGAAACCTGGGAAACAGTGCAGTCCAAGTCAAGGTCCTTGTTGTACAGCAC
AGTGTGCATTCAAGTCAAAGTCTGAGAAGTGTCGGGATGATTCAGACTGTGCAAGGGAAGGA
ATATGTAATGGCTTCACAGCTCTCTGCCCAGCATCTGAC CCTAAACCAAACTTC

FIGURE 12A-1

ACAGACTGTAATAGGCATACACAAGTGTGCATTAATGGGCAATGTGCAGGTTCTATCTGTGA
GAAATATGGCTTAGAGGAGTGTACGTGTGCCAGTTCTGATGGCAAAGATGATAAAGAATTAT
GCCATGTATGCTGTATGAAGAAAATGGACCCATCAACTTGTGCCAGTACAGGGTCTGTGCAG
TGGAGTAGGCACTTCAGTGGTCGAACCATCACCCT GCAACCTGGATCCCCTTGCAACGATTT
TAGAGGTTACTGTGATGTTTTCATGCGGTGCAGATTAGTAGATGCTGATGGTCCTCTAGCTA
GGCTTAAAAAAGCAATTTTTAGTCCAGAGCTCTATGAAAACATTGCTGAATGGATTGTGGCT
CATTGGTGGGCAGTATTACTTATGGGAATTGCTCTGATCATGCTAATGGCTGGATTTATTAA
GATATGCAGTGTTCATACTCCAAGTAGTAATCCAAAGTTGCCT CCTCCTAAACCACTTCCAG
GCACTTTAAAGAGGAGGAGACCTCCACAGCCCATTCAGCAACCCCAGCGTCAGCGGCCCCGA
GAGAGTTATCAAATGGGACACATGAGACGCTAACTGCAGCTTTTGCCTTGGTTCTTCCTAGT
GCCTACAATGGGAAAACTTCACTCCAAAGAGAAACCTATTAAGTCATCATCTCCAAACTAAA
CCCTCACAAGTAACAGTTGAAGAAAAAATGGCAAGAGATCATATCCTCAGA CCAGGTGGAAT
TACTTAAATTTTAAAGCCTGAAAATTCCAATTTGGGGGTGGGAGGTGGAAAAGGAACCCAAT
TTTCTTATGAACAGATATTTTTAACTTAATGGCACAAAGTCTTAGAATATTATTATGTGCCC
CGTGTTCCCTGTTCTTCGTTGCTGCATTTTCTTCACTTGCAGGCAAACTTGGCTCTCAATAA
ACTTTTACCACAAATTGAAATAAATATATTTTTTTCAACTGCCAATCAAGGCTAGGAGG CTC
GACCACCTCAACATTGGAGACATCACTTGCCAATGTACATACCTTGTTATATGCAGACATGT
ATTTCTTACGTACACTGTACTTCTGTGTGCAATTGTAAACAGAAATTGCAATATGGATGTTT
CTTTGTATTATAAAATTTTTCCGCTCTTAATTAAAATTACTGTTTAATTGACATACTCAGG
ATAACAGAGAATGGTGGTATTCAGTGGTCCAGGATTCTGTAATGCTTTACACAGGCAGTTTT
GAAATGAAAATCAATTTACC

FIGURE 12A-2

ADAM10 peptide  (SEQ ID NO:6)

MVLLRVLILLLSWAAGMGGQYGNPLNKYIRHYEGLSYNVDSLHQKHQRAKRAVSHEDQFLRL
DFHAHGRHFNLRMKRDTSLFSDEFKVETSNKVLDYDTSHIYTGHIYGEEGSFSHGSVIDGRF
EGFIQTRGGTFYVEPAERYIKDRTLPFHSVIYHEDDINYPHKYGPQGGCADHSVFERMRKYQ
MTGVEEVTQIPQEEHAANGPELLRKKRTTSAEKNTCQLYIQTDHLFFKYYGTREAVIAQISS
HVKAIDTIYQTTDFSGIRNISFMVKRIRINTTADEKDPTNPFRFPNIGVEKFLELNSEQNHD
DYCLAYVFTDRDFDDGVLGLAWVGAPSGSSGGICEKSKLYSDGKKKSLNTGIITVQNYGSHV
PPKVSHITFAHEVGHNFGSPHDSGTECTPGESKNLGQKENGNYIMYARATSGDKLNNNKFSL
CSIRNISQVLEKKRNNCFVESGQPICGNGMVEQGEECDCGYSDQCKDECCFDANQPEGRKCK
LKPGKQCSPSQGPCCTAQCAFKSKSEKCRDDSDCAREGICNGFTALCPASDPKPNFTDCNRH
TQVCINGQCAGSICEKYGLEECTCASSDGKDDKELCHVCCMKKMDPSTCASTGSVQWSRHFS
GRTITLQPGSPCNDFRGYCDVFMRCRLVDADGPLARLKKAIFSPELYENIAEWIVAHWWAVL
LMGIALIMLMAGFIKICSVHTPSSNPKLPPPKPLPGTLKRRRPPQPIQQPQRQRPRESYQMG
HMRR

FIGURE 12B

Human ADAM15 Variant 1    (SEQ ID NO:1)

(most abundant in cell lines examined)

CCGAGGCGACCTGGCCGCCGGCCGCTCCTCCGCGCGCTGTTCCGCACTTGCTGCCCTCGCCC
GGCCCGGAGCGCCGCTGCCATGCGGCTGGCGCTGCTCTGGGCCCTGGGGCTC CTGGGCGCGG
GCAGCCCTCTGCCTTCCTGGCCGCTCCCAAATATAGGTGGCACTGAGGAGCAGCAGGCAGAG
TCAGAGAAGGCCCCGAGGGAGCCCTTGGAGCCCCAGGTCCTTCAGGACGATCTCCCAATTAG
CCTCAAAAAGGTGCTTCAGACCAGTCTGCCTGAGCCCCTGAGGATCAAGTTGGAGCTGGACG
GTGACAGTCATATCCTGGAGCTGCTACAGAATAGGGAGTTGGTCCCAGGCCGCCCAACCC TG
GTGTGGTACCAGCCCGATGGCACTCGGGTGGTCAGTGAGGGACACACTTTGGAGAACTGCTG
CTACCAGGGAAGAGTGCGGGGATATGCAGGCTCCTGGGTGTCCATCTGCACCTGCTCTGGGC
TCAGAGGCTTGGTGGTCCTGACCCCAGAGAGAAGCTATACCCTGGAGCAGGGGCCTGGGGAC
CTTCAGGGTCCTCCCATTATTTCGCGAATCCAAGATCTCCACCTGCCAGGCCACACCTGTGC
CCTGAGCTGGCGGGAATCTGTACACACTCAGACGCCACCAGAGCACCCCTGGGACAGCGCC
ACATTCGCCGGAGGCGGGATGTGGTAACAGAGACCAAGACTGTGGAGTTGGTGATTGTGGCT
GATCACTCGGAGGCCCAGAAATACCGGGACTTCCAGCACCTGCTAAACCGCACACTGGAAGT
GGCCCTCTTGCTGGACACATTCTTCCGGCCCCTGAATGTACGAGTGGCACTAGTGGGCCTGG
AGGCCTGGACCCAGCGTGACCTGGTGGAGATCAGCCCAAACCCAGCTGTCACCCTCGAAAAC
TTCCTCCACTGGCGCAGGGCACATTTGCTGCCTCGATTGCCCCATGACAGTGCCCAGCTGGT
GACTGGTACTTCATTCTCTGGGCCTACGGTGGGCATGGCCATTCAGAACTCCATCTGTTCTC
CTGACTTCTCAGGAGGTGTGAACATGGACCACTCCACCAGCATCCTGGGAGTCGCCTCCTCC
ATAGCCCATGAGTTGGGCCACA GCCTGGGCCTGGACCATGATTTGCCTGGGAATAGCTGCCC
CTGTCCAGGTCCAGCCCCAGCCAAGACCTGCATCATGGAGGCCTCCACAGACTTCCTACCAG
GCCTGAACTTCAGCAACTGCAGCCGACGGGCCCTGGAGAAAGCCCTCCTGGATGGAATGGGC
AGCTGCCTCTTCGAACGGCTGCCTAGCCTACCCCCTATGGCTGCTTTCTGCGGAAATATGTT
TGTGGAGCCGGGCGAGCAGTGTGACTGTGG CTTCCTGGATGACTGCGTCGATCCCTGCTGTG
ATTCTTTGACCTGCCAGCTGAGGCCAGGTGCACAGTGTGCATCTGACGGACCCTGTTGTCAA
AATTGCCAGCTGCGCCCGTCTGGCTGGCAGTGTCGTCCTACCAGAGGGGATTGTGACTTGCC
TGAATTCTGCCCAGGAGACAGCTCCCAGTGTCCCCCTGATGTCAGCCTAGGGGATGGCGAGC
CCTGCGCTGGCGGGCAAGCTGTGTGCATGCACGGGCGT TGTGCCTCCTATGCCCAGCAGTGC
CAGTCACTTTGGGGACCTGGAGCCCAGCCCGCTGCGCCACTTTGCCTCCAGACAGCTAATAC
TCGGGGAAATGCTTTTGGGAGCTGTGGGCGCAACCCCAGTGGCAGTTATGTGTCCTGCACCC
CTAGAGATGCCATTTGTGGGCAGCTCCAGTGCCAGACAGGTAGGACCCAGCCTCTGCTGGGC

FIGURE 13A-1

```
TCCATCCGGGATCTACTCTGGGAGACAA TAGATGTGAATGGGACTGAGCTGAACTGCAGCTG
GGTGCACCTGGACCTGGGCAGTGATGTGGCCCAGCCCCTCCTGACTCTGCCTGGCACAGCCT
GTGGCCCTGGCCTGGTGTGTATAGACCATCGATGCCAGCGTGTGGATCTCCTGGGGGCACAG
GAATGTCGAAGCAAATGCCATGGACATGGGGTCTGTGACAGCAACAGGCACTGCTACTGTGA
GGAGGGCTGGGCACCCCCTGACTGCACCACTCAGCT CAAAGCAACCAGCTCCCTGACCACAG
GGCTGCTCCTCAGCCTCCTGGTCTTATTGGTCCTGGTGATGCTTGGTGCCAGCTACTGGTAC
CGTGCCCGCCTGCACCAGCGACTCTGCCAGCTCAAGGGACCCACCTGCCAGTACAGGGCAGC
CCAATCTGGTCCCTCTGAACGGCCAGGACCTCCGCAGAGGGCCCTGCTGGCACGAGGCACTA
AGGCTAGTGCTCTCAGCTTCCCGGCCCCCCTTCCAGGCCGCTG CCGCCTGACCCTGTGTCC
AAGAGACTCCAGTCTCAGGGGCCAGCCAAGCCCCACCCCAAGGAAGCCACTGCCTGCCGA
CCCCCAGGGCCGGTGCCCATCGGGTGACCTGCCCGGCCCAGGGGCTGGAATCCCGCCCCTAG
TGGTACCCTCCAGACCAGCGCCACCGCCTCCGACAGTGTCCTCGCTCTACCTCTGACCTCTC
CGGAGGTTCCGCTGCCTCCAAGCCGGACTTAGGGCTTCAAGAGGCGGGCGTG CCCTCTGGAG
TCCCCTACCATGACTGAAGGCGCCAGAGACTGGCGGTGTCTTAAGACTCCGGGCACCGCCAC
GCGCTGTCAAGCAACACTCTGCGGACCTGCCGGCGTAGTTGCAGCGGGGCTTGGGGAGGGG
CTGGGGGTTGGACGGGATTGAGGAAGGTCCGCACAGCCTGTCTCTGCTCAGTTGCAATAAAC
GTGACATCTTGG
```

FIGURE 13A-2

Human ADAM15 variant 1 peptide (SEQ ID NO:2)

MRLALLWALGLLGAGSPLPSWPLPNIGGTEEQQAESEKAPREPLEPQVLQDDLPISLKKVLQ
TSLPEPLRIKLELDGDSHILELLQNRELVPGRPTLVWYQPDGTRVVSEGHTLENCCYQGRVR
GYAGSWVSICTCSGLRGLVVLTPERSYTLEQGPGDLQGPPIISRIQDLHLPGHTCALSWRES
VHTQTPPEHPLGQRHIRRRRDVVTETKTVELVIVADHSEAQKYRDFQHLLNRTL EVALLLDT
FFRPLNVRVALVGLEAWTQRDLVEISPNPAVTLENFLHWRRAHLLPRLPHDSAQLVTGTSFS
GPTVGMAIQNSICSPDFSGGVNMDHSTSILGVASSIAHELGHSLGLDHDLPGNSCPCPGPAP
AKTCIMEASTDFLPGLNFSNCSRRALEKALLDGMGSCLFERLPSLPPMAAFCGNMFVEPGEQ
CDCGFLDDCVDPCCDSLTCQLRPGAQCASDGPCCQNCQLRPSGWQCRPTRGDCDLPEFCPGD
SSQCPPDVSLGDGEPCAGGQAVCMHGRCASYAQQCQSLWGPGAQPAAPLCLQTANTRGNAFG
SCGRNPSGSYVSCTPRDAICGQLQCQTGRTQPLLGSIRDLLWETIDVNGTELNCSWVHLDLG
SDVAQPLLTLPGTACGPGLVCIDHRCQRVDLLGAQECRSKCHGHGVCDSNRHCYCEEGWAPP
DCTTQLKATSSLTTGLLLSLLVLLVLVMLGASYWYRARLHQRLCQLKGPTCQYRAAQSGPSE
RPGPPQRALLARGTKASALSFPAPPSRPLPPDPVSKRLQSQGPAKPPPPRKPLPADPQGRCP
SGDLPGPGAGIPPLVVPSRPAPPPPTVSSLYL

FIGURE 13B

Human ADAM15 Variant 2 (longest form) (SEQ ID NO:3)

CCGAGGCGACCTGGCCGCCGGCCGCTCCTCCGCGCGCTGTTCCGCACTTGCTGCCCTCGCCC
GGCCCGGAGCGCCGCTGCCATGCGGCTGGCGCTGCTCTG GGCCCTGGGGCTCCTGGGCGCGG
GCAGCCCTCTGCCTTCCTGGCCGCTCCCAAATATAGGTGGCACTGAGGAGCAGCAGGCAGAG
TCAGAGAAGGCCCCGAGGGAGCCCTTGGAGCCCCAGGTCCTTCAGGACGATCTCCCAATTAG
CCTCAAAAAGGTGCTTCAGACCAGTCTGCCTGAGCCCCTGAGGATCAAGTTGGAGCTGGACG
GTGACAGTCATATCCTGGAGCTGCTACAGAATAGGGAGTTGGTCCCA GGCCGCCCAACCCTG
GTGTGGTACCAGCCCGATGGCACTCGGGTGGTCAGTGAGGGACACACTTTGGAGAACTGCTG
CTACCAGGGAAGAGTGCGGGGATATGCAGGCTCCTGGGTGTCCATCTGCACCTGCTCTGGGC
TCAGAGGCTTGGTGGTCCTGACCCCAGAGAGAAGCTATACCCTGGAGCAGGGGCCTGGGGAC
CTTCAGGGTCCTCCCATTATTTCGCGAATCCAAGATCTCCACCTGCCAGGCCACA CCTGTGC
CCTGAGCTGGCGGGAATCTGTACACACTCAGACGCCACCAGAGCACCCCTGGGACAGCGCC
ACATTCGCCGGAGGCGGGATGTGGTAACAGAGACCAAGACTGTGGAGTTGGTGATTGTGGCT
GATCACTCGGAGGCCCAGAAATACCGGGACTTCCAGCACCTGCTAAACCGCACACTGGAAGT
GGCCCTCTTGCTGGACACATTCTTCCGGCCCCTGAATGTACGAGTGGCACTAGTGGGCCTGG
AGGCCTGGACCCAGCGTGACCTGGTGGAGATCAGCCCAAACCCAGCTGTCACCCTCGAAAAC
TTCCTCCACTGGCGCAGGGCACATTTGCTGCCTCGATTGCCCCATGACAGTGCCCAGCTGGT
GACTGGTACTTCATTCTCTGGGCCTACGGTGGGCATGGCCATTCAGAACTCCATCTGTTCTC
CTGACTTCTCAGGAGGTGTGAACATGGACCACTCCACCAGCATCCTGGGAGTCGCCTCCTCC
ATAGCCCATGAGTTGGGCCACAGCCTGGGCCTGGACCATGATTTGCCTGGGAATAGCTGCCC
CTGTCCAGGTCCAGCCCCAGCCAAGACCTGCATCATGGAGGCCTCCACAGACTTCCTACCAG
GCCTGAACTTCAGCAACTGCAGCCGACGGGCCCTGGAGAAAGCCCTCCTGGATGGAATGGGC
AGCTGCCTCTTCGAACGGCTGCCTAGCCTACCCCCTATGGCTGCTTTCTGCGGAAATATGTT
TGTGGAGCCGGGCGAGCAGTGTGACTGTGGCTTCCTGGATGACTGCGTCGATCCCTGCTGTG
ATTCTTTGACCTGCCAGCTGAGGCCAGGTGCACAGTGTGCATCTGACGGACCCTGTTGTCAA
AATTGCCAGCTGCGCCCGTCTGGCTGGCAGTGTCGTCCTACCAGAGGGGATTGTGACTTGCC
TGAATTCTGCCCAGGAGACAGCTCCCAGTGTCCCCTGATGTCAGCCTAGGGGATGGCGAGC
CCTGCGCTGGCGGGCAAGCTGTGTG CATGCACGGGCGTTGTGCCTCCTATGCCCAGCAGTGC
CAGTCACTTTGGGGACCTGGAGCCCAGCCCGCTGCGCCACTTTGCCTCCAGACAGCTAATAC
TCGGGGAAATGCTTTTGGGAGCTGTGGGCGCAACCCCAGTGGCAGTTATGTGTCCTGCACCC
CT

FIGURE 14A-1

AGAGATGCCATTTGTGGGCAGCTCCAGTGCCAGACAGGTAGGACCCAGCCTCTGCTGGGCTC
CATCCGGGATCTACTCTGGGAGACAATAGATGTGAATGGGACTGAGCTGAACTGCAGCTGGG
TGCACCTGGACCTGGGCAGTGATGTGGCCCAGCCCCTCCTGACTCTGCCTGGCACAGCCTGT
GGCCCTGGCCTGGTGTGTATAGACCATCGATGCCAGCGTGTGGATCTCCTGGGGCACAGGA
ATGTCGAAGCAAATGCCATGGACATGGGGTCTGTGACAGCAACAGGCACTGCTACTGTGAGG
AGGGCTGGGCACCCCTGACTGCACCACTCAGCTCAAAGCAACCAGCTCCCTGACCACAGGG
CTGCTCCTCAGCCTCCTGGTCTTATTGGTCCTGGTGATGCTTGGTGCCAGCTACTGGTACCG
TGCCCGCCTGCACCAGCGACTCTGCCAGCTCAAGGGACCCACCTGCCAGTACAGGGCAGCCC
AATCTGGTCCCTCTGAACGGCCAGGACCTCCGCAGAGGGCCCTGCTGGCACGAGGCACTAAG
GCTAGTGCTCTCAGCTTCCCGGCCCCCCC TTCCAGGCCGCTGCCGCCTGACCCTGTGTCCAA
GAGACTCCAGGCTGAGCTGGCTGACCGACCCAATCCCCCTACCCGCCCTCTGCCCGCTGACC
CGGTGGTGAGAAGCCCGAAGTCTCAGGGGCCAGCCAAGCCCCCACCCCCAAGGAAGCCACTG
CCTGCCGACCCCCAGGGCCGGTGCCCATCGGGTGACCTGCCCGGCCCAGGGGCTGGAATCCC
GCCCCTAGTGGTACCCTCCAGACCAGCGCCACCGCCT CCGACAGTGTCCTCGCTCTACCTCT
GACCTCTCCGGAGGTTCCGCTGCCTCCAAGCCGGACTTAGGGCTTCAAGAGGCGGGCGTGCC
CTCTGGAGTCCCCTACCATGACTGAAGGCGCCAGAGACTGGCGGTGTCTTAAGACTCCGGGC
ACCGCCACGCGCTGTCAAGCAACACTCTGCGGACCTGCCGGCGTAGTTGCAGCGGGGCTTG
GGGAGGGGCTGGGGGTTGGACGGGATTGAGGAAGGTCCGCACAGC CTGTCTCTGCTCAGTTG
CAATAAACGTGACATCTTGG

FIGURE 14A-2

Human ADAM15 Variant 2 peptide (SEQ ID NO:4)

MRLALLWALGLLGAGSPLPSWPLPNIGGTEEQQAESEKAPREPLEPQVLQDDLPISLKKVLQ
TSLPEPLRIKLELDGDSHILELLQNRELVPGRPTLVWYQPDGTRVVSEGHTLENCCYQGRVR
GYAGSWVSICTCSGLRGLVVLTPERSYTLEQ GPGDLQGPPIISRIQDLHLPGHTCALSWRES
VHTQTPPEHPLGQRHIRRRRDVVTETKTVELVIVADHSEAQKYRDFQHLLNRTLEVALLLDT
FFRPLNVRVALVGLEAWTQRDLVEISPNPAVTLENFLHWRRAHLLPRLPHDSAQLVTGTSFS
GPTVGMAIQNSICSPDFSGGVNMDHSTSILGVASSIAHELGHSLGLDHDLPGNSCPCPGPAP
AKTCIMEASTDFLPGLNFSNCSRRALEKALLDGMGSCLF ERLPSLPPMAAFCGNMFVEPGEQ
CDCGFLDDCVDPCCDSLTCQLRPGAQCASDGPCCQNCQLRPSGWQCRPTRGDCDLPEFCPGD
SSQCPPDVSLGDGEPCAGGQAVCMHGRCASYAQQCQSLWGPGAQPAAPLCLQTANTRGNAFG
SCGRNPSGSYVSCTPRDAICGQLQCQTGRTQPLLGSIRDLLWETIDVNGTELNCSWVHLDLG
SDVAQPLLTLPGTACGPGLVCIDHRCQRVDLLGAQECRSKCHGHGVC DSNRHCYCEEGWAPP
DCTTQLKATSSLTTGLLLSLLVLLVLVMLGASYWYRARLHQRLCQLKGPTCQYRAAQSGPSE
RPGPPQRALLARGTKASALSFPAPPSRPLPPDPVSKRLQAELADRPNPPTRPLPADPVVRSP
KSQGPAKPPPPRKPLPADPQGRCPSGDLPGPGAGIPPLVVPSRPAPPPPTVSSLYL

FIGURE 14B

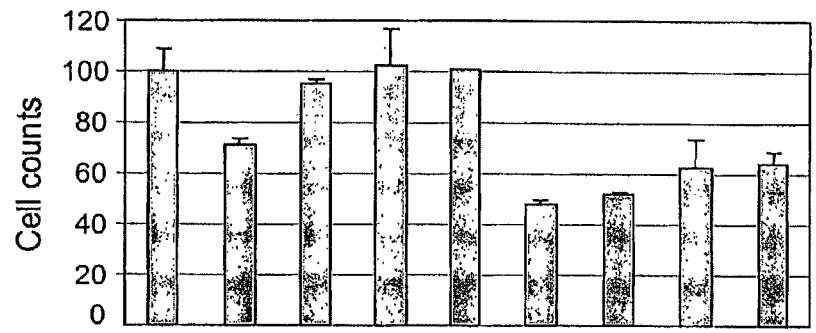
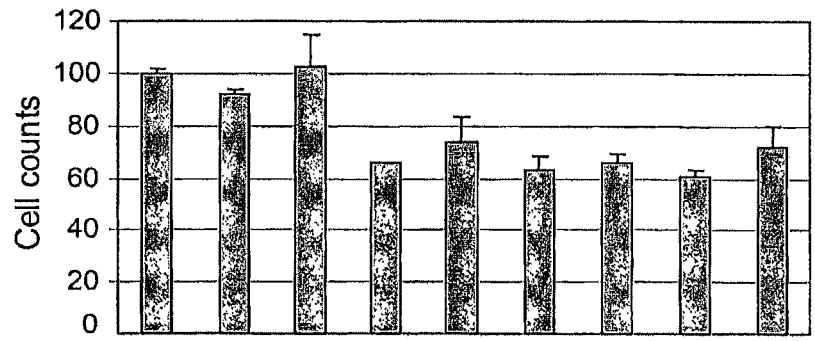
FIG. 18

SEQUENCE LISTING

<160> NUMBER OF SEQ ID NOS: 48

<210> SEQ ID NO 1
<211> LENGTH: 2864
<212> TYPE: DNA
<213> ORGANISM: Homo sapiens

<400> SEQUENCE: 1

```
ccgaggcgac ctggccgccg gccgctcctc cgcgcgctgt tccgcacttg ctgccctcgc      60
ccggcccgga gcgccgctgc catgcggctg gcgctgctct gggccctggg gctcctgggc     120
gcgggcagcc ctctgccttc ctggccgctc ccaaatatag gtggcactga ggagcagcag     180
gcagagtcag agaaggcccc gagggagccc ttggagcccc aggtccttca ggacgatctc     240
ccaattagcc tcaaaaaggt gcttcagacc agtctgcctg agccctgag gatcaagttg      300 gagctggacg gtgacagtca tatcctggag ctgctacaga atagggagtt ggtcccaggc     360
cgcccaaccc tggtgtggta ccagcccgat ggcactcggg tggtcagtga gggacacact     420
ttggagaact gctgctacca gggaagagtg cggggatatg caggctcctg ggtgtccatc     480
tgcacctgct ctgggctcag aggcttggtg gtcctgaccc cagagagaag ctatacctg      540 gagcaggggc ctggggacct tcagggtcct cccattattt cgcgaatcca agatctccac     600
ctgccaggcc acacctgtgc cctgagctgg cgggaatctg tacacactca gacgccacca     660
gagcaccccc tgggacagcg ccacattcgc cggaggcggg atgtggtaac agagaccaag     720
actgtggagt tggtgattgt ggctgatcac tcggaggccc agaaataccg ggacttccag     780
cacctgctaa accgcacact ggaagtggcc ctcttgctgg acacattctt ccggcccctg     840
aatgtacgag tggcactagt gggcctggag gcctggaccc agcgtgacct ggtggagatc     900
agcccaaacc cagctgtcac cctcgaaaac ttcctccact ggcgcagggc acatttgctg     960
cctcgattgc cccatgacag tgcccagctg gtgactggta cttcattctc tgggcctacg    1020
gtgggcatgg ccattcagaa ctccatctgt tctcctgact tctcaggagg tgtgaacatg    1080
gaccactcca ccagcatcct gggagtcgcc tcctccatag cccatgagtt gggccacagc    1140
ctgggcctgg accatgattt gcctgggaat agctgcccct gtccaggtcc agccccagcc    1200
aagacctgca tcatggaggc ctccacagac ttcctaccag gcctgaactt cagcaactgc    1260
agccgacggg ccctggagaa agccctcctg gatggaatgg gcagctgcct cttcgaacgg    1320
ctgcctagcc tacccctat ggctgctttc tgcggaaata tgtttgtgga gccgggcgag     1380
cagtgtgact gtggcttcct ggatgactgc gtcgatccct gctgtgattc tttgacctgc    1440
cagctgaggc caggtgcaca gtgtgcatct gacggaccct gttgtcaaaa ttgccagctg    1500
cgcccgtctg gctggcagtg tcgtcctacc agaggggatt gtgacttgcc tgaattctgc    1560
ccaggagaca gctcccagtg tcccctgat gtcagcctag gggatggcga gccctgcgct    1620
```

-continued

```
ggcgggcaag ctgtgtgcat gcacgggcgt tgtgcctcct atgcccagca gtgccagtca    1680
ctttggggac ctggagccca gcccgctgcg ccactttgcc tccagacagc taatactcgg    1740
ggaaatgctt ttgggagctg tgggcgcaac cccagtggca gttatgtgtc ctgcacccct    1800
agagatgcca tttgtgggca gctccagtgc agacaggta ggacccagcc tctgctgggc     1860
tccatccggg atctactctg ggagacaata gatgtgaatg ggactgagct gaactgcagc    1920
tgggtgcacc tggaccctgg gcagtgatgtg cccagccc cctgactct gcctggcaca      1980
gcctgtggcc ctggcctggt gtgtatagac catcgatgcc agcgtgtgga tctcctgggg    2040
gcacaggaat gtcgaagcaa atgccatgga catgggtct gtgacagcaa caggcactgc     2100
tactgtgagg agggctgggc acccctgac tgcaccactc agctcaaagc aaccagctcc     2160
ctgaccacag gctgctcct cagcctcctg gtcttattgg tcctggtgat gcttggtgcc     2220
agctactggt accgtgcccg cctgcaccag cgactctgcc agctcaaggg acccacctgc    2280
cagtacaggg cagcccaatc tggtccctct gaacggccag gacctccgca gagggccctg    2340
ctggcacgag gcactaaggc tagtgctctc agcttcccgg ccccccttc caggccgctg     2400
ccgcctgacc ctgtgtccaa gagactccag tctcagggc cagccaagcc cccaccccca    2460
aggaagccac tgcctgccga ccccagggc cggtgcccat cgggtgacct gcccggccca    2520
ggggctggaa tcccgcccct agtggtaccc tccagaccag cgccaccgcc tcgacagtg    2580
tcctcgctct acctctgacc tctccggagg ttccgctgcc tccaagccgg acttagggct    2640
tcaagaggcg ggcgtgccct ctggagtccc ctaccatgac tgaaggcgcc agagactggc    2700
ggtgtcttaa gactccgggc accgccacgc gctgtcaagc aacactctgc ggacctgccg    2760
gcgtagttgc agcgggggct tggggagggg ctggggttg gacgggattg aggaaggtcc     2820
gcacagcctg tctctgctca gttgcaataa acgtgacatc ttgg                     2864
```

<210> SEQ ID NO 2
<211> LENGTH: 838
<212> TYPE: PRT
<213> ORGANISM: Homo sapiens

<400> SEQUENCE: 2

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
                20                  25                  30

Gln Ala Glu Ser Glu Lys Ala Pro Arg Glu Pro Leu Glu Pro Gln Val
            35                  40                  45

Leu Gln Asp Asp Leu Pro Ile Ser Leu Lys Lys Val Leu Gln Thr Ser
        50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
                100                 105                 110

Thr Leu Glu Asn Cys Cys Tyr Gln Gly Arg Val Arg Gly Tyr Ala Gly
            115                 120                 125

Ser Trp Val Ser Ile Cys Thr Cys Ser Gly Leu Arg Gly Leu Val Val
        130                 135                 140

Leu Thr Pro Glu Arg Ser Tyr Thr Leu Glu Gln Gly Pro Gly Asp Leu
```

```
            145                 150                 155                 160
        Gln Gly Pro Pro Ile Ile Ser Arg Ile Gln Asp Leu His Leu Pro Gly
                        165                 170                 175
        His Thr Cys Ala Leu Ser Trp Arg Glu Ser Val His Thr Gln Thr Pro
                        180                 185                 190
        Pro Glu His Pro Leu Gly Gln Arg His Ile Arg Arg Arg Asp Val
                        195                 200                 205
        Val Thr Glu Thr Lys Thr Val Glu Leu Val Ile Val Ala Asp His Ser
                    210                 215                 220
        Glu Ala Gln Lys Tyr Arg Asp Phe Gln His Leu Leu Asn Arg Thr Leu
        225                 230                 235                 240
        Glu Val Ala Leu Leu Leu Asp Thr Phe Phe Arg Pro Leu Asn Val Arg
                        245                 250                 255
        Val Ala Leu Val Gly Leu Glu Ala Trp Thr Gln Arg Asp Leu Val Glu
                        260                 265                 270
        Ile Ser Pro Asn Pro Ala Val Thr Leu Glu Asn Phe Leu His Trp Arg
                        275                 280                 285
        Arg Ala His Leu Leu Pro Arg Leu Pro His Asp Ser Ala Gln Leu Val
                        290                 295                 300
        Thr Gly Thr Ser Phe Ser Gly Pro Thr Val Gly Met Ala Ile Gln Asn
        305                 310                 315                 320
        Ser Ile Cys Ser Pro Asp Phe Ser Gly Gly Val Asn Met Asp His Ser
                        325                 330                 335
        Thr Ser Ile Leu Gly Val Ala Ser Ser Ile Ala His Glu Leu Gly His
                        340                 345                 350
        Ser Leu Gly Leu Asp His Asp Leu Pro Gly Asn Ser Cys Pro Cys Pro
                        355                 360                 365
        Gly Pro Ala Pro Ala Lys Thr Cys Ile Met Glu Ala Ser Thr Asp Phe
                        370                 375                 380
        Leu Pro Gly Leu Asn Phe Ser Asn Cys Ser Arg Arg Ala Leu Glu Lys
        385                 390                 395                 400
        Ala Leu Leu Asp Gly Met Gly Ser Cys Leu Phe Glu Arg Leu Pro Ser
                        405                 410                 415
        Leu Pro Pro Met Ala Ala Phe Cys Gly Asn Met Phe Val Glu Pro Gly
                        420                 425                 430
        Glu Gln Cys Asp Cys Gly Phe Leu Asp Asp Cys Val Asp Pro Cys Cys
                        435                 440                 445
        Asp Ser Leu Thr Cys Gln Leu Arg Pro Gly Ala Gln Cys Ala Ser Asp
                    450                 455                 460
        Gly Pro Cys Cys Gln Asn Cys Gln Leu Arg Pro Ser Gly Trp Gln Cys
        465                 470                 475                 480
        Arg Pro Thr Arg Gly Asp Cys Asp Leu Pro Glu Phe Cys Pro Gly Asp
                        485                 490                 495
        Ser Ser Gln Cys Pro Pro Asp Val Ser Leu Gly Asp Gly Glu Pro Cys
                    500                 505                 510
        Ala Gly Gly Gln Ala Val Cys Met His Gly Arg Cys Ala Ser Tyr Ala
                    515                 520                 525
        Gln Gln Cys Gln Ser Leu Trp Gly Pro Gly Ala Gln Pro Ala Ala Pro
                    530                 535                 540
        Leu Cys Leu Gln Thr Ala Asn Thr Arg Gly Asn Ala Phe Gly Ser Cys
        545                 550                 555                 560
        Gly Arg Asn Pro Ser Gly Ser Tyr Val Ser Cys Thr Pro Arg Asp Ala
                        565                 570                 575
```

```
Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
                660                 665                 670

Cys Tyr Cys Glu Glu Gly Trp Ala Pro Pro Asp Cys Thr Thr Gln Leu
            675                 680                 685

Lys Ala Thr Ser Ser Leu Thr Thr Gly Leu Leu Ser Leu Leu Val
            690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
                740                 745                 750

Leu Leu Ala Arg Gly Thr Lys Ala Ser Ala Leu Ser Phe Pro Ala Pro
            755                 760                 765

Pro Ser Arg Pro Leu Pro Pro Asp Pro Val Ser Lys Arg Leu Gln Ser
            770                 775                 780

Gln Gly Pro Ala Lys Pro Pro Pro Arg Lys Pro Leu Pro Ala Asp
785                 790                 795                 800

Pro Gln Gly Arg Cys Pro Ser Gly Asp Leu Pro Gly Pro Gly Ala Gly
                805                 810                 815

Ile Pro Pro Leu Val Val Pro Ser Arg Pro Ala Pro Pro Pro Pro Thr
            820                 825                 830

Val Ser Ser Leu Tyr Leu
            835

<210> SEQ ID NO 3
<211> LENGTH: 2936
<212> TYPE: DNA
<213> ORGANISM: Homo sapiens

<400> SEQUENCE: 3
ccgaggcgac ctggccgccg gccgctcctc cgcgcgctgt tccgcacttg ctgccctcgc      60
ccggcccgga gcgccgctgc catgcggctg cgcgctgctct gggccctggg gctcctgggc     120
gcgggcagcc ctctgccttc ctggccgctc ccaaatatag gtggcactga ggagcagcag     180
gcagagtcag agaaggcccc gagggagccc ttggagcccc aggtccttca ggacgatctc     240
ccaattagcc tcaaaaaggt gcttcagacc agtctgcctg agccctgag gatcaagttg     300 gagctggacg tgacagtcca tatcctggag ctgctacaga atagggagtt ggtcccaggc     360
cgcccaaccc tggtgtggta ccagcccgat ggcactcggg tggtcagtga ggacacact      420 ttggagaact gctgctacca gggaagagtg cggggatatg caggctcctg ggtgtccatc     480
tgcacctgct ctgggctcag aggcttggtg gtcctgaccc cagagagaag ctataccctg     540
gagcaggggc ctgggggacct tcagggtcct cccattattt cgcgaatcca agatctccac     600
```

```
ctgccaggcc acacctgtgc cctgagctgg cgggaatctg tacacactca gacgccacca    660
gagcacccc tgggacagcg ccacattcgc cggaggcggg atgtggtaac agagaccaag    720
actgtggagt tggtgattgt ggctgatcac tcggaggccc agaaataccg ggacttccag    780
cacctgctaa accgcacact ggaagtggcc ctcttgctgg acacattctt ccggcccctg    840
aatgtacgag tggcactagt gggcctggag gcctggaccc agcgtgacct ggtggagatc    900
agcccaaacc cagctgtcac cctcgaaaac ttcctccact ggcgcagggc acatttgctg    960
cctcgattgc cccatgacag tgcccagctg gtgactggta cttcattctc tgggcctacg   1020
gtgggcatgg ccattcagaa ctccatctgt tctcctgact tctcaggagg tgtgaacatg   1080
gaccactcca ccagcatcct gggagtcgcc tcctccatag cccatgagtt gggccacagc   1140
ctgggcctgg accatgattt gcctgggaat agctgcccct gtccaggtcc agccccagcc   1200
aagacctgca tcatggaggc ctccacagac ttcctaccag gcctgaactt cagcaactgc   1260
agccgacggg ccctggagaa agccctcctg gatggaatgg gcagctgcct cttcgaacgg   1320
ctgcctagcc taccccctat ggctgctttc tgcggaaata tgtttgtgga gccgggcgag   1380
cagtgtgact gtggcttcct ggatgactgc gtcgatccct gctgtgattc tttgacctgc   1440
cagctgaggc caggtgcaca gtgtgcatct gacggaccct gttgtcaaaa ttgccagctg   1500
cgcccgtctg gctggcagtg tcgtcctacc agagggggatt gtgacttgcc tgaattctgc   1560
ccaggagaca gctcccagtg tccccctgat gtcagcctag gggatggcga gccctgcgct   1620
ggcgggcaag ctgtgtgcat gcacgggcgt tgtgcctcct atgcccagca gtgccagtca   1680
cttggggac ctggagccca gccgctgcg ccactttgcc tccagacagc taatactcgg   1740
ggaaatgctt ttgggagctg tgggcgcaac cccagtggca gttatgtgtc ctgcacccct   1800
agagatgcca tttgtgggca gctccagtgc cagacaggta ggacccagcc tctgctgggc   1860
tccatccggg atctactctg ggagacaata gatgtgaatg ggactgagct gaactgcagc   1920
tgggtgcacc tggacctggg cagtgatgtg gcccagcccc tcctgactct gcctggcaca   1980
gcctgtggcc ctggcctggt gtgtatagac catcgatgcc agcgtgtgga tctcctgggg   2040
gcacaggaat gtcgaagcaa atgccatgga catggggtct gtgacagcaa caggcactgc   2100
tactgtgagg agggctgggc ccccctgac tgcaccactc agctcaaagc aaccagctcc   2160
ctgaccacag ggctgctcct cagcctcctg gtcttattgg tcctggtgat gcttggtgcc   2220
agctactggt accgtgcccg cctgcaccag cgactctgcc agctcaaggg acccacctgc   2280
cagtacaggg cagcccaatc tggtccctct gaacggccag gacctccgca gagggccctg   2340
ctggcacgag gcactaaggc tagtgctctc agcttcccgg ccccccttc caggccgctg   2400
ccgcctgacc ctgtgtccaa gagactccag gctgagctgg ctgaccgacc caatcccct   2460
acccgccctc tgcccgctga cccggtggtg agaagcccga agtctcaggg gccagccaag   2520
ccccaccc caaggaagcc actgcctgcc gaccccagg gccggtgccc atcgggtgac   2580
ctgcccggcc caggggctgg aatcccgccc ctagtggtac cctccagacc agcgccaccg   2640
cctccgacag tgtcctcgct ctacctctga cctctccgga ggttccgctg cctccaagcc   2700
ggacttaggg cttcaagagg cgggcgtgcc ctctggagtc ccctaccatg actgaaggcg   2760
ccagagactg gcggtgtctt aagactccgg gcaccgccac gcgctgtcaa gcaacactct   2820
gcggacctgc cggcgtagtt gcagcggggg cttggggagg ggctggggt tggacgggat   2880
tgaggaaggt ccgcacagcc tgtctctgct cagttgcaat aaacgtgaca tcttgg       2936
```

-continued

<210> SEQ ID NO 4
<211> LENGTH: 862
<212> TYPE: PRT
<213> ORGANISM: Homo sapiens

<400> SEQUENCE: 4

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Thr Pro
            180                 185                 190

Pro Glu His Pro Leu Gly Gln Arg His Ile Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365

Gly Pro Ala Pro Ala Lys Thr Cys Ile Met Glu Ala Ser Thr Asp Phe
    370                 375                 380
```

```
Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
            405                 410                 415

Leu Pro Pro Met Ala Ala Phe Cys Gly Asn Met Phe Val Glu Pro Gly
        420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
        450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
            485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
            515                 520                 525

Gln Gln Cys Gln Ser Leu Trp Gly Pro Gly Ala Gln Pro Ala Ala Pro
        530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
            565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
        610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
            645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
        675                 680                 685

Lys Ala Thr Ser Ser Leu Thr Thr Gly Leu Leu Leu Ser Leu Leu Val
        690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
            725                 730                 735

Ala Ala Gln Ser Gly Pro Ser Glu Arg Pro Gly Pro Pro Gln Arg Ala
            740                 745                 750

Leu Leu Ala Arg Gly Thr Lys Ala Ser Ala Leu Ser Phe Pro Ala Pro
            755                 760                 765

Pro Ser Arg Pro Leu Pro Pro Asp Pro Val Ser Lys Arg Leu Gln Ala
        770                 775                 780

Glu Leu Ala Asp Arg Pro Asn Pro Pro Thr Arg Pro Leu Pro Ala Asp
785                 790                 795                 800
```

```
Pro Val Val Arg Ser Pro Lys Ser Gln Gly Pro Ala Lys Pro Pro Pro
                805                 810                 815

Pro Arg Lys Pro Leu Pro Ala Asp Pro Gln Gly Arg Cys Pro Ser Gly
            820                 825                 830

Asp Leu Pro Gly Pro Gly Ala Gly Ile Pro Pro Leu Val Val Pro Ser
        835                 840                 845

Arg Pro Ala Pro Pro Pro Pro Thr Val Ser Ser Leu Tyr Leu
    850                 855                 860

<210> SEQ ID NO 5
<211> LENGTH: 3360
<212> TYPE: DNA
<213> ORGANISM: Homo sapiens

<400> SEQUENCE: 5
gcggcggcag gcctagcagc acgggaaccg tcccccgcgc gcatgcgcgc gcccctgaag        60
cgcctggggg acgggtaggg gcgggaggta ggggcgcggc tccgcgtgcc agttgggtgc       120
ccgcgcgtca cgtggtgagg aaggaggcgg aggtctgagt tcgaaggag ggggggagag        180 aagagggaac gagcaaggga aggaaagcgg ggaaaggagg aaggaaacga acgagggga        240 gggaggtccc tgttttggag gagctaggag cgttgccggc ccctgaagtg gagcgagagg       300
gaggtgcttc gccgtttctc ctgccagggg aggtcccggc ttcccgtgga ggctccggac       360 caagccccctt cagcttctcc ctccggatcg atgtgctgct gttaacccgt gaggaggcgg      420
cggcggcggc agcggcagcg gaagatggtg ttgctgagag tgttaattct gctcctctcc       480
tgggcggcgg ggatgggagg tcagtatggg aatcctttaa ataaatatat cagacattat       540
gaaggattat cttacaatgt ggattcatta caccaaaaac accagcgtgc caaagagca       600 gtctcacatg aagaccaatt tttacgtcta gatttccatg cccatggaag acatttcaac       660
ctacgaatga gagggacac ttcccttttc agtgatgaat ttaaagtaga acatcaaat        720 aaagtacttg attatgatac ctctcatatt tacactggac atatttatgg tgaagaagga       780
agttttagcc atgggtctgt tattgatgga agatttgaag gattcatcca gactcgtggt       840
ggcacatttt atgttgagcc agcagagaga tatattaaag accgaactct gccatttcac       900
tctgtcattt atcatgaaga tgatattaac tatccccata aatacggtcc tcagggggc       960 tgtgcagatc attcagtatt tgaaagaatg aggaaatacc agatgactgg tgtagaggaa      1020
gtaacacaga tacctcaaga agaacatgct gctaatggtc cagaacttct gaggaaaaaa      1080
cgtacaactt cagctgaaaa aaatacttgt cagctttata ttcagactga tcatttgttc      1140
tttaaatatt acggaacacg agaagctgtg attgcccaga tatccagtca tgttaaagcg      1200
attgatacaa tttaccagac cacagacttc tccggaatcc gtaacatcag tttcatggtg      1260
aaacgcataa gaatcaatac aactgctgat gagaaggacc ctacaaatcc tttccgtttc      1320
ccaaatattg gtgtggagaa gtttctggaa ttgaattctg agcagaatca tgatgactac      1380
tgtttggcct atgtcttcac agaccgagat tttgatgatg cgtacttgg tctggcttgg      1440 gttggagcac cttcaggaag ctctggagga atatgtgaaa aaagtaaact ctattcagat      1500
ggtaagaaga agtccttaaa cactggaatt attactgttc agaactatgg gtctcatgta      1560
cctcccaaag tctctcacat tactttttgct cacgaagttg gacataactt tggatcccca      1620
catgattctg gaacagagtg cacaccagga gaatctaaga atttgggtca aaaagaaaat      1680
ggcaattaca tcatgtatgc aagagcaaca tctggggaca aacttaacaa caataaattc      1740
tcactctgta gtattagaaa tataagccaa gttcttgaga agaagaaa caactgtttt     1800
```

```
gttgaatctg gccaacctat ttgtggaaat ggaatggtag aacaaggtga agaatgtgat    1860
tgtggctata gtgaccagtg taaagatgaa tgctgcttcg atgcaaatca accagaggga    1920
agaaaatgca aactgaaacc tgggaaacag tgcagtccaa gtcaaggtcc ttgttgtaca    1980
gcacagtgtg cattcaagtc aaagtctgag aagtgtcggg atgattcaga ctgtgcaagg    2040
gaaggaatat gtaatggctt cacagctctc tgcccagcat ctgaccctaa accaaacttc    2100
acagactgta ataggcatac acaagtgtgc attaatgggc aatgtgcagg ttctatctgt    2160
gagaaatatg cttagagga gtgtacgtgt gccagttctg atggcaaaga tgataaagaa    2220
ttatgccatg tatgctgtat gaagaaaatg gacccatcaa cttgtgccag tacagggtct    2280
gtgcagtgga gtaggcactt cagtggtcga accatcaccc tgcaacctgg atcccttgc    2340 aacgatttta gaggttactg tgatgttttc atgcggtgca gattagtaga tgctgatggt    2400
cctctagcta ggcttaaaaa agcaattttt agtccagagc tctatgaaaa cattgctgaa    2460
tggattgtgg ctcattggtg ggcagtatta cttatgggaa ttgctctgat catgctaatg    2520
gctggattta ttaagatatg cagtgttcat actccaagta gtaatccaaa gttgcctcct    2580
cctaaaccac ttccaggcac tttaaagagg aggagacctc cacagcccat tcagcaaccc    2640
cagcgtcagc ggccccgaga gagttatcaa atgggacaca tgagacgcta actgcagctt    2700
ttgccttggt tcttcctagt gcctacaatg ggaaaacttc actccaaaga gaaacctatt    2760
aagtcatcat ctccaaacta aaccctcaca agtaacagtt gaagaaaaaa tggcaagaga    2820
tcatatcctc agaccaggtg gaattactta aattttaaag cctgaaaatt ccaatttggg    2880
ggtgggaggt ggaaaaggaa cccaattttc ttatgaacag atattttaa cttaatggca    2940 caaagtctta gaatattatt atgtgccccg tgttccctgt tcttcgttgc tgcatttttct    3000 tcacttgcag gcaaacttgg ctctcaataa acttttacca caaattgaaa taaatatatt    3060 ttttcaact gccaatcaag gctaggaggc tcgaccacct caacattgga gacatcactt    3120
gccaatgtac ataccttgtt atatgcagac atgtatttct tacgtacact gtacttctgt    3180
gtgcaattgt aaacagaaat tgcaatatgg atgtttcttt gtattataaa attttccgc    3240 tcttaattaa aaattactgt ttaattgaca tactcaggat aacagagaat ggtggtattc    3300
agtggtccag gattctgtaa tgctttacac aggcagtttt gaaatgaaaa tcaatttacc    3360
```

<210> SEQ ID NO 6
<211> LENGTH: 748
<212> TYPE: PRT
<213> ORGANISM: Homo sapiens

<400> SEQUENCE: 6

Met Val Leu Leu Arg Val Leu Ile Leu Leu Ser Trp Ala Ala Gly
1               5                   10                  15

Met Gly Gly Gln Tyr Gly Asn Pro Leu Asn Lys Tyr Ile Arg His Tyr
                20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
        50                  55                  60

His Ala His Gly Arg His Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

```
Tyr Asp Thr Ser His Ile Tyr Thr Gly His Ile Tyr Gly Glu Gly
                100                 105                 110

Ser Phe Ser His Gly Ser Val Ile Asp Gly Arg Phe Glu Gly Phe Ile
            115                 120                 125

Gln Thr Arg Gly Gly Thr Phe Tyr Val Glu Pro Ala Glu Arg Tyr Ile
    130                 135                 140

Lys Asp Arg Thr Leu Pro Phe His Ser Val Ile Tyr His Glu Asp Asp
145                 150                 155                 160

Ile Asn Tyr Pro His Lys Tyr Gly Pro Gln Gly Gly Cys Ala Asp His
                165                 170                 175

Ser Val Phe Glu Arg Met Arg Lys Tyr Gln Met Thr Gly Val Glu Glu
            180                 185                 190

Val Thr Gln Ile Pro Gln Glu Glu His Ala Ala Asn Gly Pro Glu Leu
    195                 200                 205

Leu Arg Lys Lys Arg Thr Thr Ser Ala Glu Lys Asn Thr Cys Gln Leu
210                 215                 220

Tyr Ile Gln Thr Asp His Leu Phe Phe Lys Tyr Tyr Gly Thr Arg Glu
225                 230                 235                 240

Ala Val Ile Ala Gln Ile Ser Ser His Val Lys Ala Ile Asp Thr Ile
                245                 250                 255

Tyr Gln Thr Thr Asp Phe Ser Gly Ile Arg Asn Ile Ser Phe Met Val
            260                 265                 270

Lys Arg Ile Arg Ile Asn Thr Thr Ala Asp Glu Lys Asp Pro Thr Asn
    275                 280                 285

Pro Phe Arg Phe Pro Asn Ile Gly Val Glu Lys Phe Leu Glu Leu Asn
290                 295                 300

Ser Glu Gln Asn His Asp Asp Tyr Cys Leu Ala Tyr Val Phe Thr Asp
305                 310                 315                 320

Arg Asp Phe Asp Asp Gly Val Leu Gly Leu Ala Trp Val Gly Ala Pro
                325                 330                 335

Ser Gly Ser Ser Gly Gly Ile Cys Glu Lys Ser Lys Leu Tyr Ser Asp
            340                 345                 350

Gly Lys Lys Lys Ser Leu Asn Thr Gly Ile Ile Thr Val Gln Asn Tyr
    355                 360                 365

Gly Ser His Val Pro Pro Lys Val Ser His Ile Thr Phe Ala His Glu
370                 375                 380

Val Gly His Asn Phe Gly Ser Pro His Asp Ser Gly Thr Glu Cys Thr
385                 390                 395                 400

Pro Gly Glu Ser Lys Asn Leu Gly Gln Lys Glu Asn Gly Asn Tyr Ile
                405                 410                 415

Met Tyr Ala Arg Ala Thr Ser Gly Asp Lys Leu Asn Asn Asn Lys Phe
            420                 425                 430

Ser Leu Cys Ser Ile Arg Asn Ile Ser Gln Val Leu Glu Lys Lys Arg
    435                 440                 445

Asn Asn Cys Phe Val Glu Ser Gly Gln Pro Ile Cys Gly Asn Gly Met
450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
                485                 490                 495

Leu Lys Pro Gly Lys Gln Cys Ser Pro Ser Gln Gly Pro Cys Cys Thr
            500                 505                 510

Ala Gln Cys Ala Phe Lys Ser Lys Ser Glu Lys Cys Arg Asp Asp Ser
```

-continued

```
            515                 520                 525
Asp Cys Ala Arg Glu Gly Ile Cys Asn Gly Phe Thr Ala Leu Cys Pro
            530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
                565                 570                 575

Leu Glu Glu Cys Thr Cys Ala Ser Ser Asp Gly Lys Asp Asp Lys Glu
            580                 585                 590

Leu Cys His Val Cys Cys Met Lys Lys Met Asp Pro Ser Thr Cys Ala
            595                 600                 605

Ser Thr Gly Ser Val Gln Trp Ser Arg His Phe Ser Gly Arg Thr Ile
            610                 615                 620

Thr Leu Gln Pro Gly Ser Pro Cys Asn Asp Phe Arg Gly Tyr Cys Asp
625                 630                 635                 640

Val Phe Met Arg Cys Arg Leu Val Asp Ala Asp Gly Pro Leu Ala Arg
                645                 650                 655

Leu Lys Lys Ala Ile Phe Ser Pro Glu Leu Tyr Glu Asn Ile Ala Glu
            660                 665                 670

Trp Ile Val Ala His Trp Trp Ala Val Leu Leu Met Gly Ile Ala Leu
            675                 680                 685

Ile Met Leu Met Ala Gly Phe Ile Lys Ile Cys Ser Val His Thr Pro
690                 695                 700

Ser Ser Asn Pro Lys Leu Pro Pro Pro Lys Pro Leu Pro Gly Thr Leu
705                 710                 715                 720

Lys Arg Arg Arg Pro Pro Gln Pro Ile Gln Gln Pro Gln Arg Gln Arg
                725                 730                 735

Pro Arg Glu Ser Tyr Gln Met Gly His Met Arg Arg
            740                 745

<210> SEQ ID NO 7
<211> LENGTH: 19
<212> TYPE: DNA
<213> ORGANISM: Artificial sequence
<220> FEATURE:
<223> OTHER INFORMATION: oligonucleotide sequence corr. to (1272-1300)
      of ADAM10

<400> SEQUENCE: 7
ggacaaactt aacaacaat                                                19

<210> SEQ ID NO 8
<211> LENGTH: 19
<212> TYPE: DNA
<213> ORGANISM: Artificial sequence
<220> FEATURE:
<223> OTHER INFORMATION: oligonucleotide sequence corr. to (281-199) of
      ADAM15

<400> SEQUENCE: 8
gcccaaccct ggtgtggta                                                19

<210> SEQ ID NO 9
<211> LENGTH: 19
<212> TYPE: DNA
<213> ORGANISM: Artificial sequence
<220> FEATURE:
<223> OTHER INFORMATION: forward primer sequence

<400> SEQUENCE: 9
```

```
tgctcctccg gtcactgtg                                          19

<210> SEQ ID NO 10
<211> LENGTH: 23
<212> TYPE: DNA
<213> ORGANISM: Artificial sequence
<220> FEATURE:
<223> OTHER INFORMATION: forward primer sequence

<400> SEQUENCE: 10
tgtcaagtca tctttggctc aaa                                     23

<210> SEQ ID NO 11
<211> LENGTH: 22
<212> TYPE: DNA
<213> ORGANISM: Artificial sequence
<220> FEATURE:
<223> OTHER INFORMATION: forward primer sequence

<400> SEQUENCE: 11
tccaaagttg cctcctccta aa                                      22

<210> SEQ ID NO 12
<211> LENGTH: 19
<212> TYPE: DNA
<213> ORGANISM: Artificial sequence
<220> FEATURE:
<223> OTHER INFORMATION: forward primer sequence

<400> SEQUENCE: 12
atgaggaagc cgccagatt                                          19

<210> SEQ ID NO 13
<211> LENGTH: 22
<212> TYPE: DNA
<213> ORGANISM: Artificial sequence
<220> FEATURE:
<223> OTHER INFORMATION: forward primer sequence

<400> SEQUENCE: 13
acaggcactg ctactgtgag ga                                      22

<210> SEQ ID NO 14
<211> LENGTH: 19
<212> TYPE: DNA
<213> ORGANISM: Artificial sequence
<220> FEATURE:
<223> OTHER INFORMATION: forward primer sequence

<400> SEQUENCE: 14
gcatggattc tgcatcggt                                          19

<210> SEQ ID NO 15
<211> LENGTH: 27
<212> TYPE: DNA
<213> ORGANISM: Artificial sequence
<220> FEATURE:
<223> OTHER INFORMATION: forward primer sequence

<400> SEQUENCE: 15
tctcaaatag agaggacgga gtcgtcc                                 27

<210> SEQ ID NO 16
<211> LENGTH: 21
<212> TYPE: DNA
```

```
<213> ORGANISM: Artificial sequence
<220> FEATURE:
<223> OTHER INFORMATION: forward primer sequence

<400> SEQUENCE: 16
tgcaaggaca aaggctatgg a                                              21

<210> SEQ ID NO 17
<211> LENGTH: 25
<212> TYPE: DNA
<213> ORGANISM: Artificial sequence
<220> FEATURE:
<223> OTHER INFORMATION: forward primer sequence

<400> SEQUENCE: 17
aagtgaaaga tggtactgtg tgtgg                                          25

<210> SEQ ID NO 18
<211> LENGTH: 23
<212> TYPE: DNA
<213> ORGANISM: Artificial sequence
<220> FEATURE:
<223> OTHER INFORMATION: forward primer sequence

<400> SEQUENCE: 18
gatgactcct cagtggtctt cca                                            23

<210> SEQ ID NO 19
<211> LENGTH: 19
<212> TYPE: DNA
<213> ORGANISM: Artificial sequence
<220> FEATURE:
<223> OTHER INFORMATION: forward primer sequence

<400> SEQUENCE: 19
ccatttgtgg cccaagaga                                                 19

<210> SEQ ID NO 20
<211> LENGTH: 17
<212> TYPE: DNA
<213> ORGANISM: Artificial sequence
<220> FEATURE:
<223> OTHER INFORMATION: forward primer sequence

<400> SEQUENCE: 20
ctcgcaccgc acatggt                                                   17

<210> SEQ ID NO 21
<211> LENGTH: 21
<212> TYPE: DNA
<213> ORGANISM: Artificial sequence
<220> FEATURE:
<223> OTHER INFORMATION: reverse primer sequence

<400> SEQUENCE: 21
ttggcttgat gacctgcttt g                                              21

<210> SEQ ID NO 22
<211> LENGTH: 28
<212> TYPE: DNA
<213> ORGANISM: Artificial sequence
<220> FEATURE:
<223> OTHER INFORMATION: reverse primer sequence

<400> SEQUENCE: 22
aaatctgtca cctttagaat tcacttca                                       28
```

```
<210> SEQ ID NO 23
<211> LENGTH: 15
<212> TYPE: DNA
<213> ORGANISM: Artificial sequence
<220> FEATURE:
<223> OTHER INFORMATION: reverse primer sequence

<400> SEQUENCE: 23
gggccgctga cgctg                                                      15

<210> SEQ ID NO 24
<211> LENGTH: 22
<212> TYPE: DNA
<213> ORGANISM: Artificial sequence
<220> FEATURE:
<223> OTHER INFORMATION: reverse primer sequence

<400> SEQUENCE: 24
caacattctg acactgcagc aa                                              22

<210> SEQ ID NO 25
<211> LENGTH: 19
<212> TYPE: DNA
<213> ORGANISM: Artificial sequence
<220> FEATURE:
<223> OTHER INFORMATION: reverse primer sequence

<400> SEQUENCE: 25
ccaagcatca ccaggacca                                                  19

<210> SEQ ID NO 26
<211> LENGTH: 14
<212> TYPE: DNA
<213> ORGANISM: Artificial sequence
<220> FEATURE:
<223> OTHER INFORMATION: reverse primer sequence

<400> SEQUENCE: 26
tgcaggcggc ctgg                                                       14

<210> SEQ ID NO 27
<211> LENGTH: 20
<212> TYPE: DNA
<213> ORGANISM: Artificial sequence
<220> FEATURE:
<223> OTHER INFORMATION: reverse primer sequence

<400> SEQUENCE: 27
gggaaacgat gcaatttggt                                                 20

<210> SEQ ID NO 28
<211> LENGTH: 24
<212> TYPE: DNA
<213> ORGANISM: Artificial sequence
<220> FEATURE:
<223> OTHER INFORMATION: reverse primer sequence

<400> SEQUENCE: 28
tttcccatca catttaatcc ttcc                                            24

<210> SEQ ID NO 29
<211> LENGTH: 22
<212> TYPE: DNA
<213> ORGANISM: Artificial sequence
<220> FEATURE:
```

<223> OTHER INFORMATION: reverse primer sequence

<400> SEQUENCE: 29
caggtctcag gaaggcagac at                                              22

<210> SEQ ID NO 30
<211> LENGTH: 20
<212> TYPE: DNA
<213> ORGANISM: Artificial sequence
<220> FEATURE:
<223> OTHER INFORMATION: reverse primer sequence

<400> SEQUENCE: 30
ggtgccggat taccatagca                                                 20

<210> SEQ ID NO 31
<211> LENGTH: 21
<212> TYPE: DNA
<213> ORGANISM: Artificial sequence
<220> FEATURE:
<223> OTHER INFORMATION: reverse primer sequence

<400> SEQUENCE: 31
gcagttcccc atgttctgtg a                                               21

<210> SEQ ID NO 32
<211> LENGTH: 20
<212> TYPE: DNA
<213> ORGANISM: Artificial sequence
<220> FEATURE:
<223> OTHER INFORMATION: reverse primer sequence

<400> SEQUENCE: 32
gctccccgac aagtcacttc                                                 20

<210> SEQ ID NO 33
<211> LENGTH: 27
<212> TYPE: DNA
<213> ORGANISM: Artificial sequence
<220> FEATURE:
<223> OTHER INFORMATION: probe sequence

<400> SEQUENCE: 33
cccacccttc ccagttcctg tctacac                                         27

<210> SEQ ID NO 34
<211> LENGTH: 25
<212> TYPE: DNA
<213> ORGANISM: Artificial sequence
<220> FEATURE:
<223> OTHER INFORMATION: probe sequence

<400> SEQUENCE: 34
caaggctgcc cccaaagatt gtttc                                           25

<210> SEQ ID NO 35
<211> LENGTH: 26
<212> TYPE: DNA
<213> ORGANISM: Artificial sequence
<220> FEATURE:
<223> OTHER INFORMATION: probe sequence

<400> SEQUENCE: 35
agacctccac agcccattca gcaacc                                          26

```
<210> SEQ ID NO 36
<211> LENGTH: 25
<212> TYPE: DNA
<213> ORGANISM: Artificial sequence
<220> FEATURE:
<223> OTHER INFORMATION: probe sequence

<400> SEQUENCE: 36
ctacccaccg aaggacaatc ccagg                                          25

<210> SEQ ID NO 37
<211> LENGTH: 25
<212> TYPE: DNA
<213> ORGANISM: Artificial sequence
<220> FEATURE:
<223> OTHER INFORMATION: probe sequence

<400> SEQUENCE: 37
tcaaagcaac cagctccctg accac                                          25

<210> SEQ ID NO 38
<211> LENGTH: 22
<212> TYPE: DNA
<213> ORGANISM: Artificial sequence
<220> FEATURE:
<223> OTHER INFORMATION: probe sequence

<400> SEQUENCE: 38 aaacccttc ctgcgcccca ga                                              22

<210> SEQ ID NO 39
<211> LENGTH: 20
<212> TYPE: DNA
<213> ORGANISM: Artificial sequence
<220> FEATURE:
<223> OTHER INFORMATION: probe sequence

<400> SEQUENCE: 39
tccaagccgg ccaattcccc                                                20

<210> SEQ ID NO 40
<211> LENGTH: 32
<212> TYPE: DNA
<213> ORGANISM: Artificial sequence
<220> FEATURE:
<223> OTHER INFORMATION: probe sequence

<400> SEQUENCE: 40
tagtgctgat agtggcccac ctcctaagaa ca                                  32

<210> SEQ ID NO 41
<211> LENGTH: 34
<212> TYPE: DNA
<213> ORGANISM: Artificial sequence
<220> FEATURE:
<223> OTHER INFORMATION: probe sequence

<400> SEQUENCE: 41
caggaaagat ctgcatccat aagaagtgtg tcag                                34

<210> SEQ ID NO 42
<211> LENGTH: 26
<212> TYPE: DNA
<213> ORGANISM: Artificial sequence
<220> FEATURE:
<223> OTHER INFORMATION: probe sequence
```

```
<400> SEQUENCE: 42
ctgttcccaa tggcggtcat ttttgt                                        26

<210> SEQ ID NO 43
<211> LENGTH: 21
<212> TYPE: DNA
<213> ORGANISM: Artificial sequence
<220> FEATURE:
<223> OTHER INFORMATION: probe sequence

<400> SEQUENCE: 43
ctgttgcccg gacatctgcg c                                             21

<210> SEQ ID NO 44
<211> LENGTH: 25
<212> TYPE: DNA
<213> ORGANISM: Artificial sequence
<220> FEATURE:
<223> OTHER INFORMATION: probe sequence

<400> SEQUENCE: 44
actctaccgt tcacctagat ggcca                                         25

<210> SEQ ID NO 45
<211> LENGTH: 12
<212> TYPE: PRT
<213> ORGANISM: Artificial sequence
<220> FEATURE:
<223> OTHER INFORMATION: metalloproteinase active site for ADAM family
<220> FEATURE:
<221> NAME/KEY: MISC_FEATURE
<222> LOCATION: (3)..(3)
<223> OTHER INFORMATION: Xaa is any amino acid.
<220> FEATURE:
<221> NAME/KEY: MISC_FEATURE
<222> LOCATION: (6)..(7)
<223> OTHER INFORMATION: Xaa is any amino acid.
<220> FEATURE:
<221> NAME/KEY: MISC_FEATURE
<222> LOCATION: (9)..(10)
<223> OTHER INFORMATION: Xaa is any amino acid.

<400> SEQUENCE: 45

His Glu Xaa Gly His Xaa Xaa Gly Xaa Xaa His Asp
1               5                   10

<210> SEQ ID NO 46
<211> LENGTH: 6
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: (7-methoxycoumarin-4-yl) acetyl-Proline
<220> FEATURE:
<221> NAME/KEY: MOD_RES
<222> LOCATION: (5)..(5)
<223> OTHER INFORMATION: (3-[2,4-dintrophenyl]-L-2,3-diaminoprpionyl)-
      Alanine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: AMIDATION

<400> SEQUENCE: 46
```

```
Xaa Leu Gly Leu Xaa Arg
1               5

<210> SEQ ID NO 47
<211> LENGTH: 10
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: (7-methoxycoumarin-4-yl) acetyl-Arginine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: Nva
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MOD_RES
<222> LOCATION: (10)..(10)
<223> OTHER INFORMATION: (2,4)-dintrophenyl Lysine-amide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 47

Xaa Pro Lys Pro Val Glu Xaa Trp Arg Xaa
1               5                   10

<210> SEQ ID NO 48
<211> LENGTH: 11
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (1)..(1)
<223> OTHER INFORMATION: (7-methoxycoumarin-4-yl)-acetyl Proline
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (7)..(7)
<223> OTHER INFORMATION: (3-[2,4-dinitrophenyl]-L-2,3-diaminopropionyl-
     Arginine
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MOD_RES
<222> LOCATION: (11)..(11)
<223> OTHER INFORMATION: AMIDATION

<400> SEQUENCE: 48

Xaa Leu Ala Gln Ala Val Xaa Ser Ser Ser Arg
1               5                   10
```

COMPOSITIONS, METHODS AND KITS RELATING TO HER-2 CLEAVAGE

CROSS-REFERENCE TO RELATED APPLICATIONS

This application is a continuation of U.S. Ser. No. 10/817,718, filed Apr. 2, 2004 now U.S. Pat. No. 8,088,737, which claims priority to U.S. Ser. Nos. 60/460,678, filed Apr. 4, 2003; 60/472,494, filed May 22, 2003; 60/532,030, filed Dec. 22, 2003; and 60/548,986, filed Mar. 1, 2004, the disclosures of each of which are incorporated herein by reference in their entireties.

FIELD OF THE INVENTION

The present invention relates to compositions, methods and kits based on the ADAM-mediated cleavage of Her-2. The present invention also relates to treatments for cancer, and in particular, breast cancer, by modulating the ADAM-mediated cleavage of Her-2. Further, the invention relates to compositions, methods and kits based on the surprising synergistic effect between inhibition of Her-2 cleavage by an ADAM and certain cytostatic (e.g., Herceptin) and cytotoxic (e.g., Taxol) compounds in, among other things, inhibiting tumor cell proliferation and inducing cell death. Additionally, the invention relates to novel variants of ADAM15, designated ADAM15 variant 1 and ADAM15 variant 2, now identified and isolated.

BACKGROUND OF THE INVENTION

The HER-2/neu (erbB-2) oncogene encodes a receptor tyrosine kinase (RTK) that has been extensively investigated because of its role in several human carcinomas (Hynes and Stern, 1994, Biochim. et Biophys. Acta 1198:165-184; and Dougall et al., 1994, Oncogene 9:2109-2123) and in mammalian development (Lee et al., 1995, Nature 378:394-398). Her-2 (also referred to as "erbB2," "p185" or "c-neu") is a 185 kDa member of the epidermal growth factor (EGF) receptor tyrosine kinase family. The sequence of the Her-2 protein was determined from a cDNA that was cloned by homology to the epidermal growth factor receptor (EGFR) mRNA from placenta (Coussens et al. 1985, Science 230:1132-1139) and from a gastric carcinoma cell line (Yamamoto et al., 1986, Nature 319:230-234). The full-length HER-2 mRNA encodes a transmembrane glycoprotein of 185 kDa in normal and malignant human tissues (p185HER-2) (Hynes and Steen, 1994, Biochim. et Biophys. Acta 1198:165-184; and Dougall et al., 1994, Oncogene 9:2109-2123).

The function of the HER-2 gene has been examined mainly by expressing the cDNA corresponding to the 4.5 kb transcript in transfected cells and from the structure and biochemical properties of the 185 kDa protein product. P185HER-2 consists of a large extracellular domain, a transmembrane segment, and an intracellular domain with tyrosine kinase activity (Hynes and Stern, 1994, Biochim. et Biophys. Acta 1198:165-184; and Dougall et al., 1994, Oncogene 9:2109-2123). Overexpression of p185HER-2 causes phenotypic transformation of cultured cells (DiFiore et al., 1987, Science 237:178-182; and Hudziak et al., 1987, Proc. Natl. Acad. Sci. USA 84:7159-7163) and has been associated with aggressive clinical progression of breast and ovarian cancer (Slamon et al., 1987, Science 235:177-182; and Slamon et al., 1989, Science 244:707-712).

p185HER-2 is highly homologous to the EGFR. However, a ligand that directly binds with high affinity to p185HER-2 has not yet been identified. Moreover, the signaling activity of HER-2 may be mediated through heterodimerization with other ligand-binding members of the EGFR family (Carraway and Cantley, Cell 78:5-8, 1994; Earp et al., 1995, Breast Cancer Res. Treat. 35:115-132; and Qian et al., 1995, Oncogene 10:211-219).

Divergent proteins, containing regions of the extracellular domains of HER family RTKs, are generated through proteolytic processing of full length receptors (Lin and Clinton, 1991, Oncogene 6:639-643; Zabrecky et al., 1991, J. Biol. Chem. 266:1716-1720; Pupa et al., 1993, Oncogene 8:2917-2923; Vecchi et al., 1996, J. Biol. Chem. 271:18989-18995; and Vecchi and Carpenter, 1997, J. Cell Biol. 139:995-1003) and through alternative RNA processing (Petch et al., 1990, Mol. Cell. Biol. 10:2973-2982; Scott et al., 1993, Mol. Cell. Biol. 13:2247-2257; and Lee and Maihle, 1998, Oncogene 16:3243-3252).

The extracellular domain of p185HER-2 (hereinafter referred to as "ECD") is proteolytically shed from breast carcinoma cells in culture (Petch et al., 1990, Mol. Cell. Biol. 10:2973-2982; Scott et al., 1993, Mol. Cell. Biol. 13:2247-2257; and Lee and Maihle, 1998, Oncogene 16:3243-3252), and is found in the serum of some cancer patients (Leitzel et al., 1992, J. Clin. Oncol. 10:1436-1443) where it is may be a serum marker of metastatic breast cancer (Leitzel et al., 1992, J. Clin. Oncol. 10:1436-1443) and may allow escape of HER-2-rich tumors from immunological control (Baselga et al., 1997, J. Clin. Oncol. 14:737-744, Brodowicz et al., 1997, Int. J. Cancer 73:875-879). While shed Her-2 ECD serum levels correlate with tumor mass, additional studies have demonstrated that shed Her-2 ECD serum levels represent an independent marker of poor clinical outcome in patients with Her-2 overexpressing metastatic breast cancer (Ali et al., 2002, Clin. Chem. 48:1314-1320; Molina et al., 2002, Clin. Cancer Res. 8:347-353).

A truncated extracellular domain of HER-2 is also the product of a 2.3 kb alternative transcript generated by use of a polyadenylation signal within an intron (Scott et al., 1993, Mol. Cell. Biol. 13:2247-2257). The alternative transcript was first identified in the gastric carcinoma cell line, MKN7 (Yamamoto et al., 1986, Nature 319:230-234; and Scott et al., 1993, Mol. Cell. Biol. 13:2247-2257) and the truncated receptor was located within the perinuclear cytoplasm rather than secreted from these tumor cells (Scott et al., 1993, Mol. Cell. Biol. 13:2247-2257). However, no particular therapeutic, diagnostic or research utility has been ascribed to this truncated extracellular domain polypeptide. A truncated extracellular domain of the EGFR, generated by alternative splicing (Petch et al., 1990, Mol. Cell. Biol. 10:2973-2982) is secreted, exhibits ligand-binding as well as dimerization properties (Basu et al., 1989, Mol. Cell. Biol. 9:671-677), and may have a dominant negative effect on receptor function (Basu et al., 1989, Mol. Cell. Biol. 9:671-677; and Flickinger et al., 1992, Mol. Cell. Biol. 12:883-893).

An additional alternatively spliced product of Her-2, designated herstatin, has also been identified (Doherty et al., 1999, Proc. Natl. Acad. Sci. 96:10869-10874; Azios et al., 2001, Oncogene 20:5199-5209; Justman and Clinton, 2002, J. Biol. Chem. 277:20618-20624). This protein consists of subdomains I and II from the extracellular domain followed by a unique C-terminal sequence encoded by intron 8. Herstatin is secreted and binds with nanomolar affinity to EGFR family members. It appears to function as an autoinhibitor by disrupting receptor dimerization and receptor phosphorylation, resulting in inhibition of AKT signaling and suppression of proliferation in EGFR or Her-2 overexpressing cells. Herstatin was shown to be present at reduced levels in Her-2 overexpressing tumor cells, suggesting that if Herstatin plays a role in regulating normal cell growth, this is circumvented in tumor cells.

Signaling by the EGF family of receptors is initiated by ligand binding which triggers homo- or hetero-receptor dimerization, reciprocal tyrosine phosphorylation of the cytoplasmic tails, and activation of intracellular signal transduction pathways. The biologic consequence of EGF receptor signaling is frequently associated with cellular differentiation, growth or survival.

Overexpression of Her-2 occurs in 25-30% of breast cancers. Patients with Her-2 overexpressing tumors have a distinctly unfavorable clinical course, characterized by shortened time to disease recurrence and reduced survival. The precise mechanisms responsible for this association are not established. In this regard, it has been suggested that the overexpressed Her-2 receptor can more readily heterodimerize with other EGF receptor family members that have bound ligands, thereby initiating intracellular signaling cascades leading to growth and resistance to apoptosis. Alternatively, the high copy number of Her-2 receptors on the tumor cell surface can promote ligand independent receptor homodimerization, and intracellular signaling leading to tumor cell growth and survival.

Another mechanism that may account for poor clinical outcome in Her-2 overexpressing tumors is suggested by the observation that, in some Her-2 overexpressing tumor cells, the receptor is processed by an unknown metalloprotease (or metalloproteinase) to yield a truncated, membrane-associated receptor (sometimes referred to as a "stub" and also known as p95), and a soluble extracellular domain (also known as ECD, ECD105, or p105).

As with other EGF receptor family members, loss of the extracellular ligand binding domain renders the Her-2 intracellular membrane-associated domain a constitutively active tyrosine kinase. It has therefore been postulated that the processing of the Her-2 extracellular domain creates a constitutively active receptor that can directly deliver growth and survival signals to the cancer cell. In this regard, it has been shown that an engineered version of Her-2, lacking the extracellular domain, is 10-100 fold more efficient than the full length receptor in cellular transformation assays.

Moreover, the truncated form of Her-2 receptor (p95) has been shown to interact with and potently activate signaling through the EGF receptor (also referred to as "Her-1"). Most compelling, immunohistochemical analysis of clinical breast cancer specimens strongly suggest that poor clinical outcome is more closely associated with the presence of the truncated Her-2 receptor (p95) rather than the intact receptor (p185) in the tumor cell as discussed by Clinton (U.S. Pat. No. 6,541, 214).

The ADAM (A Disintegrin And Metalloprotease) family of proteases has been demonstrated to catalyze cell surface ecto domain shedding of specific proteins (Moss and Lambert, 2002, Essays in Biochemistry 38:141-153; Chang and Werb, 2001, Trends in Cell Biology 11:537-543, Seals and Courtneidge, 2003, Genes and Development 17:7-30). The domain structure of ADAM family members places the protease catalytic domain of these type I membrane proteins extracellularly. From the amino terminus of the protein, the domains include a pro domain, catalytic domain, disintegrin domain, cysteine rich region and EGF repeat followed by the transmembrane domain and cytoplasmic tail. The pro domain is processed to form the mature proteolytically active form. The disintegrin domain may be involved in adhesion or substrate recognition and binding.

ADAM 10 was the first ADAM family member shown to have proteolytic activity. It has been demonstrated to cleave proteins such as APP and Notch as well as other cell surface proteins. Of interest, substrates for ADAM 10 include HB-EGF, a member of the epidermal growth factor family, which is important in cell transformation and mitogenesis. Cleavage of the extracellular domain of HB-EGF leads to the generation of a soluble fragment of HB-EGF that binds to and activates the EGF receptor. ADAM 15 has also been demonstrated to be an active protease and has been shown to degrade both type IV collagen and gelatin. In addition, ADAM 15 has been shown to actively participate in binding to integrins, including alpha5beta and alphavbeta3, through its disintegrin domain.

In Her-2 overexpressing cells, Her-2 had been found to undergo cleavage to form p95 in the presence of 4-aminophenylmercuric acetate (APMA), a well-known metalloprotease activator (Molina et al., 2001, Cancer Res. 61:4744-4749). APMA-mediated cleavage of Her-2 to form p95 was found to be inhibited in the same cells in the presence of batimastat, a broad-spectrum metalloprotease inhibitor. Additionally, Herceptin™ (also referred to as trastuzumab), an anti-Her-2 monoclonal antibody that has shown clinical efficacy in Her-2 overexpressing breast cancer, has been shown to inhibit enzymatic cleavage of intact Her-2 (p185) into an ECD portion and the p95 constitutively active kinase membrane-associated portion in vitro. It has been suggested that this cleavage-inhibitory effect of Herceptin™ may be mediated by antibody binding near the enzymatic clip site thereby interfering with cleavage enzyme-substrate interaction via steric hindrance. However, the mechanism by which Herceptin acts in the body (e.g., in vivo) remains unclear. Studies have shown that Herceptin appears to have multiple cellular functions that serve to inhibit Her-2 oncogenic signaling through different mechanisms (see, e.g., Baselga, et al., Seminars in Oncology, 2001, 28(5), suppl. 16, pp 4-11 and Baselga et al., Annals of Oncology, 2001, 12, suppl. 1, pp S35-S41). While some studies propose that at least one of the mechanisms of action of Herceptin is related to inhibition of Her-2 shedding, other studies, in fact, show that shedding continues to occur in patients treated with the antibody (Pegram et al., Journal of Clinical Oncology, 1998, 16(8), 2659-2671).

Despite the prevalence, morbidity and mortality associated with breast cancer, and other Her-2 overexpressing malignancies, there are few, if any, effective therapies for these diseases and disorders. Thus, there is an acute need for treatments and therapeutics for Her-2 overexpressing breast, and other, cancers, and the present invention meets this and other needs.

SUMMARY OF THE INVENTION

The present invention provides methods of treating cancer in a patient, wherein the cancer overexpresses Her-2, comprising administering to the patient a therapeutically effective amount of an ADAM inhibitor.

The present invention further provides methods of treating cancer in a patient, wherein the cancer overexpresses Her-2, comprising inhibiting cleavage of Her-2 expressed in the cancer.

The present invention further provides methods of treating cancer in a patient, comprising inhibiting formation of p95.

The present invention further provides methods of treating cancer in a patient, wherein the cancer overexpresses Her-2 and the cancer expresses an ADAM that cleaves the Her-2, the method comprising inhibiting the Her-2 cleaving activity of the ADAM in the patient.

The present invention further provides methods of inhibiting metastasis of cancer in a patient comprising administering to the patient a therapeutically effective amount of an ADAM inhibitor.

The present invention further provides methods of inhibiting metastasis of cancer in a patient comprising inhibiting cleavage of Her-2 expressed in the cancer.

The present invention further provides methods of inhibiting metastasis of cancer in a patient, wherein the cancer overexpresses Her-2 and the cancer expresses an ADAM that cleaves the Her-2, comprising inhibiting the Her-2 cleaving activity of the ADAM in the patient.

The present invention further provides methods of inhibiting growth of a tumor in a patient, comprising administering to the patient a therapeutically effective amount of an ADAM inhibitor.

The present invention further provides methods of inhibiting growth of a tumor in a patient comprising inhibiting cleavage of Her-2 expressed in the tumor.

The present invention further provides methods of inhibiting growth of a tumor in a patient, wherein the tumor overexpresses Her-2 and the tumor expresses an ADAM that cleaves the Her-2, comprising inhibiting the Her-2 cleaving activity of the ADAM in the patient.

The present invention further provides an isolated nucleic acid encoding a mammalian ADAM15 variant and compositions thereof.

The present invention further provides an isolated mammalian ADAM15 variant polypeptide and compositions thereof.

The present invention further provides methods of inhibiting cleavage of Her-2 in a cell, the method comprising contacting a Her-2 expressing cell with a Her-2 cleavage-inhibiting amount of an ADAM inhibitor, thereby inhibiting cleavage of the Her-2 in the cell.

The present invention further provides methods of inhibiting cleavage of Her-2 to produce p95-Her-2, the method comprising contacting an ADAM with a cleavage-inhibiting amount of an ADAM inhibitor, thereby inhibiting cleavage of Her-2 to produce p95-Her-2.

The present invention further provides methods of inhibiting cleavage of Her-2 in a cell, the method comprising contacting a Her-2 overexpressing cell with an isolated nucleic acid complementary to an isolated nucleic acid encoding a mammalian ADAM selected from the group consisting of ADAM10 and ADAM15, or a fragment thereof, the complementary nucleic acid being in an antisense orientation, thereby inhibiting cleavage of the Her-2 in the cell.

The present invention further provides methods of inhibiting cleavage of Her-2 in a cell, the method comprising contacting a Her-2 overexpressing cell with a Her-2 synergistic cleavage-inhibiting amount of a metalloprotease inhibitor (MPI), wherein the MPI inhibits the activity of a mammalian ADAM selected from the group consisting of ADAM10 and ADAM15, and further contacting the cell with a Her-2 synergistic cleavage-inhibiting amount of a Her-2 antagonistic antibody, thereby inhibiting cleavage of the Her-2 in the cell.

The present invention further provides methods of inhibiting release of an extracellular domain (ECD) from a Her-2 on a Her-2 overexpressing cell, the method comprising contacting a Her-2 overexpressing cell with a Her-2 synergistic cleavage-inhibiting amount of an MPI, wherein the MPI inhibits the activity of a mammalian ADAM, and further contacting the cell with a Her-2 synergistic cleavage-inhibiting amount of a Her-2 antagonistic antibody, thereby inhibiting release of the ECD from the Her-2 on the cell.

The present invention further provides methods of inhibiting release of an extracellular domain (ECD) from a Her-2 on a Her-2 overexpressing cell, the method comprising contacting a Her-2 overexpressing cell with a Her-2 synergistic cleavage-inhibiting amount of an MPI, wherein the MPI inhibits the activity of a mammalian ADAM selected from the group consisting of ADAM10 and ADAM15, and further contacting the cell with a Her-2 synergistic cleavage-inhibiting amount of a Her-2 antagonistic antibody, thereby inhibiting release of the ECD from the Her-2 on the cell.

The present invention further provides methods of inhibiting Her-2 interaction with a mammalian ADAM, the method comprising contacting a mixture comprising Her-2 and a mammalian ADAM with an agent that specifically binds with Her-2, wherein the ADAM is selected from the group consisting of ADAM10 and ADAM15.

The present invention further provides methods of inhibiting interaction of a mammalian ADAM with a Her-2 on a cell, the method comprising contacting a Her-2 overexpressing cell with an agent that specifically binds with Her-2, thereby inhibiting the interaction of the ADAM with the Her-2 on the cell.

The present invention further provides methods of inhibiting formation of p95 on a Her-2 expressing cell, the method comprising contacting a Her-2 overexpressing cell with a Her-2 cleavage-inhibiting amount of an inhibitor of a mammalian ADAM, thereby inhibiting formation of the p95 on the cell.

The present invention further provides methods of inhibiting release of an extracellular domain (ECD) portion from a Her-2 on a Her-2 overexpressing cell, the method comprising contacting a Her-2 overexpressing cell with a Her-2 cleavage-inhibiting amount of an ADAM inhibitor, thereby inhibiting release of the ECD from the Her-2 on the cell.

The present invention further provides methods of inhibiting formation of p95 on a Her-2 overexpressing cell, the method comprising contacting a Her-2 expressing cell with a Her-2 synergistic cleavage-inhibiting amount of an MPI, wherein the MPI inhibits the activity of a mammalian ADAM, and further contacting the cell with a Her-2 synergistic cleavage-inhibiting amount of a Her-2 antagonistic antibody, thereby inhibiting formation of the p95 on the cell.

The present invention further provides methods of inhibiting growth of a Her-2 overexpressing cell, the method comprising contacting a Her-2 overexpressing cell with a Her-2 cleavage-inhibiting amount of an ADAM inhibitor, thereby inhibiting growth of the Her-2 overexpressing cell.

The present invention further provides methods of inhibiting proliferation of a Her-2 overexpressing cell, the method comprising contacting a Her-2 overexpressing cell with a Her-2 cleavage-inhibiting amount of an ADAM inhibitor, thereby inhibiting proliferation of the Her-2 overexpressing cell.

The present invention further provides methods of inducing death of a Her-2 overexpressing cell, the method comprising contacting a Her-2 overexpressing cell with a Her-2 cleavage-inhibiting amount of an ADAM inhibitor, thereby inducing death of the Her-2 overexpressing cell.

The present invention further provides methods of inhibiting growth of a tumor cell overexpressing Her-2, the method comprising contacting the tumor cell with a Her-2 cleavage-inhibiting amount of an inhibitor of ADAM, thereby inhibiting cleavage of the Her-2 polypeptide thereby inhibiting growth of the tumor cell overexpressing Her-2.

The present invention further provides methods of inhibiting a signal transduction mediated via a Her-2 receptor on a Her-2 overexpressing cell, the method comprising contacting a Her-2 overexpressing cell with a Her-2 cleavage-inhibiting amount of an ADAM inhibitor, thereby inhibiting cleavage of the Her-2, thereby inhibiting the signal transduction mediated via a Her-2 receptor on the cell.

The present invention further provides methods of inhibiting growth of a Her-2 overexpressing cell, the method comprising contacting a Her-2 overexpressing cell with a Her-2 synergistic cleavage-inhibiting amount of an MPI, wherein the MPI inhibits the activity of ADAM, and further contacting the cell with a Her-2 synergistic cleavage-inhibiting amount of a Her-2 antagonistic antibody, thereby inhibiting growth of the Her-2 overexpressing cell.

The present invention further provides methods of inducing death of a Her-2 overexpressing cell, the method comprising contacting a Her-2 overexpressing cell with a Her-2 synergistic cleavage-inhibiting amount of an MPI, wherein the MPI inhibits the activity of an ADAM, and with a Her-2 synergistic cleavage-inhibiting amount of a Her-2 antagonistic antibody, wherein the method further comprises contacting the cell with an effective amount of a cytotoxic agent, thereby inducing death of the Her-2 overexpressing cell.

The present invention further provides methods of inhibiting growth of a tumor cell overexpressing Her-2, the method comprising:

contacting the tumor cell with a Her-2 synergistic cleavage-inhibiting amount of an MPI, wherein the MPI inhibits the activity of an ADAM, and further contacting the cell with a Her-2 synergistic cleavage-inhibiting amount of a Her-2 antagonistic antibody; thereby inhibiting cleavage of the Her-2 polypeptide;

thereby inhibiting growth of the tumor cell overexpressing Her-2.

The present invention further provides methods of inhibiting a signal transduction mediated via a Her-2 receptor on a Her-2 overexpressing cell, the method comprising contacting a Her-2 overexpressing cell with a Her-2 cleavage-inhibiting amount of an ADAM inhibitor, and further contacting the cell with a Her-2 synergistic cleavage-inhibiting amount of a Her-2 antagonistic antibody, thereby inhibiting cleavage of the Her-2, thereby inhibiting the signal transduction mediated via a Her-2 receptor on the cell.

The present invention further provides methods of identifying a compound that inhibits proliferation of a Her-2 overexpressing cell by interacting with an ADAM, the method comprising contacting a Her-2 overexpressing cell with a test compound, wherein a lower level of p95 in the cell contacted with the test compound compared with the level of p95 in a second otherwise identical cell not contacted with the test compound is an indication that the test compound inhibits the Her-2 cleavage in the Her-2 over-expressing cell by binding to ADAM, thereby identifying a compound that inhibits proliferation of a Her-2 over-expressing cell by binding with the ADAM.

The present invention further provides methods of identifying a compound that inhibits cleavage of Her-2, the method comprising contacting an ADAM with a test compound in a mixture comprising an ADAM substrate, assessing cleavage of the substrate, and comparing the cleavage of the substrate by the ADAM contacted with the compound with the cleavage of the substrate by an otherwise identical ADAM not contacted with the compound, wherein a lower level of cleavage of the substrate by the ADAM contacted with the test compound compared with the level of cleavage of the substrate by the otherwise identical ADAM not contacted with the test compound is an indication that the test compound inhibits the Her-2 cleavage, thereby identifying a compound that inhibits Her-2 cleavage.

The present invention further provides methods of treating a disease mediated by overexpression of a Her-2 receptor in a human in need thereof, the method comprising administering to the human a Her-2 receptor cleavage-inhibiting amount of an ADAM inhibitor, thereby treating the disease mediated by overexpression of a Her-2 receptor in the human.

The present invention further provides compositions comprising a Her-2 cleavage-inhibiting amount of an inhibitor of ADAM and a pharmaceutically-acceptable carrier.

The present invention further provides kits for inhibiting cleavage of Her-2, the it comprising a Her-2 synergistic cleavage-inhibiting amount of an MPI, wherein the MPI inhibits the activity of an ADAM, the kit further comprising a Her-2 synergistic cleavage-inhibiting amount of a Her-2 antagonistic antibody, and an applicator and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts a summary of the 23 human ADAM family genes. Those encoding functional protein are denoted with a "+" in column 1. Human ADAM1 and ADAM3 are pseudogenes and do not encode functional proteins, this is denoted by a "−" in the table. ADAM20 lacks introns in the protein coding region ADAM20, with an analysis of the public domain genomic and cDNA sequences for ADAM20 revealing that the open reading frame extents N-terminal of the consensus start methionine and contains 50 N-terminal residues that lack a signal peptide. Based on this analysis, ADAM20 may encode a non-functional ADAM and is (denoted with "+/−"). Twelve human ADAM family members contain consensus sequences for metalloprotease active sites (HEXGHXXGXXHD (SEQ ID NO:45)) and are denoted with a "+" in column three. Of these, seven were expressed to some degree in all four shedding cell lines (denoted with a "+" in column four) while four were not expressed in at least one HER2 shedding cell line (denoted with a "−"). The final list of HER2 sheddase candidates are denoted with a "+" in column five. ADAM17 was ruled out as a candidate ("−") since prior studies suggested it was not the HER2 sheddase (Rio et al., 2002, J. Biol. Chem. 275:10379-10387). The genomic structure of ADAM20 made it a less likely candidate ("+/−").

FIG. 2 sets out the sequences of real-time PCR primers and probes used to assess expression levels of the ADAM family members in HER-2 shedding cell lines.

FIG. 3 depicts quantitative polymerase chain reaction (qPCR) analyses of expression of various ADAM proteins in Her-2 shedding cell lines BT474, SKOV3, SKBR3, MDA, and T47D. The degree of Her-2 shedding by each cell line is indicated by one or a series of plus marks "+" above the name of the cell line, with a greater number of plus marks indicating a greater degree of detectable Her-2 shedding. Her-2 shedding was assessed by detection of ectodomain (ECD) in conditioned medium using ELTSA as more fully described elsewhere. The expression of a particular ADAM mRNA detected in a cell line is indicated by a "+", while a "−" indicates a lack of expression in a cell line.

FIG. 5A is a bar graph depicting the effect of an siRNA to an ADAM on the level of Her-2 shedding as assessed by detecting shed ectodomain in conditioned BT474 cell medium using ELISA detection assay. Ectodomain shedding in conditioned medium obtained from BT474 cells in the presence of siRNA for ADAM8, ADAM9, ADAM10, ADAM15 and ADAM33 was assessed and the data demonstrate about 50-70% reduction in Her-2 shedding in cells in the presence of siRNA ADAM10 while Her-2 shedding was not detectably affected by the other siRNAs, except for ADAM15 siRNA which decreased Her-2 shedding by about 10% compared with mock control cells.

FIG. 5B is a bar graph depicting the level of Her-2 shedding (as measured by ectodomain release into conditioned medium) from SKBR3 cells in the presence of siRNA for ADAM8, ADAM9, ADAM10 and ADAM15. The data demonstrate that siRNA ADAM10 decreased the level of Her-2 shedding by about 50-70% while siRNA ADAM15 reduced shedding by about 25-30% compared with Her-2 shedding by SKBR3 cells in the absence of siRNA (i.e., "mock" cells). The data further show that siRNAs for ADAM8, ADAM9, and ADAM33 had no detectable effect on HER-2 shedding.

FIGS. 12A-1 and 12A-2 set forth the nucleic acid sequence of human ADAM10 (SEQ ID NO:5).

FIG. 12B sets forth the amino acid sequence of human ADAM10 (SEQ ID NO:6).

FIGS. 13A-1 and 13A-2 set forth the nucleic acid sequence of novel human ADAM15 variant 1 (SEQ ID NO:1). This variant is the most abundant ADAM15 variant detected in the cell lines examined as described elsewhere.

FIG. 13B sets forth the amino acid sequence of novel human ADAM15 variant 1 (SEQ ID NO:2).

FIGS. 14A-1 and 14A-2 set forth the nucleic acid sequence of novel human ADAM15 variant 2 (SEQ ID NO:3), which is the longest form.

FIG. 14B sets forth the amino acid sequence of novel human ADAM15 variant 2 (SEQ ID NO:4).

FIG. 18 is a diagram depicting that at the concentrations indicated, Her-2 sheddase-selective inhibitor Compound 5 synergistically enhances the antiproliferative activity of a suboptimal dose of Herceptin™ in Her-2 overexpressing BT474 cells (top panel) but not in MCF7 cells which do not overexpress Her-2 (bottom panel). Compound 5: Her-2 sheddase IC50 (198-250 nM), ADAM10 IC50 (98 nM), MMP12 IC50 (584 nM), MMP2 (inactive) and MMP3 (inactive).

DETAILED DESCRIPTION

Figure 4:
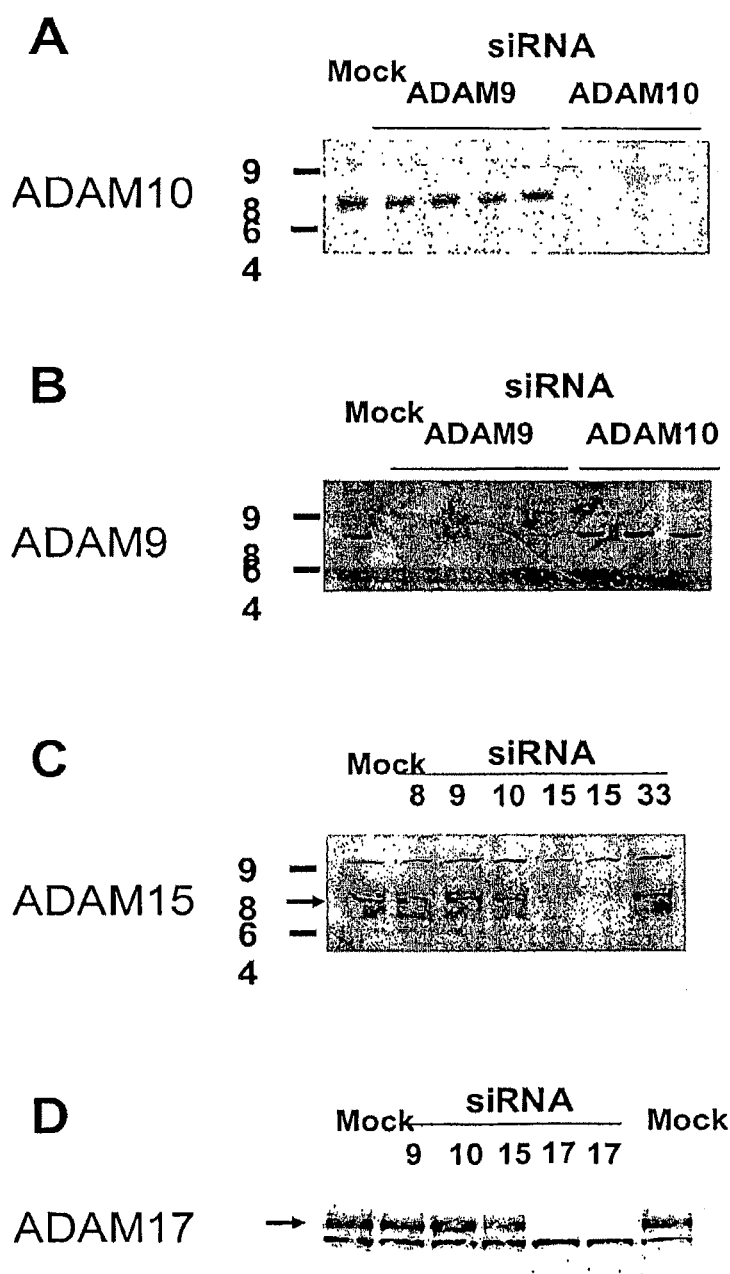
FIG. 4A is an image of a gel depicting ADAM10 protein level in a cell following knockdown using siRNA. The image depicts an image of a western blot demonstrating a reduction in ADAM10 detected in the presence of an ADAM10 siRNA compared with the level of ADAM10 in a cell in the absence of ADAM10 siRNA (indicated as "mock" on the far left of the gel). The data further demonstrates the level of ADAM9 was not detectably affected by ADAM10 siRNA demonstrating the effect was specific for the ADAM targeted by the particular siRNA. The position of a 98 kD band and 64 kD molecular weight standards are shown at left.
FIG. 4B is an image of a gel depicting a western blot analysis. The data disclosed demonstrate that the level of ADAM9 was decreased by about 75% compared with the level of ADAM9 in the absence of ADAM9 siRNA. The data further demonstrate that the effect was specific for the siRNA used in that the image depicts that ADAM10 siRNA did not detectably affect the level of ADAM9 (three lanes on the far right of the figure). The position of a 98 kD band and 64 kD molecular weight standards are shown at left.
FIG. 4C is an image of a gel depicting a western blot analysis. The arrow denotes the position of ADAM15, with the upper band on the blot representing a protein that reacts with the ADAM15 antibody non-specifically. The image depicts that the level of ADAM15 was decreased by about 75% in cells treated with ADAM15 siRNAs (lanes indicated by "15" at the top of the figure) compared with the level of ADAM15 in the absence of siRNAs (lanes indicated by "mock"). The data further demonstrate that the effect was specific for the siRNA in that the image depicts that ADAM8 siRNA (lane labeled "8"), ADAM9 siRNA (lane labeled "9"), ADAM10 siRNA (lane labeled "10"), ADAM33 siRNA (lane labeled "33") did not detectably affect the level of ADAM15. The position of a 98 kD band and 64 kD molecular weight standards are indicated along the left side of the image.
FIG. 4D is an image of a gel depicting a western blot analysis. The arrow denotes the position of ADAM17, with the lower band representing a protein that reacts with the ADAM17 antibody non-specifically. The data disclosed demonstrate that the level of ADAM17 was reduced by approximately 90% in cells treated with ADAM17 siRNAs (lanes indicated by "17" at the top of the figure) compared with the level of ADAM17 in the absence of siRNAs (lanes indicated by "mock"). The data further demonstrate that the effect was specific for the siRNA used in that administration of siRNAs against ADAMs 9, 10, and 15 (lanes indicated by "9", "10", and "15", respectively) to cells did not detectably alter the level of ADAM17 in those cells.
Figure 6:
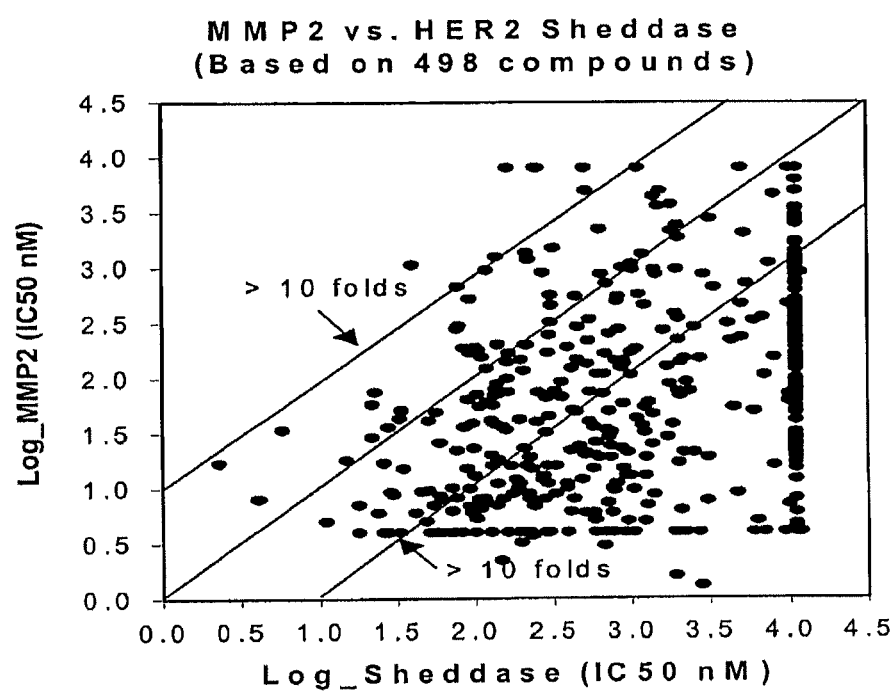
FIG. 6 is a graph depicting the lack of correlation between inhibition of sheddase and inhibition of MMP2 using 498 compounds. The figure sets forth a logarithmic plot of the IC50 values of various compounds for inhibition of MMP2 versus the IC50 values of the same compounds for inhibition of Her-2 sheddase activity. Points falling outside of the upper and lower parallel lines are greater than 10-fold divergent from the ideal correlation curve (middle line).
Figure 7:
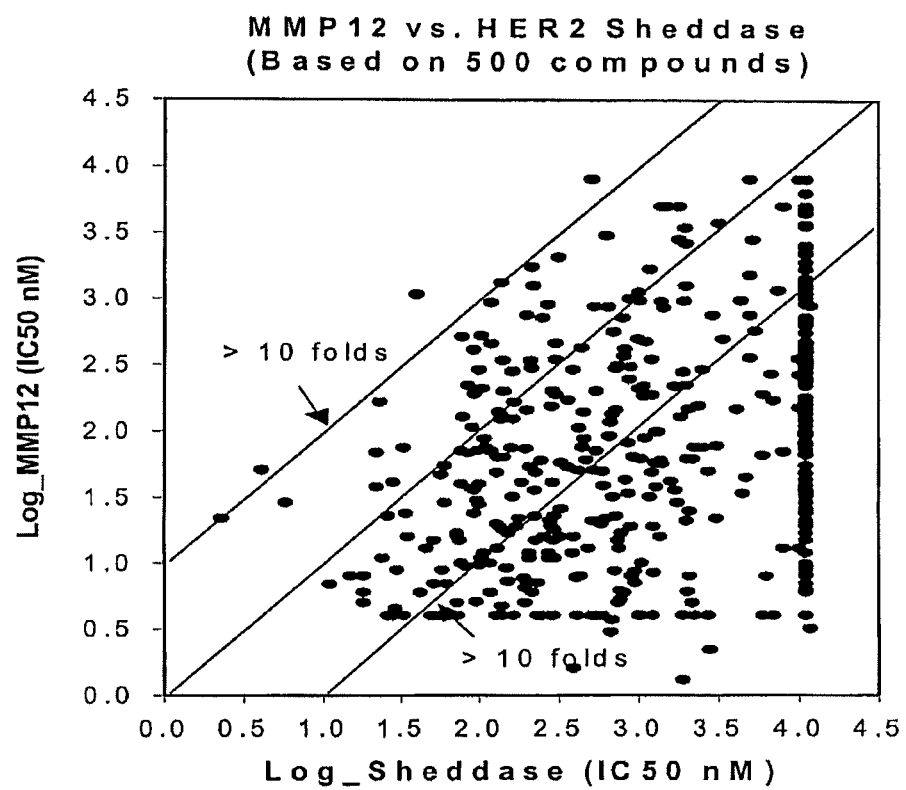
FIG. 7 is a graph depicting the lack of correlation between inhibition of sheddase and inhibition of MMP12 using over 500 compounds. The graph sets forth a logarithmic plot of the IC50 values of various compounds for inhibition of MMP12 versus the IC50 values of the same compounds for inhibition of Her-2 sheddase activity. Points falling outside of the upper and lower parallel lines are greater than 10-fold divergent from the ideal correlation curve (middle line).
Figure 8:
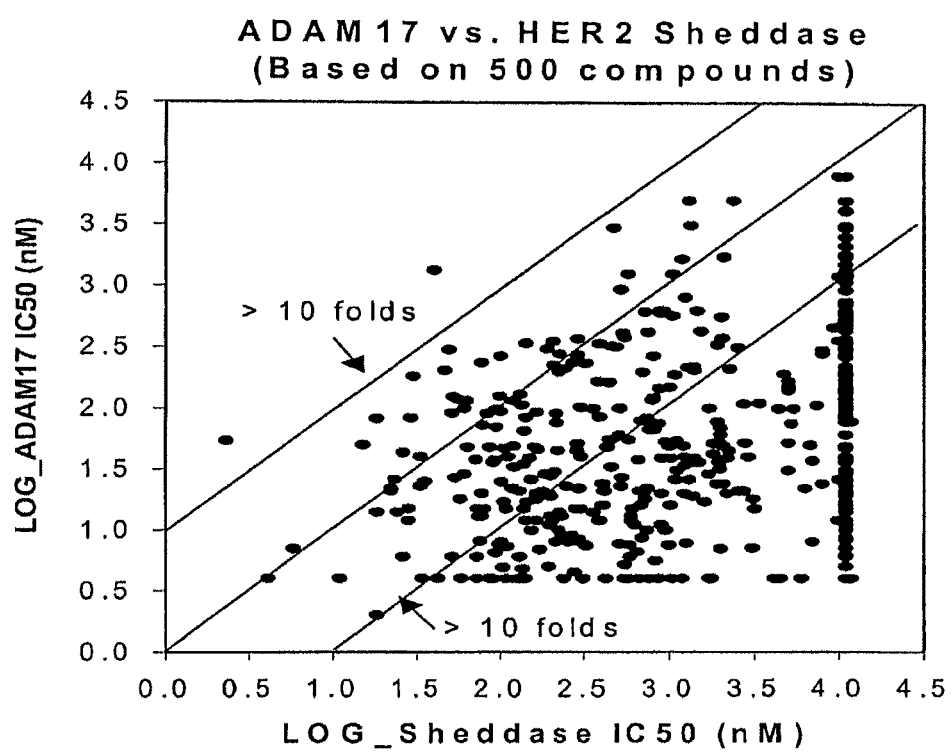
FIG. 8 is a graph depicting the lack of correlation between inhibition of sheddase and inhibition of TACE (ADAM17) using over 500 compounds. The figure sets forth a graph depicting a logarithmic plot of the IC50 values of various compounds for inhibition of TACE (ADAM17) versus the IC50 values of the same compounds for inhibition of Her-2 sheddase activity. Points falling outside of the upper and lower parallel lines are greater than 10-fold divergent from the ideal correlation curve (middle line).
Figure 9:
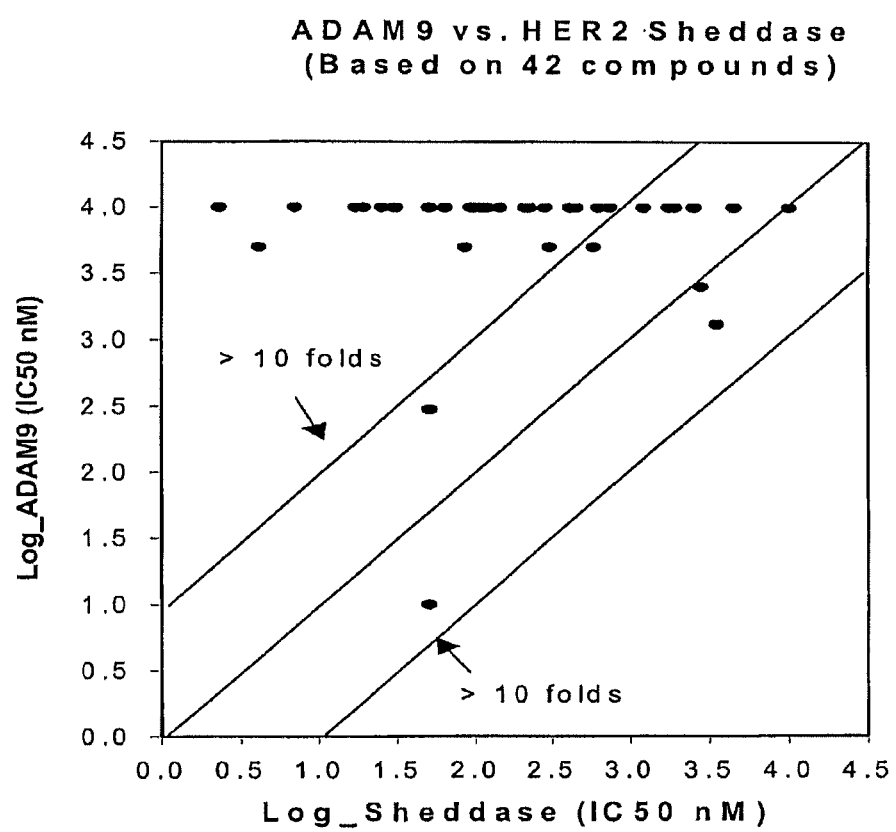
FIG. 9 is a graph depicting the lack of correlation between inhibition of sheddase and inhibition of ADAM9 using 42 compounds. The figure sets forth a graph depicting a logarithmic plot of the IC50 values of various compounds for inhibition of ADAM9 versus the IC50 values of the same compounds for inhibition of Her-2 sheddase activity. Points falling outside of the upper and lower parallel lines are greater than 10-fold divergent from the ideal correlation curve (middle line).

The present invention relates to the novel finding that ADAM polypeptides including, for example, ADAM10 and ADAM15, cleave the Her-2 receptor to produce p95, simultaneously releasing a soluble extracellular domain, ECD105 (also referred to herein as the "ectodomain"), from the Her-2 receptor. p95 is a truncated, membrane-associated receptor that, upon production, becomes constitutively active.

The present invention provides an advancement in that the data disclosed herein demonstrate that ADAM10 and ADAM15, mediate cleavage of Her-2 to produce an ECD and a p95 stub portion. Further, the present invention relates to methods for specifically inhibiting the cleavage of Her-2 using a wide plethora of cleavage inhibitors, including, but not limited to, siRNA, an antibody specific for either Her-2 or ADAM (10, 15, or both), a metalloproteinase (or metalloprotease) inhibitor (MPI) specific or selective for ADAM (e.g., ADAM10, ADAM15, or both), an antisense oligonucleotide, and the like. That is because, as would be appreciated by the skilled artisan based upon the disclosure provided herein, identification of ADAM10 and ADAM15, as enzymes involved in cleavage of Her-2 and associated production of p95, provides a plethora of approaches for the treatment of a disease, disorder or condition mediated by cleavage of Her-2 in a cell, a tissue, or a patient in need of such treatment.

Moreover, the present invention pertains to nucleic acids and proteins related to ADAM10, ADAM15, and Her-2, including DNA, RNA, vectors, host cells, peptides, and enzymes. More specifically, the present invention relates to inhibitors of Her-2 cleavage, including, but not limited to, siRNA, MPIs, and the like, since these inhibitors would be useful in inhibiting the growth, inducing the death, or both, of a Her-2 overexpressing cell where such cell was involved in, or mediated a disease, disorder or condition in a human.

The present invention further relates to the novel finding that a metalloprotease inhibitor (MPI) that inhibits cleavage of Her-2, when combined with a cytostatic agent that antagonizes Her-2 mediated cell growth, such as an antibody to Her-2, as exemplified by Herceptin™, provides a synergistic effect that inhibits the growth of a Her-2 overexpressing tumor cell. Further, when the Her-2 overexpressing tumor cell is further contacted with a cytotoxic agent, such as, but not limited to, Taxol™, and/or an inhibitor of a member of the epidermal growth factor receptor tyrosine kinase family (such as, but not limited to, Iressa™), the synergistic effect enhances the killing of the tumor cell overexpressing Her-2 or the growth inhibition of the tumor cell, respectively. Thus, the present invention provides novel synergistic methods and compositions for inhibiting the growth of and/or mediating the death of tumor cells that overexpress Her-2.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease means reducing the severity of one or more symptoms of the disease.

By the term "antagonistic antibody", as the term used herein, is meant an antibody that specifically binds with Her-2 thereby mediating detectable growth inhibition of a Her-2 overexpressing tumor cell. It would be understood that such antibody can be considered an "agonist" in certain respects in that it can, but need not, also mediate, among other things, detectable phosphorylation of the Her-2 receptor and/or affect a process associated with such phosphorylation and/or signaling via the receptor.

"ADAM inhibitor," as used herein, means any compound or substance, whether a protein, nucleic acid, small molecule, or the like, that detectably reduces cleavage of Her-2 (as assessed by detecting production of ECD, p95, or both, by a wide plethora of methods) compared with the cleavage of Her-2 in the absence of the compound. Assessment of Her-2 cleavage can be performed by any method for detecting ECD, p95, or both, as known in the art, as disclosed herein, and/or as developed in the future.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The term "apoptosis," as used herein, means an active process, involving the activation of a preexisting cellular pathway, induced by an extracellular or intracellular signal, causing the programmed death of the cell. In particular, the programmed cell death involves nuclear fragmentation, chromatin condensation, and the like, in a cell with an intact membrane.

By the term "applicator," as the term is used herein, is meant any device including, but not limited to, a hypodermic syringe, a pipette, and the like, for administering the compounds and compositions of the invention.

A "cell cycle process," as used herein, means any cellular function or process associated with the cell cycle and the various phases thereof. Thus, a cell cycle process is one associated with, or which mediates or is involved in, the cell progressing through any portion of the cell cycle.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount of a cytotoxic compound", as used herein, is meant an amount that when administered to a cell mediates a detectable level of cell death compared to the cell death detected in the absence of the compound. Cell death can be readily assessed by a plethora of art-recognized methods such as, but not limited to, performing a cell count to assess the number of viable cells before and after administration of the cytotoxic compound, assessing the level of biomolecular synthesis (e.g., protein synthesis, nucleic acid synthesis, and the like), trypan blue exclusion, MTT reduction, uptake of propidium iodide, exposure of phosphatidylserine on the cell surface, DNA fragmentation and/or ladder formation, and the like, in a cell.

The skilled artisan would understand that the amount of the compound or composition administered herein varies and can be readily determined based on a number of factors such as the disease or condition being treated, the age and health and physical condition of the mammal being treated, the severity of the disease, the particular compound being administered, and the like.

"Inducing cell death," as used herein, refers to any detectable increase in cell death in a cell contacted with a compound compared with cell death in an otherwise identical cell not contacted with the compound. Any detectable increase in the cell death in the cells contacted with the compound indicates that the compound induces cell death.

As used herein, the term "inhibiting," such as in relation to a particular biological process or activity, is meant to refer to the blocking, curbing or lessening of such process of activity. For example, inhibiting the activity of a receptor refers to decreasing, either wholly or partially, at least one measurable effect of the receptor activity. "Substantially inhibiting" refers to total blocking or significant lessening of a biological process or activity. For example, if the activity of a receptor is measurably decreased by about 75% or more of normal activity, the activity can be said to be substantially inhibited.

As used herein, the term "contacting," such as in reference to the contacting of a pharmaceutical agent (e.g., an ADAM inhibitor) with a cell or tissue, is meant to refer to the bringing together of the pharmaceutical agent and cell or tissue such that a physiological and/or chemical effect takes place as a result of the contacting agents. Contacting can take place in vitro, ex vivo or in vivo. For example, a pharmaceutical agent can be contacted with a cell culture in vitro to determine the effect of the pharmaceutical agent on the cells. In a further example, contacting of a pharmaceutical agent with a cell or tissue includes the administration of a pharmaceutical agent to a patient having the cell or tissue to be contacted. In some embodiments, when two or more pharmaceutical agents are contacted with a cell or tissue, the contacting can occur simultaneously or in succession (e.g., contacting of one pharmaceutical agent at a time, in any sequence). For example, when contacting is carried out in vivo, the two or more pharmaceutical agents can be administered to a patient at the same time (i.e., simultaneously), or in succession. In the event that the contacting of two or more agents with a cell or tissue is desired such that the physiological effects of the contacting related to each pharmaceutical agent overlap, such as when a synergistic effect is desired, then administration of the two or more pharmaceutical agents can be carried out either simultaneously or in succession within a certain time period that would allow the contacting agents to act on the cell or tissue of the patient at the same time.

By the term "inhibiting proliferation," as used herein, can be gauged by a detectable decrease in the growth of a cell, as assessed by, among other things, counting the number of cells contacted with a compound of interest and comparing the cell proliferation with otherwise identical cells not contacted which the compound. That is, the number of cells, as well as the size of the cells, can be readily assessed using any method known in the art (e.g., trypan blue exclusion and cell counting, measuring incorporation of $^3$H-thymidine into nascent DNA in a cell, and the like), or such methods as are developed in the future. The proliferation of the cells contacted with a compound is compared with the proliferation of otherwise identical cells not contacted and any detectable decrease in proliferation indicates that the compound inhibits proliferation.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue of a mammal, including affecting a cell expressing or overexpressing Her-2, as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

By "complementary to a portion or all of the nucleic acid encoding ADAM is meant a sequence of nucleic acid which does not encode an ADAM protein. Rather, the sequence which is being expressed in the cells is identical to the non-coding strand of the nucleic acid encoding ADAM protein and thus, does not encode ADAM protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein, It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, preferably, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, and most preferably, the nucleic acid fragment will be greater than about 600 nucleotides in length.

As applied to a protein, a "fragment" of an ADAM is about 20 amino acids in length. More preferably, the fragment of an ADAM is about 30 amino acids, even more preferably, at least about 40, yet more preferably, at least about 60, even more preferably, at least about 80, yet more preferably, at least about 100, even more preferably, about 100, and more preferably, at least about 150, more preferably, at least about 200, yet more preferably, at least about 250, even more preferably, at least about 300, and more preferably, at least about 320 amino acids in length amino acids in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web government site of the National Library of Medicine as part of the National Institutes of Health. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See publicly available government web site of National Center for Biotechnology Information (NCBI) of the National Library of Medicine at the National Institutes of Health.

The percent identity between two sequences can be determined using techniques similar to those described above, with or without allowing gaps. In calculating percent identity, typically exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "C" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic, acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgenic mammal" means a mammal, the germ cells of which comprise an exogenous nucleic acid.

As used herein, to "treat" means reducing the frequency with which symptoms of arterial restenosis, adventitial fibrosis, excessive or insufficient wound healing responses, scarring, keloids, bone formation, fracture healing, and the like, are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that inhibits expression of a Her-2 cleaving ADAM, to the patient, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "Her-2 synergistic amount" is an amount of a compound (e.g., a Her-2 antagonistic antibody, a Her-2 cleavage-inhibiting MPI, and the like) that when administered in concert with another such compound, reduces the level of Her-2 mediated growth in a cell (as assessed, for instance, by measuring proliferation by the cell) to a detectably greater extent than either compound administered to the cell in the absence of the other compound or to a detectably greater extent than the sum of the effect observed with either compound alone.

"Her-2 cleavage" as the term is used herein, refers to the process whereby the full-length Her-2 polypeptide (p185) is cleaved to produce a p105 ectodornain (ECD) and a p95 stub. Where the Her-2 is associated with a cell, the cleavage typically produces a p95 portion of the Her-2 polypeptide that remains associated with the cell while the ECD is released (i.e., shed) to the extracellular milieu. The enzyme that cleaves p185 to release an ECD, produce p95, or both, is referred to herein as "sheddase." Cleavage of Her-2 can be in vitro or in vivo.

By the term "Her-2 overexpressing," as the term is used herein, is meant that a cell associated with a disease, disorder or condition comprises a detectably higher level of Her-2 than an otherwise identical cell that is not associated with a disease, disorder or condition.

A "therapeutic" treatment is a treatment administered to a subject who exhibits signs of pathology for the purpose of diminishing or eliminating those signs and/or decreasing or diminishing the frequency, duration and intensity of the signs.

An "effective amount" of a compound is that amount of compound which is sufficient to provide a detectable effect to a cell to which the compound is administered when compared to an otherwise identical cell to which the compound is not administered.

By the term "an inhibitor of an epidermal growth factor receptor tyrosine kinase family member," as used herein, is meant any compound or molecule that detectably inhibits signaling via an EGFR tyrosine kinase family member. Such compounds include an antagonist, an inverse agonist, and the like, including, but not limited to, a Her-2 antagonistic antibody (e.g., Herceptin™), a small molecule inhibitor (e.g., Iressa™), a nucleic acid (e.g., antisense) that inhibits function, expression, and the like, of an EGFR tyrosine kinase family member, among other things.

An "epidermal growth factor receptor tyrosine kinase family member" means any receptor which can be classified as a member of the family based on its homology, function, and/or specificity of a ligand that binds therewith, with a known member of the EGFR family, such family member including, but not being limited to, EGFR-1 (i.e., Her-1), Her-2, Her-3, and Her-4, among others.

By the term "specifically binds," as used herein, is meant an antibody which recognizes and binds with an EGFR tyrosine kinase family protein present in a sample, but which antibody does not substantially recognize or bind other molecules in the sample.

A "suboptimal concentration" of compound is that amount of compound which is sufficient to provide a detectable effect to a cell to which the compound is administered when compared to an otherwise identical cell to which compound is not administered. This effect is less than can be maximally achieved with the same compound under identical conditions, but where the concentration of the compound administered is greater than that which mediates the detectable, but lesser, effect.

A "receptor" is a protein that specifically binds with a ligand.

To "treat" a disease as the term is used herein, means to reduce the frequency of the disease or disorder reducing the frequency with which a symptom of the one or more symptoms disease or disorder is experienced by an animal.

By the term "sheddase", as used herein, is meant a protein that specifically cleaves a Her-2 to produce an ectodomain portion that is shed from the cell and, more importantly, a p95 "stub" portion that remains associated with the cell. As demonstrated herein, ADAM10 and ADAM15, are sheddases as defined herein.

As used herein, the term "cancer," also medically termed "malignant neoplasm" is meant to refer to a disease characterized by uncontrolled cell proliferation where cancerous cells have lost their normal regulatory controls that would otherwise govern the rate of cell growth. These unregulated, dividing cells can spread throughout the body and invade normal tissues in a process referred to as "metastasis".

As used herein, the term "tumor," also medically termed "neoplasia," refers to a mass of uncontrollably dividing cells. In some embodiments, a tumor can be benign (non-invasive) or malignant (invasive). A malignant tumor is often, but not always, characteristic of cancer.

I. Isolated Nucleic Acids

The present invention includes an isolated nucleic acid encoding a mammalian ADAM15 variant, or a fragment thereof; wherein the nucleic acid encodes a variant of mammalian ADAM15, and where the nucleic acid shares at least about 90% identity with at least one nucleic acid having the sequence of SEQ ID NO:1 (human ADAM15 variant 1) and SEQ ID NO:3 (human ADAM15 variant 2). Preferably, the nucleic acid is about 95% homologous, and most preferably, about 99% homologous to at least one of SEQ ID NO:1 and SEQ ID NO:3, disclosed herein. Even more preferably, the nucleic acid is at least one of SEQ ID NO:1 and SEQ ID NO:3.

The present invention includes an isolated nucleic acid encoding mammalian ADAM15 variant, or a fragment thereof, wherein the nucleic acid shares greater than about 90% homology with SEQ ID NO:1. Preferably, the nucleic acid is about 95% homologous, and most preferably, about 99% homologous to the human ADAM15 variant 1 disclosed herein, SEQ ID NO:1. Even more preferably, the nucleic acid is SEQ ID NO:1.

The present invention includes an isolated nucleic acid encoding mammalian ADAM15 variant, or a fragment thereof, wherein the nucleic acid shares greater than about 90% homology with SEQ ID NO:3 (human ADAM15 variant 2). Preferably, the nucleic acid is about 95% homologous, and most preferably, about 99% homologous to the human ADAM15 variant 2 disclosed herein, SEQ ID NO:3. Even more preferably, the nucleic acid is SEQ ID NO:3.

In another aspect, the present invention includes an isolated nucleic acid encoding a mammalian ADAM15 variant, or a fragment thereof, wherein the protein encoded by the nucleic acid shares greater than about 90% homology with the amino acid sequence of at least one of SEQ ID NO:2 and SEQ ID NO:4. Preferably, the nucleic acid is about 95% homologous, most preferably, about 99% homologous to at least one of SEQ ID NO:2 and SEQ ID NO:4. Even more preferably, the mammalian ADAM15 variant protein encoded by the nucleic acid is at least one of SEQ ID NO:2 and SEQ ID NO:4.

In another aspect, the present invention includes an isolated nucleic acid encoding a mammalian ADAM15 variant, or a fragment thereof; wherein the protein encoded by the nucleic acid shares greater than about 90% homology with the amino acid sequence of SEQ ID NO:2 (human ADAM15 variant 1). Preferably, the protein encoded by the nucleic acid is about 95% homologous, and most preferably, about 99% homologous to the human ADAM15 variant 1 disclosed herein, SEQ ID NO:2. Even more preferably, the human ADAM15 variant 1 protein encoded by the nucleic acid is SEQ ID NO:2.

In another aspect, the present invention includes an isolated nucleic acid encoding a mammalian ADAM15 variant, or a fragment thereof, wherein the protein encoded by the nucleic acid shares greater than about 90% homology with the amino acid sequence of SEQ ID NO:4. Preferably, the protein encoded by the nucleic acid is about 95% homologous, and most preferably, about 99% homologous to the human ADAM15 variant 2 disclosed herein, SEQ ID NO:4. Even more preferably, the human ADAM15 variant 2 protein encoded by the nucleic acid is SEQ ID NO:4.

One skilled in the art would appreciate, based upon the disclosure provided herein, that other ADAM15 variant homologs likely exist in other species and can be readily identified and isolated using the methods described herein using the sequence data disclosed herein regarding the two human splice variants. Thus, the present invention encompasses additional ADAM15 variants that can be readily identified based upon the disclosure provided herein but not including any mouse variants known previously in the art.

The isolated nucleic acid of the invention should be construed to include an RNA or a DNA sequence encoding a human ADAM15 variant protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding ADAM15 variant proteins can such as those present in other species of mammals (e.g., ape, gibbon, bovine, ovine, equine, porcine, canine, feline, and the like, but not including mouse) be obtained by using the sequence information disclosed herein for human ADAM15 variant nucleic acids encoding human ADAM15 variant polypeptides as disclosed herein as would be understood by one skilled in the art. Methods for isolating a nucleic acid based on a known sequence are well-known in the art (e.g., screening of genomic or cDNA libraries), and are not described herein.

Further, any number of procedures may be used for the generation of mutant, derivative or variant forms of a human ADAM15 variant using recombinant DNA methodology well known in the art. A wide plethora of techniques is available to the skilled artisan to produce muteins of interest and to select those with desired properties.

Techniques to introduce random mutations into DNA sequences are well known in the art, and include PCR mutagenesis, saturation mutagenesis, and degenerate oligonucleotide approaches. See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

The invention includes a nucleic acid encoding a human ADAM15 variant wherein the nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one of human ADAM15 variant 1 and human ADAM15 variant 2. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize a human ADAM15 variant within a cell, a tissue, and/or a whole organism (e.g., a mammalian embryo), and to study the role(s) of a human ADAM15 variant in a cell or animal. Further, addition of a tag polypeptide facilitates isolation and purification of the "tagged" protein such that the proteins of the invention can be produced and purified readily.

II. Isolated Polypeptides

The invention also includes an isolated polypeptide comprising a human ADAM15 variant molecule. Preferably, the isolated polypeptide comprising a human ADAM15 variant molecule is greater than about 90% homologous to a polypeptide having the amino acid sequence of at least one of SEQ ID NO:2 and SEQ ID NO:4. The skilled artisan would understand, based upon the disclosure provided herein, that the polypeptide of the invention does not include any mouse ADAM15 variant described previously. Preferably, the isolated polypeptide is about 90% homologous, more preferably, about 95% homologous, and most preferably, about 99% homologous to at least one of SEQ ID NO:2 and SEQ ID NO:4. More preferably, the isolated polypeptide comprising a human ADAM15 variant is at least one of human ADAM15 variant 1 and human ADAM15 variant 2. Most preferably, the isolated polypeptide comprising a mammalian ADAM15 variant is at least one of SEQ ID NO:2 and SEQ ID NO:4.

The invention also includes an isolated polypeptide comprising a human ADAM15 variant molecule. Preferably, the isolated polypeptide comprising a human ADAM15 variant is greater than about 90% homologous to a polypeptide having the amino acid sequence of SEQ ID NO:2. More preferably, the isolated polypeptide comprising a human ADAM15 variant is at least about 95% homologous, and more preferably, at least about 99% homologous to human ADAM15 variant 1. More preferably, the isolated polypeptide comprising a human ADAM15 variant molecule is human ADAM15 variant 1. Most preferably, the isolated polypeptide comprising a human ADAM15 variant molecule is SEQ ID NO:2.

The invention also includes an isolated polypeptide comprising a human ADAM15 variant wherein, preferably, the isolated polypeptide comprising a human ADAM15 variant is greater than about 90% homologous to a polypeptide having the amino acid sequence of SEQ ID NO:4. More preferably, the isolated polypeptide comprising a human ADAM15 variant is at least about 95% homologous, and more preferably, at least about 99% homologous to human ADAM15 variant 2. More preferably, the isolated polypeptide comprising a human ADAM15 variant is human ADAM15 variant 2. Most preferably, the isolated polypeptide comprising a human ADAM14 variant molecule is SEQ ID NO:4.

The present invention also provides for analogs of proteins or peptides which comprise a mammalian ADAM15 variant molecule as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are ADAM15 peptides which are altered in one or more amino acids (or, when referring to the nucleotide sequence encoding the same, are altered in one or more base pairs) such that the resulting peptide (or DNA) is not identical to the sequences recited herein, but has the same biological property as the ADAM15 variant peptides disclosed herein, in that the peptide has biological/biochemical properties of the ADAM15 variant peptide of the present invention (e.g., it can specifically cleave Her-2 to produce, inter alia, a p95 Her-2 portion).

The skilled artisan would understand, based upon the disclosure provided herein, that ADAM15 biological activity encompasses, but is not limited to, the ability of a molecule to specifically cleave Her-2 to produce an ectodomain portion (p105) and a p95 stub portion, and the like.

Further, the invention should be construed to include naturally occurring variants or recombinantly derived mutants of ADAM15 variant sequences, which variants or mutants render the protein encoded thereby either more, less, or just as biologically active as the full-length clones of the invention.

The nucleic acids, and peptides encoded thereby, are useful tools for elucidating the function(s) of ADAM15 molecule in a cell. Further, nucleic and amino acids comprising a mammalian ADAM15 variant molecule are useful diagnostics which can be used, for example, to identify a compound that affects ADAM15 variant function or expression, which compound is a potential drug candidate for a disease, disorder or condition associated with, or mediated by, cleavage of Her-2 to produce a p95 portion of Her-2. The nucleic acids, the proteins encoded thereby, or both, can be administered to a cell, tissue, or mammal to increase or decrease expression or function of ADAM15, or a variant thereof, including, but not limited to, variant 1 and 2 as disclosed herein, in the cell, tissue or mammal to which it is administered. This can be beneficial for the cell, tissue, and/or mammal in situations where under or over-expression of ADAM15, or variant thereof, in the cell, tissue or mammal mediates a disease or condition associated with cleavage of Her-2 to produce p95.

That is, the data disclosed herein demonstrate that cleavage of Her-2 by p95 is associated with certain diseases, disorders or conditions. Even more importantly, the data disclosed herein demonstrate that inhibition of such cleavage can provide a therapeutic benefit. Also, the data disclosed herein demonstrate for the first time that ADAM10, and ADAM15 are responsible, at least in part, for the cleavage of Her-2 to release p105 ectodomain and to produce cell-associated p95. Thus, these ADAM molecules are important targets for the production of potential therapeutics. Further, the data suggest that a variant of ADAM15, variant 1, is preferentially associated with Her-2 cleavage in cells that shed p105 and produce p95. Thus, ADAM15, and variants thereof, even more preferably, variants 1 and 2 disclosed herein, are important potential therapeutic targets.

Additionally, the nucleic and amino acids of the invention can be used to produce recombinant cells and transgenic non-human mammals which are useful tools for the study of ADAM15 action, and the study of the action of the various variants thereof (e.g., variant 1 and variant 2, and the like), the identification of novel diagnostics and therapeutics for treatment of diseases, disorders or conditions associated with, or mediated by, cleavage of Her-2, including, but not limited to, certain cancers, among other things. Further, the nucleic and amino acids of the invention can be used diagnostically, either by assessing the level of gene expression or protein expression, to assess severity, metastasis, and prognosis of certain cancers. The nucleic acids and proteins of the invention are also useful in the development of assays to assess the efficacy of a treatment for diseases or disorders associated with, or characterized by, cleavage of Her-2. That is, the nucleic acids and polypeptides of the invention can be used to detect the effect of various therapies on ADAM15 molecule, or variant thereof, expression, thereby ascertaining the effectiveness of the therapies. Thereby, the nucleic acids and proteins of the present invention can provide useful diagnostic tools for, among other things, cancer.

III. Vectors

In other related aspects, the invention includes an isolated nucleic acid encoding a mammalian ADAM15 variant operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Expression of an ADAM15 variant, either alone or fused to a detectable tag polypeptide, in cells which either do not normally express the ADAM15 variant, or which do not express ADAM15 variant fused with a tag polypeptide, can be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter, and the like.

Moreover, inducible and tissue specific expression of the nucleic acid encoding WNK may be accomplished by placing the nucleic acid encoding WNK, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing ADAM15 variant using a vector allows the isolation of large amounts of recombinantly produced protein. Further, where a decreased level of ADAM15 variant expression or function results in a disease, disorder, or condition associated with such expression, the expression of ADAM15 variant driven by a promoter/regulatory sequence can provide useful therapeutics including, but not limited to, gene therapy whereby ADAM15 variant is provided. That is, based upon the disclosure provided herein, the skilled artisan would appreciate that there are situations and/or conditions where it is desirable to increase ADAM15 expression and/or function, and the nucleic acid vectors of the present invention provide a method for thus providing ADAM15 variant expression and/or function to a cell, tissue or mammal in need thereof where it would provide a therapeutic benefic understood by one skilled in the art based upon the teaching provided herein.

Therefore, the invention includes not only methods of inhibiting ADAM15 variant expression, translation, and/or activity, but it also includes methods relating to increasing ADAM15 variant expression, protein level, and/or activity since both decreasing and increasing ADAM15 variant expression and/or activity can be useful in providing effective therapeutics.

Selection of any particular plasmid vector or other DNA vector is not a limiting factor in this invention and a wide variety of vectors is well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a mammalian ADAM15 variant. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art, and is detailed in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding ADAM15 variant may be cloned into various plasmid vectors. However, the present invention should not be construed to be limited to plasmids or to any particular vector. Instead, the present invention should be construed to encompass a wide plethora of vectors which are readily available and/or well-known in the art.

IV. Recombinant Cell

The invention includes a recombinant cell comprising, inter alia, an isolated nucleic acid encoding ADAM15 variant, an antisense nucleic acid complementary thereto, a nucleic acid encoding an antibody that specifically binds ADAM15 variant, and the like. In one aspect, the recombinant cell can be transiently transfected with a plasmid encoding a portion of the nucleic acid encoding ADAM15 variant. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, kidney cells, and the like.

The invention should be construed to include any cell type into which a nucleic acid encoding a mammalian ADAM15 variant (a transgene) is introduced, including, without limitation, a prokaryotic cell and a eukaryotic cell comprising an isolated nucleic acid encoding mammalian ADAM15 variant.

The invention also encompasses a recombinant cell where an endogenous target nucleic acid ADAM15 variant is activated by introduction of an exogenous activating nucleic acid into the cell such that the endogenous target nucleic acid is expressed and/or the ADAM15 variant protein is produced. Such techniques of gene activation are well-known in the art and are described, for example, in U.S. Pat. No. 6,270,989, among many others.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, cancer, or any other disease, disorder or condition mediated by ADAM15 cleavage of Her-2, and the like.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding ADAM15 variant can be used to provide ADAM15 variant, to a cell, tissue, or whole animal where a higher level of ADAM15 variant can be useful to treat or alleviate a disease, disorder or condition associated with low level of ADAM15 variant expression and/or activity. Therefore, the invention includes a cell expressing ADAM15 variant (variant 1, variant 2, or both) to increase or induce ADAM15 variant expression, translation, and/or activity, where increasing ADAM15 variant expression, protein level, and/or activity can be useful to treat or alleviate a disease, disorder or condition, since increasing ADAM15 variant also increases cleavage of Her-2 to produce p95.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding WNK and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (i.e., a "knock-out" vector) or which insert (i.e., a "knock-in" vector) a nucleic acid encoding ADAM15 variant, or a fragment thereof, from or into a mammalian genome, respectively. The crucial feature of the targeting vector is that it comprise sufficient portions of two sequences located towards opposite, i.e., 5' and 3', ends of the ADAM15 variant open reading frames (ORF) in the case of a "knock-out" vector, to allow deletion/insertion by homologous recombination to occur such that all or a portion of the nucleic acid encoding ADAM15 variant is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the ADAM15 variant coding region to be used in the targeting vector may be easily selected based upon known methods and following the teachings disclosed herein based on the disclosure provided herein including the nucleic and amino acid sequences of both variants of human ADAM15 variant 1 and variant 2. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of transgenic a cell where the nucleic acid encoding ADAM15 variant, or a portion thereof, has been deleted and replaced with the neomycin resistance gene by the cell's ability to grow in the presence of G418.

However, the present invention should not be construed to be limited to neomycin resistance as a selectable marker. Rather, other selectable markers well-known in the art may be used in the knock-out targeting vector to allow selection of recombinant cells where the ADAM15 variant gene has been deleted and/or inactivated and replaced by the nucleic acid encoding the selectable marker of choice. Methods of selecting and incorporating a selectable marker into a vector are well-known in the art and are described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

One skilled in the art would appreciate, based upon this disclosure, that cells comprising decreased levels of ADAM15 variant protein, decreased level of ADAM15 variant activity, or both, include, but are not limited to, cells expressing inhibitors of ADAM15 variant expression (e.g., antisense or ribozyme molecules).

Methods and compositions useful for maintaining mammalian cells in culture are well known in the art, wherein the mammalian cells are obtained from a mammal including, but not limited to, a rat and a human.

The recombinant cell of the invention can be used to study the effect of qualitative and quantitative alterations in ADAM15 variant levels on a cell, including the effect of decreased cleavage of Her-2 in a cell expressing Her-2. This is because the fact that ADAM15, and variants thereof, have now been demonstrate to mediate cleavage of Her-2 to produce p95, wherein p95 is associated with, or mediates, altered cell growth and/or proliferation and is correlated with, among other things, metastasis of certain cancers. Further, the recombinant cell can be used to produce ADAM15 variant for use for therapeutic and/or diagnostic purposes. That is, a recombinant cell expressing ADAM15 variant can be used to produce large amounts of purified and isolated ADAM15 variant that can be administered to treat or alleviate a disease, disorder or condition associated with or caused by an increased or inappropriate level of ADAM15 variant.

Alternatively, recombinant cells expressing ADAM15 variant can be administered in ex vivo and in vivo therapies where administering the recombinant cells thereby administers the protein to a cell, a tissue, and/or an animal. Additionally, the recombinant cells are useful for the discovery of processes affected and/or mediated by ADAM15 variants. Thus, the recombinant cell of the invention may be used to study the effects of elevated or decreased ADAM15 variant levels on a cell, and the like.

The recombinant cell of the invention, wherein the cell has been engineered such that it does not express ADAM15 variant, or expresses reduced or altered ADAM15 variant lacking biological activity, can also be used in ex vivo and in vivo cell therapies where either an animal's own cells (e.g., kidney cells, and the like) or those of a syngeneic matched donor, are recombinantly engineered as described elsewhere herein (e.g., by insertion of an antisense nucleic acid, an siRNA, or a knock-out vector such that ADAM15 variant expression and/or protein levels are thereby reduced in the recombinant cell), and the recombinant cell is administered to the recipient animal. In this way, recombinant cells that express ADAM15 variant at a reduced level can be administered to an animal whose own cells express increased levels of ADAM15 variant thereby treating or alleviating a disease, disorder or condition associated with or mediated by increased ADAM15 variant expression as disclosed elsewhere herein, including, but not limited to, a disease, disorder or condition associated with, or mediated by, cleavage of Her-2 to produce p95 by ADAM15, or a variant thereof (e.g., ADAM15 variant 1 and variant 2, among others).

V. Antibodies

The invention also includes an antibody that specifically binds ADAM15 variant, or a fragment thereof.

One skilled in the art would understand, based upon the disclosure provided herein, that an antibody that specifically binds ADAM15 variant, binds with a protein of the invention, such as, but not limited to human ADAM15 variant 1, variant 2, or an immunogenic portion thereof. In one embodiment, the antibody is directed to: human ADAM15 variant 1, comprising the amino acid sequence of SEQ ID NO:2, and human ADAM15 variant 2, comprising the amino acid sequence SEQ ID NO:4.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.; and Wilson et al., 2001, Science 293: 1107-1112). Such techniques include immunizing an animal with a chimeric protein comprising a portion of another protein such as a maltose binding protein or glutathione (GSH) tag polypeptide portion, and/or a moiety such that the ADAM15 variant portion is rendered immunogenic (e.g., ADAM15 variant conjugated with keyhole limpet hemocyanin, KLH) and a portion comprising the respective ADAM15 variant amino acid residues. The chimeric proteins are produced by cloning the appropriate nucleic acids encoding ADAM15 variant (e.g., SEQ ID NO:1 and SEQ ID NO:2) into a plasmid vector suitable for this purpose, such as but not limited to, pMAL-2 or pCMX.

However, the invention should not be construed as being limited solely to these antibodies or to these portions of the protein antigens. Rather, the invention should be construed to include other antibodies, as that term is defined elsewhere herein, to human ADAM15 variant, or portions thereof. Further, the present invention should be construed to encompass antibodies, inter alia, that bind to ADAM15 variant and they are able to bind ADAM15 variant present on Western blots, in immunohistochemical staining of tissues thereby localizing ADAM15 variant in the tissues, and in immunofluorescence microscopy of a cell transiently transfected with a nucleic acid encoding at least a portion of ADAM15 variant.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with mammalian ADAM15 variant. That is, the invention includes immunizing an animal using an immunogenic portion, or antigenic determinant, of the ADAM15 variant protein.

The antibodies can be produced by immunizing an animal such as, but not limited to, a rabbit or a mouse, with a protein of the invention, or a portion thereof, or by immunizing an animal using a protein comprising at least a portion of ADAM15 variant protein, or a fusion protein including a tag polypeptide portion comprising, for example, a maltose binding protein tag polypeptide portion, covalently linked with a portion comprising the appropriate ADAM15 variant amino acid residues. One skilled in the art would appreciate, based upon the disclosure provided herein, that smaller fragments of these proteins can also be used to produce antibodies that specifically bind an ADAM15 variant.

One skilled in the art would appreciate, based upon the disclosure provided herein, that various portions of an isolated ADAM15 variant polypeptide can be used to generate antibodies to either conserved regions of ADAM15 variant or to non-conserved regions of the polypeptide. As disclosed elsewhere herein, ADAM15 comprises various conserved domains.

Once armed with the sequence of WNK and the detailed analysis localizing the various conserved and non-conserved domains of the protein, the skilled artisan would understand, based upon the disclosure provided herein, how to obtain antibodies specific for the various portions of a mammalian ADAM15 polypeptide using methods well-known in the art or to be developed.

Further, the skilled artisan, based upon the disclosure provided herein, would appreciate that the non-conserved regions of a protein of interest can be more immunogenic than the highly conserved regions which are conserved among various organisms. Further, immunization using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of each ADAM15 molecule can be used to produce antibodies that are specific only for that ADAM15 and do not cross-react non-specifically with other ADAM15s or with other proteins. More specifically, the skilled artisan, once armed with the teachings provided herein, would readily appreciate that antibodies can be produced that react with ADAM15 variant 1, but not with variant 2, and vice-a-versa.

Alternatively, the skilled artisan would also understand, based upon the disclosure provided herein, that antibodies developed using a region that is conserved among one or more ADAM15 molecules can be used to produce antibodies that react specifically with one or more ADAM15 molecule(s). That is, once armed with the sequences disclosed herein, one skilled in the art could readily prepare, using methods well-known in the art, antibodies that specifically bind with ADAM15 variant 1 and with ADAM15 variant 2. Methods for producing antibodies that specifically bind with a conserved protein domain which may otherwise be less immunogenic than other portions of the protein are well-known in the art and have been discussed previously, and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one ADAM15 variant and antibodies that specifically bind with more than one ADAM15 variant, including antibodies that specifically bind with all ADAM15 variants of the invention.

One skilled in the art would appreciate, based upon the disclosure provided herein, which portions of ADAM15 variant are less homologous with other proteins sharing conserved domains. However, the present invention is not limited to any particular domain; instead, the skilled artisan would understand that other non-conserved regions of the ADAM15 variant proteins of the invention can be used to produce the antibodies of the invention as disclosed herein.

Therefore, the skilled artisan would appreciate, based upon the disclosure provided herein, that the present invention encompasses antibodies that neutralize and/or inhibit ADAM15 variant activity (e.g., by inhibiting necessary ADAM15 variant/Her-2 protein/protein interactions) which antibodies can recognize one or more ADAM15 variants, including, but not limited to, human ADAM15 variant 1, ADAM15 variant 2, as well as ADAM15s from various species (e.g., mouse, non-human primates).

One skilled in the art would also understand, based upon the disclosure provided herein, that it may be advantageous to inhibit the activity and/or expression of one type of ADAM15 variant molecule without affecting the activity and/or expression of other ADAM15 variants or other ADAM15 molecules. For example, it may be beneficial to inhibit ADAM15 variant 1 expression, while not inhibiting the expression and/or activity of ADAM15 variant 2, or another ADAM15, in other tissues where the existing level of ADAM15 variant 2, or other ADAM15, in the these other tissues is necessary for continued proper functioning of cellular processes in that tissue. Thus, whether inhibition of ADAM15 expression and/or activity is achieved using antibodies, antisense nucleic acids, and the like, one skilled in the art would appreciate, based upon the disclosure provided herein, that the present invention encompasses selectively affecting one or more ADAM15 molecules and, in certain cases, the invention encompasses inhibiting the expression or activity of all ADAM15 molecules. Whether one or more ADAM15 molecule should be affected can be readily determined by the skilled artisan based on which disease, disorder or condition is being treated, and the specific cell and/or tissue being targeted.

The invention should not be construed as being limited solely to the antibodies disclosed herein or to any particular immunogenic portion of the proteins of the invention. Rather, the invention should be construed to include other antibodies, as that term is defined elsewhere herein, to ADAM15 variant, or portions thereof, or to proteins sharing greater than 70% homology with a polypeptide having the amino acid sequence of at least one of SEQ ID NO:2 and SEQ TD NO:4. Preferably, the polypeptide is about 80% homologous, more preferably, about 90% homologous, even more preferably, about 95% homologous, and most preferably, about 99% homologous to at least one of human ADAM15 variant 1 (SEQ ID NO:2) and human ADAM15 variant 2 (SEQ ID NO:4). More preferably, the polypeptide that specifically binds with an antibody specific for mammalian ADAM15 variant is at least one of human ADAM15 variant 1 and human ADAM15 variant 2. Most preferably, the polypeptide that specifically binds with an antibody that specifically binds with a mammalian ADAM15 variant is at least one of SEQ ID NO: 2 and SEQ ID NO:4.

The invention encompasses polyclonal, monoclonal, synthetic antibodies, and the like. One skilled in the art would understand, based upon the disclosure provided herein, that the crucial feature of the antibody of the invention is that the antibody bind specifically with ADAM15 variant. That is, the antibody of the invention recognizes ADAM15 variant, or a fragment thereof (e.g., an immunogenic portion or antigenic determinant thereof), on Western blots, in immunostaining of cells, and immunoprecipitates ADAM15 variant using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be used to decrease the level of ADAM15 variant in a cell thereby inhibiting the effect(s) of ADAM15 variant in a cell. Thus, by administering the antibody to a cell or to the tissues of an animal or to the animal itself, the required ADAM15 variant/Her-2 protein/protein interactions are therefore inhibited such that the effect of ADAM15 variant-mediated activity are also inhibited. One skilled in the art would understand, based upon the disclosure provided herein, that detectable effects upon inhibiting ADAM15 variant/Her-2 protein/protein interaction and/or activity using an anti-ADAM15 variant antibody can include, but are not limited to, decreased cleavage of Her-2, decreased shedding of the Her-2 ectodomain, decreased level of p95, decreased level of p95-mediated processes, and the like.

One skilled in the art would appreciate, based upon the disclosure provided herein, that the invention encompasses administering an antibody that specifically binds with ADAM15 variant orally, parenterally, or both, to inhibit ADAM15 variant function in cleaving Her-2.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be "humanized" using the technology described in, for example, Wright et al. (1992, Critical Rev. Immunol. 12:125-168), and in the references cited therein, and in Gu et al. (1997, Thrombosis and Hematocyst 77:755-759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., (1989, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (1992, Critical Rev. Immunol. 12:125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In addition to administering an antibody to a cell to inhibit the activity and/or expression of mammalian ADAM15 variant, the invention encompasses administering an antibody that specifically binds with a mammalian ADAM15 variant, or a nucleic acid encoding the antibody, wherein the molecule further comprises an intracellular retention sequence such that antibody binds with the ADAM15 variant and prevents its expression at the cell surface, or at other locations throughout the subcellular milieu. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11-17). Thus, the invention encompasses methods comprising inhibiting binding of ADAM15 variant with a Her-2 molecule, thereby preventing cleavage of Her-2 by the ADAM15 variant using methods comprising, among other things, antibodies, chemical compounds, small molecules, peptidomimetics, drugs, and the like, as well as methods of inhibiting the cleavage by inhibiting the expression or intracellular trafficking of the ADAM15 variant using, inter alia, inhibiting the ADAM15 variant being present on the cell surface (e.g., methods comprising ribozymes, antisense molecules, intrabodies, and the like), and such methods as become known in the future for inhibiting protein/protein interaction on the cell surface between ADAM15 variant and Her-2.

VI. Methods and Compositions Relating to Identification of Role of ADAM in Cleavage of Her-2

The importance of Applicants' discovery of cleavage of Her-2 by ADAM, such as ADAM10 or ADAM15, is now discussed and methods, compositions and kits relating to this crucial breakthrough are now described as follows.

Methods Relating to Inhibition of ADAM10/15 Cleavage of Her-2

As discussed in detail elsewhere herein, Her-2 has been found to play a role in a number of human carcinomas. Without wishing to be bound by any particular theory, a mechanism proposed by which Her-2 may play a role in cancer may be by cleavage of Her-2 receptor to form the membrane-associated constitutively-active receptor p95. The presence of p95 has been correlated to aggressive forms of breast cancer, as well as forms of breast cancer that are more likely to recur. Therefore, methods and compositions that can inhibit the production of p95 in vivo may be useful in treating and/or preventing certain types of cancer. It had been suggested that cleavage of Her-2 produces a constitutively active p95 stub from Her-2 and that the increased signaling associated or mediated by the stub plays a role in tumor cell metastasis and is associated with poor clinical outcome in cancers relating to Her-2 overexpressing tumors. However, it was not known, until the present invention, which protein, or proteins, mediated cleavage of Her-2 to produce an ECD, and, more importantly, to produce the cell-associated p95 stub. This was an obstacle to development of potential treatments and therapeutic modalities since the "target" for the therapy had not been identified and the therapy, therefore, could not be limited to any particular target so as to limit any unwanted effects) on unrelated processes.

The present invention provides, for the first time, the identification of a protein that mediates the cleavage of Her-2 to produce p95 (as well as ECD), referred to herein as "sheddase." The identified proteins belong to the ADAM family. Members of the ADAM family of proteins are known to play various roles in a cell. Further, a number of known ADAMs have been shown to have metalloprotease activity and to have consensus sequences for active metalloprotease domains, Nonetheless, until the present invention, it had not been demonstrated that an ADAM, more specifically, ADAM10 and ADAM15, mediated Her-2 shedding associated with, among other things, cancer.

The invention provides a method for preventing cleavage of Her-2 where the Her-2 is associated with a cell. This is because the data disclosed herein demonstrate that a number of ADAM proteins are expressed in various Her-2-containing cell lines. Such cell lines include, but are not limited to, Her-2 shedding cell lines BT474, SKOV3, SKBR3, MDA, MCF7, and T47D. Advantageously, the present invention provides methods for the inhibition of ADAM-mediated Her-2 cleavage in Her-2-containing cell lines. The data disclosed herein demonstrate, for the first time, that inhibition or abrogation of ADAM10 and/or ADAM15, unexpectedly reduces Her-2 shedding in cells. That is, it has been found that contacting a Her-2 overexpressing cell which contains ADAM10, ADAM15, or both, with an inhibitor of such ADAM, detectably reduces shedding of the Her-2 ectodomain ECD-105, and therefore, production of p95 Her-2, is detectably inhibited.

The invention further provides a method for preventing cleavage of Her-2 in vivo. The data provided herein shows that inhibition of Her-2 cleavage in vivo is associated with inhibition of tumor growth. The data further provide that ADAM inhibitors alone mediate inhibition of in vivo Her-2 cleavage, inhibition of tumor growth, and in vivo inhibition of kinase signaling pathways. Accordingly, inhibition of Her-2 cleavage in vivo can be useful in the treatment of cancer.

Therefore, it is a feature of the present invention to provide a method for preventing cleavage of Her-2 to form p95 in a cell, in vitro or in vivo. As discussed elsewhere herein, prevention of p95 formation may be useful in control of cell growth and in treatment of cancer. The data disclosed herein demonstrate, among other things, that Her-2 shedding, cell proliferation, and tumor growth is inhibited where a cell is contacted with a Her-2 cleavage-inhibiting amount of an ADAM10, ADAM15, or both, inhibitor. As will be understood by one of skill in the art, a "Her-2 cleavage-inhibiting amount" of an ADAM inhibitor is an amount of such an inhibitor that detectably reduces the cleavage of Her-2 as demonstrated by detectably decreasing the level of p95, p105 ECD, or both. As described in greater detail elsewhere herein, preventing cleavage of Her-2 to form p95 is useful when the effects of the constitutively-active p95 "stub" are not desired, or are sought to be eliminated.

One skilled in the art would appreciate, based upon the disclosure provided herein, that where a cell or tissue produces both ADAM10 and ADAM15, and/or where p95 production is mediated by both ADAMs, that an inhibitor of each can be administered, either simultaneously or separately, to the cell or tissue. Alternatively, the skilled artisan would understand that where an inhibitor inhibits both ADAM10 and ADAM15, such an inhibitor can be used to inhibit the cleavage of Her-2 to produce p95. Further, the artisan would appreciate, based upon the teachings provided herein, that various combinations of inhibitors can be administered to inhibit sheddase activity, and the present invention is not limited in any way with regard to the administration of one or any number and combination of ADAM inhibitor(s).

An inhibitor of the cleavage of Her-2 by ADAM is an ADAM polypeptide inhibitor. An inhibitor of an ADAM10 or ADAM15, or both, polypeptide can be a nucleic acid, a polypeptide, or any other molecule or compound known by one skilled in the relevant art to be useful for inhibition of protein-mediated activity. Further, an ADAM inhibitor can be an antisense nucleic acid, a ribozyme, an antibody, or a small molecule inhibitor. While the present invention is exemplified by inhibition of ADAM activity using a siRNA molecule, the invention is not limited to this, or any other inhibitor of Her-2 cleavage. Indeed, novel MPIs, have also been disclosed elsewhere herein, that can be used to inhibit sheddase cleavage of Her-2. Thus, one skilled in the art would appreciate, based upon the disclosure provided herein, that the invention is in no way limited to these, or any other, sheddase inhibitors. Rather, the invention includes any ADAM inhibitor that detectably decreases cleavage of Her-2 to produce p95, including any to be developed in the future as would be understood based upon the teachings provided herein. More specifically, the invention includes any inhibitor of ADAM10, ADAM15, or an inhibitor that inhibits both.

As described elsewhere herein, ADAM comprises a metalloprotease domain, and has been demonstrated herein to have metalloprotease activity. ADAM family members are zinc proteases that are comprised of $NH_2$-signal peptide, pro domain, catalytic domain, disintegrin domain, cysteine rich region, EGF repeat, transmembrane region, cytoplasmic tail. ADAM10 and ADAM15 are both type I membrane proteins and their catalytically active protease domain is located extracellularly. These extracellular catalytic domain places the protease activity in juxtaposition with the region of Her-2 cleaved during ecto domain shedding. Therefore, an ADAM inhibitor useful in the present invention is an inhibitor of ADAM (e.g., ADAM10 and ADAM15) biological activity wherein such "biological activity" includes, but is not limited to, cleavage of Her-2, and more particularly, the cleavage of Her-2 to form p95, ECD, or both. Because the cleavage of Her-2 to form p95 has been implicated herein to play a role in the progression of cancer in Her-2 overexpressing cells, the biological activity of ADAM10 or ADAM15 as used herein also encompasses a the potential to inhibit cell growth, induce cell death, and other anticarcinogenic effect.

The present invention features methods of inhibiting cleavage of Her-2 in a cell comprising Her-2, in vitro or in vivo. As set forth in detail elsewhere herein, the cleavage of Her-2 produces p95 and ECD105, and based on the data disclosed for the first time herein, p95 is implicated in subsequently playing a role in the development and progression of cancer. Therefore, one of skill in the art would understand, based on the disclosure herein, that inhibition of the cleavage of Her-2 will repress the production of p95 and attendant carcinogenic processes. The reduction of p95 production is useful for the prevention of any conditions or disorders associated with increased Her-2/p95 signaling. For example, as disclosed in detail elsewhere herein, overexpression of Her-2 occurs in 25-30% of breast cancers. Patients with Her-2 overexpressing tumors have a distinctly unfavorable clinical course, characterized by shortened time to disease recurrence and reduced survival. Therefore, the repression of p95 production can inhibit and/or decrease Her-2/p95-based signaling, subsequently minimizing the unfavorable clinical course of Her-2/p95-mediated disease.

In an embodiment of the present invention, a cell containing Her-2 is contacted with an ADAM (e.g., ADAM10, ADAM15, or both) inhibitor capable of inhibiting the cleavage of Her-2. As will be understood by one of skill in the art, an ADAM inhibitor exhibiting the ability of inhibiting cleavage of Her-2, i.e., an inhibitor of p95 production, can be identified using methods well known in the art, including those described elsewhere herein. By way of a non-limiting example, an inhibitor of Her-2 cleavage can be identified by monitoring the cleavage of Her-2 in a first system in which ADAM10, or ADAM15, or both, is provided in the presence of a putative Her-2 cleavage-inhibiting ADAM inhibitor, and comparing the results obtained in the first system with the results obtained from a second system in which the same ADAM is provided in the absence any Her-2 cleavage-inhibiting ADAM inhibitor. Inhibition of the cleavage of Her-2 in the first system can be identified using numerous methods of analysis, including those methods of identification of Her-2 cleavage/p95-ECD105 production set forth in detail elsewhere herein, followed by a differential comparison of the results obtained in the first and second experimental systems described immediately above. The presence of a lesser amount of p95 (or ECD105) in the putative ADAM inhibitor-containing system than in the system devoid of any putative ADAM inhibitor functions to inhibit the cleavage of Her-2 and the production of p95 by way of inhibition of ADAM10, 15, or both. By assessing the ability of the inhibitor to inhibit ADAM10 and ADAM15 separately, it can be further determined which ADAM is inhibited by the inhibitor and whether the inhibitor inhibits cleavage of Her-2 by both ADAMs.

One embodiment of the invention provides a method of inhibiting the cleavage of Her-2, wherein ADAM10 is the Her-2-cleaving agent. Inhibition of the ADAM10-mediated cleavage of Her-2 is confirmed using any method set forth herein for the analysis of the inhibition of Her-2 cleavage. Without wishing to be bound by any particular theory, inhibition of the ADAM10-mediated cleavage of Her-2 may occur in a number of ways. In one aspect of the invention, ADAM10 cleavage of Her-2 may be inhibited by an ADAM10 inhibitor that binds with ADAM10, thereby preventing the interaction of ADAM10 with Her-2 by preventing necessary contact of ADAM10 with Her-2. Alternatively, ADAM10 cleavage of Her-2 can be inhibited by an ADAM10 inhibitor that binds to ADAM10 and alters the structure of ADAM10, thereby inhibiting or reducing the interaction of ADAM10 with Her-2. Additionally, ADAM10 cleavage of Her-2 may be inhibited by an ADAM10 inhibitor that binds to ADAM10 and inhibits the proteolytic activity of ADAM10, thereby preventing proteolytic action of ADAM10 on Her-2.

Similarly, another embodiment of the invention provides a method of inhibiting the cleavage of Her-2, wherein ADAM15 is the Her-2-cleaving agent. Inhibition of the ADAM15-mediated cleavage of Her-2 is confirmed using any method set forth herein for the analysis of the inhibition of Her-2 cleavage. Without wishing to be bound by any particular theory, inhibition of the ADAM15-mediated cleavage of Her-2 may occur in a number of ways. In one aspect of the invention, ADAM15 cleavage of Her-2 may be inhibited by an ADAM15 inhibitor that binds with ADAM15, thereby preventing the interaction of ADAM15 with Her-2 by preventing necessary contact of ADAM15 with Her-2. Alternatively, ADAM15 cleavage of Her-2 can be inhibited by an ADAM15 inhibitor that binds to ADAM15 and alters the structure of ADAM15, thereby inhibiting or reducing the interaction of ADAM15 with Her-2. Additionally, ADAM15 cleavage of Her-2 may be inhibited by an ADAM15 inhibitor that binds to ADAM15 and inhibits the proteolytic activity of ADAM15, thereby preventing proteolytic action of ADAM15 on Her-2.

The invention is not limited to an inhibitor that affects ADAM to inhibit cleavage of Her-2. Instead, the invention includes an inhibitor that binds with Her-2 to inhibit cleavage of Her-2 by the ADAM, thereby inhibiting production of p95, p105 ECD, or both. Accordingly, another embodiment of the invention provides a method of inhibiting the ADAM10- or ADAM15-mediated cleavage of Her-2, wherein the interaction of ADAM10, ADAM15, or both, and Her-2 is prevented by way of an ADAM inhibitor that binds to Her-2. In yet another aspect of the invention, ADAM10 or ADAM15 cleavage of Her-2 may be inhibited by an ADAM10 or ADAM15 inhibitor that binds to Her-2, thereby preventing the interaction of ADAM10 or ADAM15 with Her-2 by preventing direct contact of ADAM10 or ADAM15 with Her-2. In another aspect of the invention, ADAM10 or ADAM15 cleavage of Her-2 may be inhibited by an ADAM inhibitor that binds to Her-2 and alters the structure of Her-2, thereby preventing the interaction of ADAM10, ADAM15, or both, with Her-2.

In an embodiment of the invention, the ADAM is a mammalian ADAM10. As will be understood by one of skill in the art, a mammalian ADAM10 may be present in a mammalian cell. Additionally, a mammalian ADAM10 may be present in a non-mammalian cell. For example, a method of the present invention includes a nucleic acid encoding a mammalian ADAM10 transformed or transfected into any non-mammalian cell known to one skilled in the art to be useful for expression of a non-native or exogenous proteins.

In an embodiment of the invention, the ADAM is a mammalian ADAM15. As will be understood by one of skill in the art, a mammalian ADAM15 may be present in a mammalian cell. Additionally, a mammalian ADAM15 may be present in a non-mammalian cell. For example, a method of the present invention includes a nucleic acid encoding a mammalian ADAM15 transformed or transfected into any non-mammalian cell known to one skilled in the art to be useful for expression of a non-native or exogenous proteins.

In some embodiments of the invention, the ADAM is a mammalian ADAM10 or a mammalian ADAM15. As will be understood by one of skill in the art, both mammalian ADAM10 and ADAM15 may be present in a mammalian cell. Additionally, both mammalian ADAM10 and ADAM15 can be present in a non-mammalian cell. For example, a method of the present invention includes introducing (e.g., co-transforming, co-transfecting, co-transducing, gene activation, and the like) a nucleic acid encoding a mammalian ADAM10 and a nucleic acid encoding a mammalian ADAM15 into any non-mammalian a cell known to one skilled in the art to be useful for expression of a non-native or exogenous proteins such that both ADAMs are present and expressed in the same cell where they were not previously present and/or expressed.

The present invention also features a method of inhibiting production of p95 by a cell. In an embodiment of the invention, a cell is contacted with a cleavage-inhibiting amount of an ADAM inhibitor, thereby inhibiting cleavage of Her-2 to produce p95. A "cleavage-inhibiting amount" of an inhibitor is defined herein as an amount of the inhibitor sufficient to produce a detectably lower level of p95 in cell expressing Her-2 when compared with the production of p95 by an otherwise identical cell not contacted with the compound or with the same cell prior to the cell being contacted with the compound.

The present invention also features a method of inhibiting production of p95 where the Her-2 is not associated with a cell. Methods of isolating, purifying, stabilizing, and solubilizing cell-associated proteins to exist unassociated with a cell are well known in the art, and will not be discussed further. One of skill in the relevant art will therefore know how to prepare and use Her-2 and ADAM10, ADAM15, or both, proteins where the proteins are not associated with an intact cell (e.g., solubilized, among other things) in accordance with the methods of the present invention.

In an embodiment of the invention, a Her-2 molecule is contacted with a cleavage-inhibiting amount of a inhibitor in a mixture comprising a sheddase (e.g., ADAM10, ADAM15, or both), thereby inhibiting cleavage of Her-2 to produce p95. A "cleavage-inhibiting amount" of a inhibitor is defined herein as an amount of the inhibitor sufficient to produce a lower level of p95 in a reaction mixture containing ADAM sheddase (ADAM10, 15, or both), Her-2, and the inhibitor, in comparison to the level of p95 in an otherwise identical reaction mixture that does not contain the inhibitor.

In an aspect of the invention, the inhibitor is an inhibitor of ADAM10, ADAM 15, or both, that binds with the ADAM, thereby preventing the interaction of ADAM10, 15, or both, with Her-2 by preventing direct contact of ADAM10, ADAM15, or both, with Her-2. In another aspect of the invention, the cleavage inhibitor is an ADAM10, ADAM15, or both, inhibitor that binds to ADAM10, ADAM15, or both, and alters the structure of ADAM10, ADAM15, or both, thereby preventing the interaction of ADAM10, ADAM15, or both, with Her-2. In yet another aspect of the invention, the cleavage inhibitor is an ADAM10, ADAM15, or both, inhibitor that binds to ADAM10, ADAM15, or both, and inhibits the proteolytic activity of ADAM10, ADAM15, or both, thereby preventing proteolytic action of ADAM10, ADAM15, or both, on Her-2. In yet another aspect of the invention, the cleavage inhibitor is an ADAM10, ADAM15, or both, inhibitor that binds to Her-2, thereby preventing the interaction of ADAM10, ADAM15, or both, with Her-2 by preventing direct contact of ADAM10, ADAM15, or both, with Her-2. In still another aspect of the invention, the cleavage inhibitor is an ADAM10, ADAM15, or both, inhibitor that binds to Her-2 and alters the structure of Her-2, thereby preventing the interaction of ADAM10, ADAM15, or both, with Her-2.

The present invention also features a cleavage inhibitor that is an inhibitor of the proteolytic activity of ADAM10, ADAM15, or both. Compounds having the ability to inhibit protease activity, i.e., protease inhibitors, are well-known in the art, and accordingly, one of skill in the art would recognize and know how to produce and use a compound that is a protease inhibitor that is specific for an ADAM of interest, e.g., ADAM10, ADAM15, and the like.

Nucleic Acid-Based Methods Relating to Inhibiting Her-2 Cleavage by ADAM10 and ADAM15

The skilled artisan would appreciate, based upon the disclosure provided herein, that the present invention encompasses inhibition of a Her-2-mediated signal otherwise transmitted via a Her-2 receptor that was cleaved by an ADAM by preventing cleavage of the Her-2 receptor by the ADAM. That is, the data disclosed herein demonstrate that ADAM (e.g., ADAM10, ADAM15, or both) cleave Her-2 to produce p95 and the p95 so produced, in turn, transmits a signal. The data further demonstrate that inhibition of production of p95, and thus, inhibition of transmission of a signal via the constitutively active p95, mediates a number of effects, including, but not limited to, decreased phosphorylation of certain proteins, decreased cell proliferation, induction of cell death, and the like. Thus, where these effects are desired, a wide plethora of methods for inhibiting signaling via the p95 stub can be used to mediate the desired effect, especially where the cell mediates a disease, disorder or condition, such as, but not limited to cancer.

The skilled artisan would further understand, once armed with the teachings provided herein, that the present invention includes administering a ribozyme or an antisense nucleic acid molecule to a cell thereby inhibiting expression of ADAM10, 15, or both, in the cell, where the design and use of such molecules to inhibit expression of a protein of interest in a cell are well-known in the art as follows briefly. That is, the data disclosed herein demonstrate that inhibition of expression of an mRNA encoding an ADAM that cleaves Her-2 to produce ECD, p95, or both, decreases the cleavage of Her-2. Further, any method that decreases the level of an ADAM that cleaves Her-2 mediates such an effect as would be readily appreciated by the skilled artisan based upon the disclosure provided herein and such method is encompassed by the invention.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules can be produced synthetically and then provided to the cell. Antisense oligomers of between about 10 to about 100, and more preferably about 15 to about 50 nucleotides, are preferred, since they are easily synthesized and introduced into a target cell. Synthetic antisense molecules contemplated by the invention include oligonucleotide derivatives known in the art which, have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which, are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In certain situations, it may be desirable to inhibit expression of ADAM10, ADAM15, or both, and the invention therefore includes compositions useful for inhibition of ADAM10, ADAM15, or both, expression. Thus, the invention features an isolated nucleic acid complementary to a portion or all of a nucleic acid encoding a mammalian ADAM10, 15, or both, which nucleic acid is in an antisense orientation with respect to transcription. Preferably, the antisense nucleic acid is complementary with a nucleic acid having at least about 90% homology with ADAM10, 15, or both. Preferably, the nucleic acid is about 95% homologous, more preferably, about 96% homologous, more preferably, about 98% homologous, and most preferably, about 99% homologous to a nucleic acid complementary to a portion or all of a nucleic acid encoding a mammalian ADAM10, 15, or both, or a fragment thereof, which is in an antisense orientation with respect to transcription. Most preferably, the nucleic acid is complementary to a portion or all of a nucleic acid having the sequence, or a fragment thereof, of a sequence known to encode ADAM10, ADAM15, or both. Such antisense nucleic acid serves to inhibit the expression, function, or both, of ADAM10, ADAM15, or both.

In one embodiment, the present invention features a method of inhibiting cleavage of Her-2, whereby the ADAM-mediated cleavage of Her-2 is inhibited by contacting a cell with a Her-2 cleavage-inhibiting amount of an ADAM-directed antisense nucleic acid. One skilled in the art would appreciate, based on the disclosure provided herein, that an antisense ADAM inhibitor of the invention includes molecules and compounds that prevent or inhibit ADAM10, ADAM15, or both, from being accessible to Her-2 on the cell surface. That is, the invention contemplates that an antisense and/or antisense molecule that prevents the expression of ADAM10, ADAM15, or both, such that Her-2 is not cleaved to form p95 can be an inhibitor of the invention.

In an aspect of the invention, an ADAM inhibitor is an siRNA. Small interfering RNAs (siRNA) mediate a process of post-transcriptional gene silencing called RNA interference (RNAi) in which the siRNAs directs sequence specific cleavage and degradation of cellular mRNA targets to which the siRNA has sequence identity (Tuschl, 2002 Nature Biotech. 20:446-448; Sharp, 2001, Genes Dev. 15:485-490). The siRNAs may be double-stranded synthetic RNAs of 19 to 21 nucleotides with a 2 to 3 nucleotide 3' overhang or they may be expressed as short hairpin RNAs (shRNA), in which the individual sense and antisense strands are joined by a tightly-structured loop, from plasm ids or viral vectors harboring both RNA polymerase III promoter and terminator sequences (Elbashir et al., 2001, Nature 411:494-498; Paul et al., 2002, Nature Biotech. 20:505-508; Paddison et al., 2002, Proc. Natl. Acad, Sci. USA 99:1443-1448). As described in detail in Tuschl et al. and Sharp, incorporated herein by reference in their entirety, and as understood by one of skill in the art, siRNA can be used to knockdown expression of a Her-2 cleaving ADAM (i.e., ADAM10, 15, or both) in a cell. Therefore, the present invention encompasses administering to a Her-2-expressing cell a Her-2 cleavage inhibiting amount of an ADAM inhibitor where the inhibitor is an siRNA. In an embodiment of the invention, the siRNA is directed to ADAM10 RNA, ADAM15, RNA, or both. In one aspect, the ADAM-directed siRNA is comprised of a double-stranded RNA, of which a single strand is complementary to ADAM10 RNA, ADAM15, RNA, or both. The present invention is not limited to any particular siRNA; rather, the invention encompasses a wide plethora of siRNAs having the ability to inhibit cleavage of Her-2 by ADAM10, ADAM15, or both. Indeed, the siRNAs disclosed herein were commercially available, demonstrating that production of such siRNAs is routinely performed in this art where the level of skill is high.

The present invention includes a nucleic acid useful in inhibiting cleavage of Her-2 by an ADAM10, an ADAM15, or both. That is, the data disclosed herein demonstrate that the expression of a Her-2 cleaving ADAM, e.g., ADAM10, ADAM15, and the like, can be knocked down, or decreased, using a siRNA complementary to the mRNA encoding the pertinent ADAM. Inhibition of ADAM mRNA using an siRNA specific for that ADAM mediated, in turn, a decrease in Her-2 cleavage and, even more importantly, also mediated a decrease in Her-2 shedding. Because the data disclosed herein further demonstrate that inhibition of Her-2 shedding inhibits cell proliferation, induces cell death, and can mediate a beneficial effect in a patient afflicted with a Her-2 overexpressing tumor, inhibition of ADAM expression using an siRNA can provided an important potential therapeutic for a disease, disorder or condition associated with, or mediated by, Her-2 cleavage, including such disease, disorder or condition that is mediated by or associated with production of p95 in a cell.

As pointed out elsewhere herein, these nucleic acids are useful in that they can inhibit ADAM activity in a cell. Many metalloproteases are highly expressed in tumor cells. As ADAM protease activity regulates the shedding of autocrine growth factors or their receptors, these proteins mediate the growth, adhesion or motility of tumor cells. ADAM10 is overexpressed in pheochromocytoma and neuroblastomas (Yavari et al., 1998 Hum. Mol. Genet. 7:1161-67). Moreover ADAM10 has been demonstrated through both genetic and biochemical experiments to be involved in the shedding of both Notch receptor and its ligand Delta. Genetic analyses of ADAM10 knockout mice or flies harboring loss of function mutations in the Drosophila ortholog Kuzbanian, show strikingly similar phenotypes as loss of function mutations in the notch and delta. Importantly, expression of the Notch target gene hes-5 in the neural tube of ADAM10 knockout mice was significantly reduced with a concomitant upregulation of the notch ligand dll-1, a gene that is negatively regulated by feedback Notch signaling (Seals and Courtneidge, 2003, Genes Dev. 17:7-30; Hartmann et al., 2002, Hum. M. Genet. 11:2615-24).

Notch can function as an oncogene in mouse and humans. In T-cells, for example, chromosomal relocation or viral integrations that lead to expression of a constitutively active cytoplasmic domain of Notch1 cause T-cell acute lymphoblastic leukemia (Radtke and Raj, 2003, Nat. Rev. Cancer. 3:756-67). Notch receptors and Notch ligands are also highly expressed in colon adenocarcinomas and breast cancers where Notch signaling may contribute to Her-2 overexpression. Notch is also important in angiogenesis, and the ADAM10 knockout mice exhibit defective vasculogenesis similar to notch knockout mice (Hartmann et al., 2002, Hum. Mol. Genet. 11:2615-24). Another ligand that is implicated in many tumor types is epidermal growth factor; recent evidence indicates that ADAM10 and its metalloprotease activity is required for cleavage of heparin binding EGF and the transactivation of EGFR signaling in response to G-protein coupled receptor activation (Yan et al., 2002. J. Cell Biol. 2002. 158:221-6). Therefore, the biological activity of ADAM10 is crucial in a number of cell processes and the skilled artisan would appreciate that inhibition of its function(s) can have useful effect(s).

Among the many uses illustrating the potential usefulness of inhibiting ADAM15 activity is the fact that ADAM15 activity is important for the migration of mesangial cells (MC) from the core of the renal glomerulus. Migration of these cells from the core to the pericapillary space is a feature of a number of renal diseases including mesangiocapillary glomerulonephritis. In a model of MC wounding, ADAM15 expression was increased and it was correlated with the mobility of these cells. MMP inhibitors, or antisense oligonucleotides, to ADAM15 reduced this migration indicating that inhibition of ADAM15 activity may have beneficial effects in disease characterized by MC motility (Martin et al., 2002, J. Biol. Chem. 277:33683-33689). In addition, ADAM15 knockout mice implanted with melanoma cells showed reduced tumor size (Horiuchi et al., Mol. Cell. Biol. 2003, 5614).

The nucleic acid, when administered to a cell expressing Her-2, detectably inhibits ADAM activity. More preferably, the nucleic acid detectably inhibits ADAM expression, even more preferably, it inhibits Her-2 cleavage, yet more preferably, the nucleic acid inhibits production of p95 in the cell, when compared with the level of p95 production in an otherwise identical cell to which the nucleic acid is not administered, and/or to the level of p95 in the cell prior to administration of the nucleic acid. Additionally, the nucleic acid can, but need not, induce cell death, inhibit cell proliferation, inhibit signaling via the Her-2 receptor, and the like.

Antisense nucleic acids that inhibit expression of ADAM10, 15, or both, can also be used for the manufacture of a medicament for treatment of a disease, disorder or condition mediated by increased expression of Her-2 receptor when compared with expression of Her-2 receptor in a cell and/or a patient not afflicted with the disease, disorder or condition.

Techniques for inhibiting expression of a nucleic acid in a cell are well known in the art and encompass such methods as disclosed herein (e.g., inhibition using an antibody, an antisense nucleic acid, an siRNA, a ribozyme, and the like). Other techniques useful for inhibiting expression of a nucleic acid encoding ADAM10, 15, or both, include, but are not limited to, using nucleotide reagents that target specific sequences of the receptor promoter, and the like.

The skilled artisan would understand, based on the disclosure provided herein, that cleavage of a Her-2 receptor present in a cell can be inhibited or abrogated using a nucleic acid that prevents expression of ADAM10, ADAM15, or both, in the cell. As more fully set forth elsewhere herein, once the nucleic and amino acid sequences of a Her-2 cleaving ADAM is known, various methods well-known in the art can be used to inhibit cleavage of Her-2 to form p95. Such methods include, but are not limited to, antibodies, siRNAs, ribozymes, and antisense molecules. The design and use of such compounds is well established once the skilled artisan is armed with the sequence of the nucleic acid encoding ADAM10, ADAM15, or both, such as disclosed herein where the data demonstrate which ADAMs mediate cleavage of Her-2 (e.g., ADAM10, and ADAM15), and such methods are therefore not recited herein as they are well known in the art. For instance, designing antisense molecules and ribozymes can effectively inhibit progression of breast cancer by inhibiting expression of ADAM10, ADAM15, or both, which, in turn, inhibits Her-2 cleavage and production of p95, without affecting expression of other ADAM family members, which may be required for proper cell function. Thus, selective targeting of the Her-2 cleaving ADAMs, while not affecting the function of other ADAMs, can avoid deleterious effects of non-specifically inhibiting cell growth, and other cell processes.

Where an antisense nucleic acid directed to ADAM10, ADAM15, or both, is administered to a cell to reduce the level of ADAM10, ADAM15, or both, present in the cell, one skilled in the art would understand, based upon the disclosure provided herein, that the amount of the nucleic acid to be administered to the cell can be titrated by assessing the expression level of nucleic acid encoding ADAM10, ADAM15, or both, present in the cell.

Methods for assessing the level of ADAM10, ADAM15, or both, expression (e.g., using anti-receptor antibodies in Western blot or other immune-based analyses such as ELISA) and/or methods for assessing the level of ADAM10, ADAM15, or both, expression in a cell and/or tissues (e.g., using Northern blot analysis, qPCR, and the like) are disclosed herein or are well known to those skilled in the art. Such assays can be used to determine the "effective amount" of ADAM10, ADAM15, or both, antisense nucleic acid, ribozyme, and the like, to be administered to the cell in order to reduce or increase the level of ADAM10, ADAM15, or both, expression. The amount of nucleic acid administered can be easily calculated and adjusted as exemplified herein for siRNA that reduced expression of ADAM10 and ADAM15, and concomitantly reduced Her-2 cleavage and sheddase mediated shedding of ECD. However, the present invention is not limited to these, or any other, assay in particular for determining an effective amount of an inhibitor, including a nucleic acid-based inhibitor such as, but not limited to, siRNA.

Similarly, an antibody, or a nucleic acid, that specifically binds with a Her-2 cleaving ADAM (ADAM10, ADAM15, or both), can be administered to a cell thereby inhibiting Her-2 cleavage by that ADAM. The production and use of "intrabodies", as such antibodies are referred to in the art, is well known, and is therefore not discussed further herein. The skilled artisan, armed with the teachings provided herein, especially that certain ADAMs mediate cleavage of Her-2 to produce p95, would readily appreciate that intrabodies, among many other molecules, can be used to inhibit ADAM cleavage of Her-2.

Metalloprotease Inhibitors (MPIs)

ADAM inhibitors of the present invention include small molecules referred to herein as metalloprotease inhibitors (MPIs). An MPI according to the invention is capable of inhibiting (e.g., antagonizing) the activity of an ADAM. In some embodiments, the MPI inhibits the activity of ADAM10, ADAM15, or both. In further embodiments, the ADAM activity that is inhibited by the MPI is the cleavage of a kinase receptor such as, for example, Her-2. The MPI can also modulate the activity of other biological receptors including, for example, matrix metalloproteases (MMPs). In some embodiments, the MPI inhibits the activity of one or more MMPs including, for example, MMP1, MMP2, MMP3, MMP7, MMP8, MMP9, MMP10, MMP12, MMP13, MMP14 and/or other MMPs. The MPI can further be selective for ADAM. By "selective for ADAM" is meant that the MPI is a more effective inhibitor (e.g., has a lower $IC_{50}$) of an ADAM than of other metalloproteases (e.g., MMPs). In some embodiments, the MPI is further selective for ADAM10 or ADAM15; that is, the MPI is a more effective inhibitor of ADAM10 or ADAM15 than of other metalloproteases including other ADAMs. In some further embodiments, an MPI selective for an ADAM is about 100-fold, about 50-fold, about 20-fold, about 10-fold, about 6-fold, about 5-fold, about 3-fold, or about 2-fold more active for inhibition of the ADAM than for any MMP (e.g., as measured by $IC_{50}$). In yet further embodiments, the MPI is at least about 2-fold selective for an ADAM over any MMP.

Numerous compounds have been prepared that are metalloprotease inhibitors and can be MPIs useful in the methods of the invention. The following patents describe some example MPIs that can be useful according to the methods of the present invention: U.S. Pat. Nos. 6,706,723; 6,703,415; 6,703,379; 6,696,456; 6,696,449; 6,689,794; 6,689,771; 6,686,348; 6,683,155; 6,683,093; 6,683,060; 6,677,355; 6,677,321; 6,667,388; 6,667,316; 6,660,738; 6,656,954; 6,656,448; 6,642,255; 6,638,952; 6,624,196; 6,624,177; 6,624,144; 6,620,835; 6,620,823; 6,620,813; 6,608,104; 6,605,742; 6,583,299; 6,579,982; 6,579,890; 6,576,628; 6,569,899; 6,569,855; 6,566,381; 6,566,116; 6,563,002; 6,559,142; 6,555,535; 6,548,667; 6,548,524; 6,545,038; 6,544,980; 6,541,638; 6,541,521; 6,541,489; 6,534,491; 6,511,993; 6,506,764; 6,500,948; 6,500,847; 6,495,699; 6,495,578; 6,495,565; 6,492,422; and 6,492,367, the disclosures of each of which are incorporated herein by reference in their entirety. The preceding listing represents only some of the numerous possible MPIs known in the art, and one skilled in the art would readily understand that the methods of the invention are not limited to the compounds explicitly referred to herein.

In some embodiments, the MPI is a compound having at least one hydroxamic acid moiety. Hydroxamate compounds, their preparation, and their use as metalloprotease inhibitors are well established in the art as illustrated by the numerous patent references listed above and, e.g., Muri, et al. "Hydroxamic acids as pharmacological agents." Curr. Med. Chem. 2002 September; 9(17):1631-53, which is incorporated herein by reference in its entirety.

Further hydroxamate compounds suitable as MPIs include any of those referred to above as well as those described in, for example, WO 03/051825; WO 03/106381; U.S. Ser. No. 60/534,501; US. Ser. No. 60/512,016; and U.S. Ser. No. 60/515,352, each of which is incorporated herein by reference in its entirety.

Further hydroxamate compounds suitable as MPIs include the following: Compounds 1, 2, 3, 4, 5, 7, and 8 (see Examples for compound identities); as well as (6S,7S)-N-hydroxy-5-methyl-6-[(4-phenylpiperidin-1-yl)carbonyl]-5-azaspiro[2.5]octane-7-carboxamide, (6S,7S)-N-hydroxy-5-methyl-6-[(4-phenyl-3,6-dihydropyridin-1(2H)-yl)carbonyl]-5-azaspiro[2.5]octane-7-carboxamide, (6S,7S)-N-Hydroxy-6-{[(3-phenylpyrrolidin-1-yl]carbonyl}-5-azaspiro[2.5]octane-7-carboxamide, (6S,7S)-N-hydroxy-6-((4-(methylsulfonyl)phenyl)-3,6-dihydropyridin-1(2H)-yl)carbonyl)-5-azaspiro(2,5)octane-carboxamide, (2S,3S)-N-hydroxyl-1-methyl-2-((10aS)-3,4, 10,10a-tetrahydropyrazino(1,2-a) indol-2(1H)-yl-carbonyl)piperidine-3-carboxamide, (6S,7S)-N-hydroxy-6-((10aS)-3, 4,10,10a-tetrahydropyrazino(1,2-a)-indol-2(1H)-yl-carbonyl)-5-azaspiro(2,5)octane-7-carboxamide, (6S,7S)-N-hydroxy-6-((4-(3-(methylsulfonyl)phenyl)-3,6-dihydropyridin-1(2H)-yl)carbonyl)-5-azaspiro(2,5)octane-7-carboxamide, methyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate, benzyl (6S, 7S)-7-[(hydroxyamino)carbonyl]-6-[(4-phenyl-3,6-dihydropyridin-1(2H)-yl)carbonyl]-5-azaspiro[2.5]octane-5-carboxylate, (6S,7S)-N-Hydroxy-5-(methylsulfonyl)-6-[(4-phenyl-3,6-dihydropyridin-1(2H)-yl)carbonyl]-5-azaspiro[2.5]octane-7-carboxamide, and (6S,7S)-N-hydroxy-6-{[4-(3-methoxyphenyl)piperidin-1-yl]carbonyl}-5-methyl-5-azaspiro[2.5]octane-7-carboxamide, each of which can be prepared according to the methods described in U.S. Ser. No. 60/534,501, which is incorporated herein by reference in its entirety.

Further MPIs useful according to the methods of the present invention include TAPI, prinomastat, batimastat, marimastat, tanomastat, BMS-275291, and CGS27023A, each of which are known as or have been in clinical development as a metalloprotease inhibitor.

MPIs suitable for use according to the methods of the present invention can be identified by any of numerous known assays testing for inhibitory activity of an ADAM. Example assays useful for identifying ADAM10 and ADAM15 inhibitors are provided below.

ADAM10 Assay 5 mM Compound stock was prepared in DMSO. Compound plate was prepared by 2-fold dilution for 11-point curve, with highest concentration of 500 µM. 1 µL of compound in DMSO was transferred from compound plate to the assay plate. Enzyme solution was prepared in assay buffer with a concentration of 100 ng/50 µL. Substrate ((7-methoxycoumarin-4-yl)-acetyl-Pro-Leu-Ala-Gln-Ala-Val-(3-[2,4-dinitrophenyl]-L-2,3-diaminopropionyl)-Arg-Ser-Ser-Ser-Arg-$NH_2$ (SEQ ID NO:48)) solution was prepared in assay buffer with a concentration of 20 µM. 50 µL of enzyme solution was added to the assay plate. The assay plate was incubated for 5 minutes. 50 µL of substrate solution was then added to the assay plate. The plate was protected from light and incubated at 37° C. for 4 hours. The reaction was stopped by adding 10 µL of 500 mM EDTA solution. The plate was read on a plate reader with excitation of 320 nm and emission of 405 nm.

ADAM15 Assay

ADAM15 can be assayed in a similar fashion to ADAM10 (see, e.g., Fourie et al., J Biol Chem. 2003, 278(33), 30469-77). In brief, a fluorescence quenched peptide substrate is made by labeling one terminus with a fluorescent dye and the other terminus with a quencher dye. Cleavage of the peptide by ADAM15 can be measured by the increase in fluorescence intensity as a result of the decrease in proximity of the quencher dye to the fluorescent dye.

Methods in a Cell

The present invention provides numerous methods of inhibiting cleavage of Her-2 in a cell comprising Her-2, whereby an ADAM inhibitor (e.g., ADAM10 and/or ADAM15 inhibitor) is administered to a cell. As set forth in detail elsewhere herein, the cleavage of Her-2 produces p95 and ECD105, and based on the data disclosed for the first time herein, p95 is implicated in subsequently playing a role in the development and progression of cancer. Therefore, one of skill in the art would understand, based on the disclosure herein, that inhibition of the cleavage of Her-2 will repress the production of p-95. The repression of p95 production is useful for the prevention of any conditions or disorders associated with increased Her-2/p95 signaling. For example, as disclosed in detail elsewhere herein, overexpression of Her-2 occurs in 25-30% of breast cancers. Patients with Her-2 overexpressing tumors have a distinctly unfavorable clinical course, characterized by shortened time to disease recurrence and reduced survival. Therefore, the repression of p95 production will inhibit and/or decrease Her-2/p95-based signaling, subsequently minimizing the unfavorable clinical course of Her-2/p95-mediated disease.

In some embodiments of the invention, the growth of a tumor cell overexpressing Her-2 is affected. In the method, a Her-2 overexpressing cell is contacted with a Her-2 cleavage-inhibiting amount of an ADAM inhibitor, inhibiting cleavage of and thereby inhibiting growth of a cell overexpressing Her-2. ADAM inhibitors are discussed in greater detail elsewhere herein. In some embodiments of the invention, the growth of a tumor cell is inhibited.

The present invention also provides methods for affecting any cell expressing Her-2. Such methods affect a Her-2-expressing cell by way of ADAM whereby the interaction between the ADAM and Her-2 is enhanced or inhibited, thereby affecting the ADAM-mediated cleavage of Her-2. Because the cleavage of Her-2 by ADAM produces p95, which is believed to play a role in cell growth and differentiation, methods affecting a Her-2-expressing cell by way of ADAM whereby the interaction between ADAM and Her-2 is enhanced or inhibited, are useful for stimulating or inhibiting cell growth and/or differentiation. This effect is especially useful in a cell where there is underexpression of Her-2, and/or where greater expression of Her-2, increased level of p95, or greater ADAM expression or function is desired as would be understood by the skilled artisan based upon the disclosure provided herein.

The invention also includes methods of affecting the growth of a cell overexpressing Her-2. In the method, a Her-2 overexpressing cell is contacted with a Her-2 cleavage-inhibiting amount of an ADAM inhibitor, inhibiting production of p95, and thereby inhibiting growth of a cell overexpressing Her-2. ADAM inhibitors are discussed in greater detail elsewhere herein, and based on the disclosure herein, one of skill in the art will understand that an ADAM inhibitor of the invention may inhibit the ADAM-mediated cleavage of Her-2 by interacting with ADAM, Her-2, or both.

In another embodiment of the invention, the proliferation of a cell overexpressing Her-2 is affected. In the method, a Her-2 overexpressing cell is contacted with a Her-2 cleavage-inhibiting amount of an ADAM inhibitor, inhibiting cleavage of Her-2 by ADAM and thereby inhibiting proliferation of a cell overexpressing Her-2. Such method is useful for inhibition of proliferation of tumor cells because these cells can overexpress Her-2 while normal, non-tumor cells, typically do not. In this way, the invention provides a selective method for inhibiting tumor cell growth while not affecting normal cells which would otherwise be affected by anti-tumor methods.

The present invention also provides a method of inducing the death of a Her-2 overexpressing cell. In the method, a Her-2 overexpressing cell is contacted with a Her-2 cleavage-inhibiting amount of an ADAM inhibitor, inhibiting cleavage of Her-2 by ADAM and thereby inducing death of a cell overexpressing Her-2. Such methods would be useful where not only inhibition of proliferation is desired, but where cells that are present, but may no longer be proliferating, are to be destroyed.

The invention also provides a method for inhibiting signal transduction in a cell, wherein the signal transduction is mediated via a Her-2 receptor on a Her-2 overexpressing cell. The method of the invention comprises contacting a Her-2 overexpressing cell with a Her-2 cleavage-inhibiting amount of an ADAM inhibitor. Inhibition of the ADAM-mediated cleavage of Her-2 inhibits a signal transduction pathway that is mediated by the Her-2 receptor. This is because the production of p95, which is a constitutively-active kinase which constitutively transmits the signal otherwise non-constitutively regulated via the Her-2 receptor, is inhibited. In some embodiments, a mitogen-activated protein (MAP) kinase pathway is inhibited. In some embodiments, a protein kinase B (AKT) pathway is inhibited.

In yet another aspect of the invention, the phosphorylation of an extracellular signal-regulated kinase (ERK) is inhibited, leading to inhibition of a Her-2 receptor-mediated signal transduction pathway. In another aspect of the invention, the phosphorylation of a protein kinase B (AKT) is inhibited, leading to inhibition of a Her-2 receptor-mediated signal transduction pathway. This is because the data disclosed herein demonstrate that these various pathways are regulated by transduction of a signal via the Her-2 receptor. Thus, by inhibiting transduction of a signal via a Her-2 receptor by inhibiting production of the constitutive signal transducing portion of Her-2, i.e., p95, inhibition of the downstream pathways can be effected. Since p95 upregulates these pathways, inhibiting p95 will downregulate them such that the present invention provides effective methods for doing so.

The present invention also provides a method of inhibiting tumor growth of a Her-2 overexpressing tumor. In the method, a Her-2 overexpressing tumor is contacted with an effective amount of an ADAM inhibitor. Such methods would be useful in the treatment of cancer.

Methods of Treatment

The present invention provides a method for the treatment of cancer by administering to a patient afflicted with the cancer, or likely to be afflicted with the cancer, a therapeutically effective amount of an ADAM inhibitor. Further provided herein are methods of treating cancer in a patient by inhibiting cleavage of Her-2 expressed in the cancer. Further provided herein are methods of treating cancer in a patient by inhibiting formation of p95 in the cancer. The present invention further provides methods of treating cancer in a patient by inhibiting the Her-2 cleaving activity of an ADAM expressed in the cancer.

The present invention further provides a method for inhibiting metastasis of cancer by administering to a patient afflicted with the cancer a therapeutically effective amount of an ADAM inhibitor. Further provided herein are methods for inhibiting metastasis of cancer in a patient by inhibiting cleavage of Her-2 expressed in the cancer. Further provided herein are methods of inhibiting metastasis of cancer in a patient by inhibiting formation of p95 in the cancer. The present invention further provides methods of inhibiting metastasis of cancer in a patient by inhibiting the Her-2 cleaving activity of an ADAM expressed in the cancer.

The present invention further provides a method for inhibiting tumor growth by administering to a patient afflicted with the tumor a therapeutically effective amount of an ADAM inhibitor. Further provided herein are methods for inhibiting tumor growth in a patient by inhibiting cleavage of Her-2 expressed in the tumor. Further provided herein are methods for inhibiting tumor growth in a patient by inhibiting formation of p95 in the tumor. The present invention further provides methods for inhibiting tumor growth in a patient by inhibiting the Her-2 cleaving activity of an ADAM expressed in the tumor.

In some embodiments, the ADAM inhibitor is an inhibitor of ADAM10 or ADAM15. In further embodiments, the ADAM inhibitor is an MPI. In yet further embodiments, the ADAM inhibitor is an MPI that is selective for an ADAM. In yet further embodiments, the ADAM inhibitor is an MPI that is selective for ADAM10 or ADAM15.

In some embodiments, the ADAM inhibitor inhibits cleavage of Her-2 in vivo.

In some embodiments, the ADAM inhibitor is administered in combination with a further pharmaceutical agent such as an antibody, antiproliferative agent, or cytoxin. Example antibodies include anti-Her-2 antibodies such as Herceptin™ (Trastuzumab), 2C4, 4D5, HER-50, HER-66, HER-70 (available from Genentech or UT Southwestern Medical School) and the like. Example antibodies further include anti-EGFR-1 antibodies including, for example, IMC-C225 (Imclone), ABX-EGF (Abgenix), and the like. Further example antibodies include anti-VEGF antibodies. Example antiproliferative agents include epidermal growth factor inhibitors (e.g., OSI-774 (OSI/Genetech), PKI-116 (Novartis), or EKB-569 (Wyeth)), Her-2 inhibitors (e.g., CP-6545777 (Pfizer) or GW572016 (Glaxo Smith Kline)), dual EGFR-1/Her-2 inhibitors (GW2016 (GlaxoSmithKline) or C1-1033 (Pfizer)), Met kinase inhibitors, MEK-1 kinase inhibitors, MAPK kinase inhibitors, PI3 inhibitors, Src kinase inhibitors, PDGF inhibitors, inhibitors of integrin signaling, and inhibitors of insulin-like growth factor receptors, and small molecules such as ZD6474 and SU6668. Example cytotoxins include chemotherapeutics such as Taxol™, Cisplatin™ and the like. Other suitable antibodies, antiproliferative agents and cytotoxins are provided elsewhere herein.

Cancers treatable by this method include those that overexpress Her-2. In some embodiments, treatable cancers include those that overexpress Her-2 and exhibit Her-2 cleavage to form p95 and free extracellular domain (ECD). Non-limiting examples of cancers include breast cancer, ovarian cancer, pancreatic cancer, non-small cell lung cancer, colon cancer, prostate cancer, gastric cancer, glioma, and the like. In some embodiments, the cancer is breast cancer.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound (e.g., MPI) that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

As used herein, the phrase "in combination with" means that the two or more pharmaceutical agents are administered either at the same time or within at least about 24 hours, preferably at least about 12 hours, more preferably, at least about 6 hours, even more most preferably, at least about 3 hours, yet more preferably, about 1 hour, and even more preferably, less than about 1 hour.

Pharmaceutical Formulations and Dosage Forms

When employed as pharmaceuticals, MPIs can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more MPIs in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The ply of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods of Identifying a Useful Compound Relating to Inhibiting Cleavage of Her-2 by ADAM10 and ADAM15

The present invention also includes a method of identifying a compound capable of affecting the interaction of ADAM10, 15, or both, with Her-2. The method comprises contacting a first reaction mixture containing Her-2 and an ADAM10, 15, or both, with a test compound, then assaying the first reaction mixture for the appearance of p95. A lower level of p95 in the first reaction mixture, when compared with a second reaction mixture containing Her-2 and ADAM10, 15, or both, without the test compound, is indicative of a compound capable of affecting the interaction of ADAM10, 15, or both, with Her-2. Such a compound is defined herein as inhibiting the interaction of ADAM10, 15, or both, with Her-2, as the lower level of p95 is indicative of a decreased proteolysis of Her-2 by ADAM. The invention includes any compound identified by the methods disclosed herein.

The invention encompasses a method of identifying a compound that inhibits cleavage of Her-2. The method comprises contacting an ADAM with a test compound in a mixture comprising a known ADAM substrate. Such substrates are well known in the art and include various peptides known to be cleaved by ADAM under known reaction conditions. Thus, one skilled in the art, based upon the disclosure provided herein, would appreciate that since it is now known, for the first time, that ADAM10 and ADAM15 specifically cleave Her-2, the ability of a test compound to inhibit cleavage of Her-2 can be assayed by assessing the ability of the compound to inhibit the cleavage of a known substrate by either one, or both, of these ADAMs. Therefore, a wide plethora of art-recognized assays for assessing the activity of ADAM10, ADAM15, or both, can be used to identify a useful compound that can inhibit cleavage of Her-2 by those enzymes. More specifically, the cleavage of a known ADAM (10, 15 or both) can be assessed in the absence of a test compound. The cleavage of the same substrate can be assessed, under identical conditions, in the absence of the test compound. The cleavage of the substrate in the presence or absence of the compound can then be compared. One skilled in the art would understand that where there is detectably less cleavage of the substrate in the presence of the compound compared with the level of cleavage of the substrate in the absence of the compound, the compound inhibits ADAM cleavage of its substrate. Accordingly, the skilled artisan would appreciate, armed with the teachings provided herein, that because the data disclosed herein demonstrate that ADAM, more specifically, ADAM10 and ADAM15, mediate cleavage of Her-2, a substance that inhibits cleavage of a substrate by ADAM10, ADAM15, or both, will also inhibit cleavage of Her-2 by ADAM10. ADAM15, or both. Thus, the invention encompasses a useful assay for identifying useful inhibitors of Her-2 cleavage. These compounds are useful in that it is known that Her-2 cleavage by ADAM mediates a deleterious effect, most likely mediated by the production of the p95 portion of Her-2. Without wishing to be bound by any particular theory, regardless of the mechanism whereby inhibition of Her-2 cleavage mediates various effects on cellular processes, as demonstrated by the data disclosed herein, the usefulness of a compound that inhibits cleavage of Her-2 mediated by ADAM10, ADAM15, or both, is amply demonstrated by the data disclosed herein. The invention encompasses a compound identified using this method.

The present invention also includes a method of identifying a compound capable of affecting the interaction of ADAM10, 15, or both, with Her-2. The method comprises contacting a first reaction mixture containing Her-2 and ADAM with a test compound, then assaying the first reaction mixture for the appearance of ECD105. A lower level of ECD105 in the first reaction mixture, when compared with a second reaction mixture containing Her-2 and ADAM10, 15, or both, without the test compound, is indicative of a compound capable of affecting the interaction of ADAM10, 15, or both, with Her-2. Such a compound is defined herein as inhibiting the interaction of ADAM10, 15, or both, with Her-2, as the lower level of ECD105 is indicative of a decreased proteolysis of Her-2 by ADAM10, 15, or both. The invention includes any compound identified by the methods disclosed herein.

In an embodiment of the invention, compounds capable of inhibiting the ADAM10, 15, or both, -mediated cleavage of Her-2 to form p95 and ECD105 are identified. A person skilled in the art will realize, based upon the disclosure provided herein, that purified full-length ADAM10 or ADAM15, truncated forms of ADAM10 or ADAM15 retaining the metalloprotease domain, or conditioned media containing soluble forms of recombinant ADAM10 or ADAM15 that retain the metalloproteinase domains, can be assayed using any of a variety of protease assays. ADAM10 or ADAM15 can be assayed through the use of peptide substrates encompassing the natural cleavage site of Her-2 or other known substrates for sheddases, including but not limited to: APP, Notch, delta, TNF-alpha, TGF-alpha, HB-EGF, CSF-1, nerve growth factor receptor, hepatocyte growth factor receptor Met, neuregulin, fractalkine, collagen and gelatin. Assay formats for detecting cleavage of a substrate by ADAM10 or ADAM15, or both, could include, but are not limited to, tagging the substrate with a fluorescent group on one side of the cleavage site and with a fluorescence-quenching group on the opposite side of the cleavage site. Upon cleavage, these fluorogenic peptide substrates provide a detectable signal. Generation of a cleaved product could be assayed using neo-epitope antibodies that recognized the newly generated N- or C-termini. In this latter case, assay formats could include fluorescence polarization (Levine et al., 1997, Anal. Biochem. 247:83-88) or HTRF (Preaudator et al., 2002, J. Biomol. Screen. 7:267-274). Alternatively, the substrate can be tagged with a calorimetric leaving group that more strongly absorbs upon cleavage.

In an aspect of the invention, a compound identified by a method of the present invention, which compound is capable of inhibiting the ADAM-mediated cleavage of Her-2 for from p95 and ECD105, is recited in FIGS. 6 through 10. In another aspect of the present invention, a compound identified by a method of the present invention, which compound is capable of inhibiting the ADAM-mediated cleavage of Her-2 for from p95 and ECD105, includes (6S,7S)-N-hydroxy-5-methyl-6-[(4-phenylpiperidin-1-yl)carbonyl]-5-azaspiro[2.5]octane-7-carboxamide, (6S,7S)-N-hydroxy-5-methyl-6-[(4-phenyl-3,6-dihydropyridin-1(2H)-yl)carbonyl]-5-azaspiro[2.5]octane-7-carboxamide, (6S,7S)-N-Hydroxy-6-{-[(3-phenylpyrrolidin-1-yl]carbonyl}-5-azaspiro[2.5]octane-7-carboxamide, (6S,7S)-N-hydroxy-6-((4-(methylsulfonyl)phenyl)-3,6-dihydropyridin-1(2H)-yl)carbonyl)-5-azaspiro(2,5)octane-carboxamide, (2S,3S)-N-hydroxyl-1-methyl-2-((10aS)-3,4,10,10a-tetrahydropyrazino(1,2-a)indol-2(1H)-yl-carbonyl)piperidine-3-carboxamide, (6S,7S)-N-hydroxy-6-((10aS)-3,4,10,10a-tetrahydropyrazino(1,2-a)-indol-2(1H)-yl-carbonyl)-5-azaspiro(2,5)octane-7-carboxamide, (6S,7S)-N-hydroxy-6-((4-(3-(methylsulfonyl)phenyl)-3,6-dihydropyridin-1(2H)-yl)carbonyl)-5-azaspiro(2,5)octane-7-carboxamide, methyl(6S,7S)-7-[(hydroxyamino)carbonyl]-6-[(4-phenyl-3,6-dihydropyridin-1(2H)-yl)carbonyl]-5-azaspiro[2.5]octane-5-carboxylate, benzyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate, (6S,7S)-N-Hydroxy-5-(methylsulfonyl)-6-[(4-phenyl-3,6-dihydropyridin-1(2H)-yl)carbonyl]-5-azaspiro[2.5]octane-7-carboxamide, and (6S,7S)-N-hydroxy-6-{[4-(3-methoxyphenyl)piperidin-1-yl]carbonyl}-5-methyl-5-azaspiro[2.5]octane-7-carboxamide, each of which can be prepared according to the methods described in U.S. Ser. No. 60/534,501 the disclosure of which is incorporated herein by reference in its entirety.

The present invention therefore also includes a method of identifying a compound capable of enhancing the interaction of ADAM with Her-2. The method comprises contacting a first reaction mixture containing Her-2 and ADAM10, 15, or both, with a test compound, then assaying the first reaction mixture for the appearance of p95. A higher level of p95 in the first reaction mixture, when compared with a second reaction mixture containing Her-2 and ADAM without the test compound, is indicative of a compound capable of enhancing the interaction of ADAM with Her-2. Such a compound is defined herein as enhancing the interaction of ADAM with Her-2, as the higher level of p95 is indicative of an increased cleavage of Her-2 by ADAM. The invention includes any compound identified by this method.

Synergism of MPIs with Other Pharmaceutical Agents
Method of Synergistically Affecting a Tumor Cell Advantageously, the present invention provides a method for the synergistic treatment of cancer in that the data disclosed herein demonstrate, for the first time, a novel synergistic method for inhibiting the growth and/or for inducing the death of a tumor cell that over-expresses Her-2, such as that found in many cancers, including breast, ovarian, prostate, non-small cell lung, colon, glioma, pancreatic cancers and the like. The methods disclosed herein comprise administering a synergistically effective Her-2 inhibiting amount of at least one MPI that inhibits cleavage of Her-2, and at least one of the following synergistic agents: (1) an antibody that antagonizes Her-2-mediated cell growth, and, optionally, (2) a cytotoxic agent, and/or (3) an inhibitor of a member of the EGFR tyrosine kinase family. By the term "synergistic agent" is meant any compound or substance including, for example proteins, nucleic acids, and small molecules, that show synergism with an MPI. In some embodiments, the methods involve administering a synergistically effective amount of at least one MPI that inhibits cleavage of Her-2 and one or more of a synergistic agent selected from an antibody, cytotoxin, and EGFR tyrosine kinase inhibitor. In further embodiments, the methods involve administering a synergistically effective amount of at least one MPI that inhibits cleavage of Her-2 and at least one antibody. In further embodiments, the methods involve administering a synergistically effective amount of at least one MPI that inhibits cleavage of Her-2, at least one antibody, and at least one antiproliferative agent. In further embodiments, the methods involve administering a synergistically effective amount of at least one MPI that inhibits cleavage of Her-2, at least one antibody, and at least one small molecule inhibitor of EGFR-1. In further embodiments, the methods involve administering a synergistically effective amount of at least one MPI that inhibits cleavage of Her-2 and at least one antiproliferative agent. In further embodiments, the methods involve administering a synergistically effective amount of at least one MPI that inhibits cleavage of Her-2 and at least one cytotoxin. In further embodiments, the methods involve administering a synergistically effective amount of at least one MPI that inhibits cleavage of Her-2, at least one cytotoxin, and at least one antiproliferative agent.

Unexpectedly, it has been found that the use of: (1) at least one MPI that inhibits cleavage of Her-2, where such cleavage mediated release of ECD thereby producing a p95 "stub" that remains associated with the cell, and (2) an antibody that antagonizes Her-2 mediated cell growth, such as Herceptin™, provides a synergistic effect causing growth inhibition of the cell such that less antibody can be administered to mediate the same growth inhibiting effect as a higher amount of the same antibody. Further, the addition of at least one inhibitor of a member of the EGFR tyrosine kinase family, further enhances the cytostatic effect of Herceptin™, and/or the inhibitor such that, among other things, inhibition of cell growth and proliferation is induced using much lower, i.e., one to two logs, amounts of the antibody than when the antibody is used in the absence of the MPI. Similarly, when the MPI is administered to a cell in the presence of the antagonistic antibody and in the further presence of a cytotoxic agent (e.g., Taxol™), cell death is induced using a much lower amount of the antibody and/or the cytotoxic agent than when the antibody or the cytotoxic agent is used in the absence of the MPI. For instance, the data surprisingly demonstrate that about 10-100-fold less antagonistic antibody was required in the presence of the MPI than when the antibody was used without the MPI to mediate the same effect. Similarly, the data demonstrate that less cytototic agent (e.g., Taxol) was required when it was administered with the antibody and the MPI than when it was administered to a cell in the absence of the combination of an antibody and an MPI.

Further, the invention relates to the novel discovery that the protease that cleaves Her-2 to produce the p95 stub is and ADAM polypeptide such as, for example, ADAM10 or ADAM15, such that the invention relates to using an MPI that inhibits ADAM (e.g., ADAM10, ADAM15, or both) in the synergistic methods set forth herein. While the invention is not limited to any particular MPI, some embodiments of the invention involve MPIs that inhibit ADAM10, ADAM15, or both.

With or without the cytotoxic compound or an inhibitor of a EGFR tyrosine kinase family member, co-administration of a cleavage-inhibiting MPI and a Her-2 antagonistic antibody provides a surprising synergistic effect such that a much lower amount of the antibody mediates a cytostatic, growth-inhibiting effect in a Her-2 overexpressing cell than when the antibody is administered in the absence of the MPI. Therefore, the disclosure provided herein provides a significant improvement in therapeutics based on administration of a Her-2 antagonistic antibody. This is because it is well-known in the art that methods relating to administration of, for example, Herceptin™ are greatly hindered by the small amount of antibody that reaches the tumor cell, thereby greatly reducing the therapeutic benefit derived from such antibody-based therapy. Thus, the methods disclosed herein overcome a long-standing obstacle in the art of antibody-based tumor therapy.

Thus, the skilled artisan would appreciate, based on the disclosure provided herein, that antibody-based cell therapy, wherein a cytostatic (i.e., growth inhibiting), cytotoxic (i.e., cell death), or both, effect is desired, is greatly improved by administering a Her-2 cleavage-inhibiting MPI in concert with a Her-2 antagonistic antibody. Additionally, where a cytotoxic (i.e., cell killing) effect is desired, the cytotoxic effect of an agent is synergistically enhanced by administering the cytotoxic agent (encompassing a wide plethora of compounds including, but not limited to, Taxol) in concert with a Her-2 cleavage-inhibiting MPI and a Her-2 antagonistic antibody. Thus, the surprising synergistic effect provided by co-administering a Her-2 antagonistic antibody and a Her-2 cleavage-inhibiting MPI provides vastly improved cytotoxic cell therapy where cell death is desired using a cytotoxic compound in concert with the antibody and the MPI.

Further, the data disclosed herein demonstrate that the synergistic anti-tumor effect is also observed when an MPI and an antibody are administered in conjunction with an inhibitor of a member of the EGFR tyrosine kinase family (e.g., Iressa). Thus, the synergistic anti-tumor effect is surprisingly mediated even where the inhibitor is not known to directly affect Her-2 and/or its processing.

Thus, a small molecule inhibitor specific for an EGFR tyrosine kinase family member, exemplified by EGFR-1, also mediates a synergistic cytostatic cell growth inhibiting effect when administered with Herceptin™ and an MPI, and one skilled in the art would understand, based on this surprising data, that the compounds that can be administered with the MPI and antibody include, but are not limited to, molecules and compounds that in any form or shape, act to antagonize tumor formation, progression and maintenance, or any related biological processes. Examples of these agents include, but are not limited to, antiproliferative agents such as other epidermal growth factor inhibitors, Her-2 inhibitors, Met kinase inhibitors, MEK-1 kinase inhibitors, MAPK kinase inhibitors, PI3 inhibitors, Src kinase inhibitors, PDGF inhibitors, inhibitors of integrin signaling, and inhibitors of insulin-like growth factor receptors and any poly- and monoclonal antibodies antagonizing the above kinases/receptors/signaling pathways; antiangiogenesis agents such as other metalloproteinase inhibitors, and anti-VEGF antibodies and small molecules such as ZD6474 and SU6668.

Antiproliferative agents also include agents that are used as hormonal treatment. Examples of such agents include, but are not limited to, Casodex™ (also referred to as bicalutamide, AstraZeneca), which renders androgen-dependent carcinomas non-proliferative and antiestrogen Tamoxifen, which inhibits the proliferation or growth of estrogen dependent breast cancer. Examples also include, but are not limited to, natural substances, vaccines, antisense oligonucleotides, ribozymes, RNA interferences and gene therapies that are known in the art and as will be developed in the future to treat Her-2 over-expressing and other malignancies.

The skilled artisan would appreciate that that present invention encompasses administration of more than one Her-2 cleavage inhibiting MPI and/or antagonistic antibody, and is not limited to any particular MPI or antibody. Moreover, the invention encompasses administration of any cytotoxic agent, any inhibitor set forth elsewhere herein (e.g., an inhibitor of an EGFR tyrosine kinase family member, among others), and the like, in any combination or permutation thereof.

One skilled in the art could readily establish, based upon the teachings provided herein, whether an antibody, an MPI, or any other inhibitor or substance of interest, or any combination thereof, when administered to a Her-2 overexpressing cell, mediate the desired synergistic effect disclosed herein. This is because, as exemplified herein, methods for assessing whether (1) a cell overexpresses Her-2, (2) a MPI inhibits cleavage of Her-2, (3) an antibody antagonizes cell growth in the Her-2 overexpressing cell, and (4) the combination of the antagonistic antibody with the MPI reduces the amount of antibody that must be administered to achieve the same level of Her-2 cleavage inhibition, which, in turn, mediates the desired effect (e.g., inhibition of cell growth and division and/or promoting cell death) are disclosed herein and/or are well-known in the art. Accordingly, following the teachings provided herein, the routineer can mediate desired cell growth inhibition and/or cytotoxicity using a wide plethora of combinations comprising at least one antibody that specifically binds with Her-2 and at least one MPI, with or without an additional compound, and any permutation thereof.

The present invention provides methods for the synergistic treatment of a variety of diseases or disorders mediated by a Her-2 overexpressing cell, including, but not limited to, cancer such as breast cancer, ovarian cancer, prostate cancer, glioma, pancreatic cancer, colon cancer, non-small cell lung cancer and the like. This is because, advantageously, the synergistic method of this invention reduces the growth and/or viability of a tumor cell overexpressing Her-2, thereby reducing tumor burden, producing tumor regression, or both.

In general, numerous synergistic agents can be administered in a combination with an MPI including, for example, anti-neoplastic agents. As used herein, the phrase "anti-neoplastic agent" is synonymous with "chemotherapeutic agent" and refers to compounds that prevent cancer cells from multiplying (i.e. anti-proliferative agents). In general, the antineoplastic agent(s) of this invention fall into two classes, cytotoxic and cytostatic agents. Without wishing to be bound by any particular theory, cytotoxic agents prevent cancer cells from multiplying by: (1) interfering with the ability of the cell to replicate DNA and (2) inducing cell death and/or apoptosis in the cancer cells. Cytostatic or quiescent agents act via modulating, interfering or inhibiting the processes of cellular signal transduction which regulate cell proliferation.

Classes of compounds that may be used as cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan™), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol™), Mithramycin, Deoxyco-formycin, Mitomycin-C, L-Asparaginase, Interferons (especially IFN-a), Etoposide, and Teniposide.

Other cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol™, NSC 125973), Taxol™ derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, 1996, Science 274:2009) estramustine, nocodazole, MAP4, and the like. Examples of such agents are also described in the scientific and patent literature, see, e.g., Bulinski, 1997, J. Cell Sci. 110:3055-3064; Panda, 1997, Proc. Natl. Acad. Sci. USA 94:10560-10564; Muhlradt, 1997, Cancer Res. 57:3344-3346; Nicolaou, 1997, Nature 387:268-272; Vasquez, 1997, Mol. Biol. Cell. 8:973-985; Panda, 1996, J. Biol. Chem. 271: 29807-29812.

The term "paclitaxel" as used herein refers to the drug commercially available as Taxol™ (NSC number: 125973). Taxol™ inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz, 1992, Trends Pharmacol. Sci, 13: 134-146, Rowinsky, 1990, J. Natl. Canc. Inst. 82:1247-1259).

Further example cytotoxic agents are compounds with paclitaxel-like activity. These include, but are not limited to, paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

Thus, cytotoxic agents which are suitable for use in the methods and compositions of this invention include, but are not limited to, microtubule-stabilizing agents such as paclitaxel (also known as Taxol™) docetaxel (also known as Taxotere™), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Pat. No. 6,537,988), C-4 methyl carbonate paclitaxel (disclosed in WO 94/14787), epothilone A, epothilone B, epothilone C, epothilone D, desoxyepothilone A, desoxyepothilone B, [1s-[1R*,3R*(E),7R*,10S*,11R*,12R*,16S]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,1'-dihydroxy-8,8,10,12,16-pentamethyl-4-17-dioxabicyclo [14.1.0]-heptadecane-5,9-dione (disclosed in U.S. Pat. Nos. 6,262,094 and 6,537,988), and derivatives thereof; and microtubule-disruptor agents.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agent(s), such as Herceptin™, are agents which cause cells to become "non-proliferative" or "quiescent." The anti-proliferative cytostatic agent of the invention is a Her-2 antagonistic antibody, as exemplified by Herceptin™. One skilled in the art would understand, based upon the disclosure provided herein, that a Her-2 antagonistic antibody encompasses Herceptin™, but is not limited to such antibody. Rather, the present invention includes other Her-2 antagonistic antibodies, such as are known presently, including, but not limited to, anti-Her-2 antibodies (e.g., 2C4, 4D5, Trastuzumab-DMI; all available from Genentech, Inc.), and anti-EGFR-1 antibodies (e.g., IMC-C225 (ImClone Systems, Inc.), and ABX-EGF (Abgenix, Inc.)), or such antagonistic antibodies as may be developed in the future.

As used herein, "cytostatic agent" is synonymous with "quiescence agent" and refers to any means of slowing the rate of cell division or tumor growth so that the cells become non-proliferative or so that their behavior approximates that of non-proliferative cells. Exemplary anti-proliferative cytostatic or "quiescent" agents of the invention, include without limitation, Herceptin™ (also referred to as trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

The skilled artisan would understand, based upon the disclosure provided herein, that the amount of the Her-2 cleavage inhibiting MPI is typically such that a detectable amount of Her-2 cleavage is inhibited when compared with the level of Her-2 cleavage in the cell prior to administration of the MPI or when compared with the level of Her-2 cleavage in an otherwise identical cell not to which the MPI is not administered. Preferably, the detectable level of Her-2 cleavage is decreased by about at least 30%, more preferably, by about at least 40%, even more preferably, by about at least 50%, yet more preferably, by at least about 60%, preferably, by at least about 70%, even more preferably, by at least about 80%, most preferably, by at least about 90%. Even more preferably, the detectable level of Her-2 cleavage is inhibited by at least about 95%, yet more preferably, by at least about 99%, and most preferably, it is inhibited by about 100%. Accordingly, although a threshold level of sheddase inhibition is required, the inhibition need not be, although it can be, complete, such that, preferably, at least 90% inhibition of cleavage of Her-2 is desired to provide the synergistic effect when a cytostatic and/or cytotoxic agent is added.

Thus, one skilled in the art would understand, based upon the disclosure provided herein, that the amount of MPI mediates a detectable decrease in the level of Her-2 cleavage in order to mediate a synergistic effect when a Her-2 antagonistic antibody is administered with the MPI. The amount of the antagonistic antibody required will then be much less than the level of the antibody required to mediate the same cytostatic effect in the absence of the MPI. The synergistic amount of the MPI and the antagonist antibody can be readily determined for each Her-2 overexpressing tumor cell of interest, and will vary by, among other things, the level of Her-2 expressed in the cell, and other parameters as are routinely assessed by those skilled in the art.

In sum, the synergistic effect achieved using the novel methods and compositions of the present invention is greater than the sum of the effects that result from methods and compositions comprising using the cytotoxic (e.g., Taxol™) or cytostatic agent (i.e., a Her-2 antagonistic antibody, such as, but not limited to, Herceptin™), or an inhibitor of a EGFR tyrosine kinase family (e.g., the small molecule inhibitor of EGFR-1, Iressa™), either singly or in the absence of a Her-2 cleavage inhibiting MPI. Advantageously, such synergy between compounds allows for the use of smaller doses of at least one compound, provides greater efficacy at the same doses, and/or prevents or delays the build-up of multi-drug resistance.

Further advantages over previously disclosed methods include the ability of the instant combination of an MPI and at least one agent selected from the group consisting of a cytostatic agent (i.e., a Her-2 antagonistic antibody), an inhibitor of a EGFR tyrosine kinase family (e.g., Iressa™), and/or a cytotoxic agent (e.g., Taxol™, Cisplatin™, and the like), to be individually varied depending on the nature of the Her-2 over-expressing cell to be treated. The data disclosed elsewhere herein indicate that the therapeutic effect of the instant compositions can be achieved with suboptimal amount of the cytotoxic or cytostatic agent(s) and MPI than would be required if such agents and compounds were administered individually. The novel approach disclosed herein of combining, among other things. Herceptin and MPI, avoids any non-mechanism-based adverse toxicity effects which might result from administration of an amount of cytotoxic or cytostatic agent(s) and MPI compounds alone sufficient to achieve the same therapeutic effect.

The instant compositions achieve a synergistic therapeutic effect and exhibit unexpected therapeutic advantage over the effect of any of the component compounds or methods when administered individually. In addition, such combinations can effectively target proliferative cells by providing a synergistic effect when a Her-2 cleavage-inhibiting MPI is combined with a cytostatic Her-2 inhibitor (i.e. an antagonistic antibody such as, e.g., Herceptin™) and/or with a cytotoxic agent such as, but not limited to, Taxol™, and/or with an inhibitor of a member of the EGFR tyrosine kinase family.

The anti-proliferative cytostatic agent(s) (i.e., an antagonistic antibody such as, e.g., Herceptin™, an inhibitor of a member of the EGFR tyrosine kinase family, and the like) can be administered, preferably, following administration of a Her-2 cleavage-inhibiting MPI; however, the antagonist antibody can be administered to a cell simultaneously and/or contemporaneously with the MPI. Also, an additional agent (e.g, a cytotoxic agent, an inhibitor of an EGFR tyrosine kinase family member, and the like), can be added prior to, after, or simultaneously with the antagonistic antibody, to produce a synergistic inhibition of cell growth (for cytostatic agents) or increasing cell death (for cytotoxic agents).

In a preferred embodiment of the present invention, the Her-2 cleavage inhibiting antagonistic antibody and the Her-2 cleavage inhibiting MPI are administered contemporaneously. However, the skilled artisan would appreciate, based upon the teachings provided herein, that the MPI can be administered prior to administration of the antibody or other agent.

As used herein, the term "simultaneous" or "simultaneously" means that the MPI and antibody are administered within at least about 24 hours, preferably at least about 12 hours, more preferably, at least about 6 hours, even more most preferably, at least about 3 hours, yet more preferably, about 1 hour, and even more preferably, less than about 1 hour.

Methods of Identifying a Useful Synergistic Compound

The skilled artisan would appreciate, once armed with the teachings provided herein, that additional synergistic agents such as, for example, Her-2 antagonistic antibodies, useful to practice the methods of the invention can be readily identified and isolated using art-recognized methods for identifying agents having the desired properties of detectably inhibiting Her-2 mediated cell growth and further exhibiting a synergistic effect with a Her-2 cleavage-inhibiting MPI such that a lesser amount of the synergistic agent can inhibit the same level of cell growth in the presence of the MPI compared with the amount of synergistic agent required to inhibit the same level of cell growth in the absence of the MPI.

Similarly, the present invention encompasses methods of identifying novel synergistic MPIs that inhibit cleavage of Her-2, and MPIs identified using such methods. The skilled artisan would appreciate that the methods comprise contacting a cell overexpressing Her-2 with a test compound, in the presence or absence of a Her-2 antagonistic antibody, such as, e.g., Herceptin. The level of inhibition of Her-2 cleavage is assessed in a cell contacted with both the test compound and the antibody and also in an otherwise identical cell contacted only with the test compound, and in yet another otherwise identical cell contacted with only the antibody. The level of Her-2 mediated cell growth in the three cells is compared where a level of cell growth that is lower in the cell contacted with both the antibody and the test compound compared with the level in either the cell contacted with the antibody alone or in the cell contacted with the test compound alone, or where the level of cell growth of the cell contacted with the antibody and the test compound is less than the sum of the level of growth of the cell contacted with the antibody and the level of growth of the cell contacted with the test compounded combined, is an indication that the test compound synergistically inhibits Her-2 mediated cell growth in a cell when administered with the antibody. The invention encompasses compounds identified using this method, such compounds include, but are not limited to, those exemplified herein, e.g., Compound 5 and AG3340 (Prinomastat).

The present invention encompasses methods of identifying a novel synergistic agent that inhibits proliferation of a Her-2 over-expressing cell and any agent identified using such methods. That is, the methods comprise contacting a cell overexpressing Her-2 with a test compound, in the presence of a Her-2 antagonistic antibody, such as, e.g., Herceptin, and an MPI (e.g., Compound 5 and AG3340 (Prinomastat)). The level of inhibition of proliferation is assessed in a cell contacted with both the test compound and the antibody and MPI, in an otherwise identical cell contacted only with the test compound, and in yet another otherwise identical cell contacted with only the antibody and MPI. The level of cell growth in the three cells is compared where a lower level of cell growth in the cell contacted with the test compound, the antibody and the MPI, compared with the level in either the cell contacted with the antibody and MPI, or in the cell contacted with the test compound alone, or where the level of cell growth in the cell contacted with the test compound, the antibody and the MPI is less than the sum of the level of cell growth in the cell contacted with the antibody and the MPI combined with the level of cell growth in the cell contacted with the test compound, is an indication that the test compound synergistically inhibits Her-2 mediated cell growth in a cell when administered with the antibody and the MPI. The invention encompasses compounds identified using this method, such compounds include, but are not limited to, those exemplified herein, e.g., Iressa™.

Kits

The invention further encompasses kits for the practice of the methods disclosed herein. That is, the invention includes various kits which comprise a compound, such as a nucleic acid encoding a nucleic acid complementary to a nucleic acid encoding a Her-2-cleaving ADAM, but in an antisense orientation with respect to transcription, a siRNA specific for a Her-2 cleaving ADAM (e.g., ADAM10, ADAM15, or variant thereof), and/or compositions of the invention, an applicator, and instructional materials which describe use of the compound to perform the methods of the invention. The kits relate to the novel discovery that ADAM10, and ADAM15, cleave Her-2 to produce a p95 stub that remains associated with a cell and mediates and/or is associated with various conditions, diseases or disorders such that inhibiting the cleavage provides a benefit.

The kits also relate to the surprising discovery that there are splice variants of ADAM15 detected in a cell expressing Her-2 and from which Her-2 is shed. Indeed, the data disclosed herein demonstrate, for the first time, two novel variants of ADAM15, i.e., variant 1 and the even longer variant 2, where variant 1 appears preferentially detectable in cells that shed Her-2, producing a p95 stub that remains associated with the cell.

The kits also relate to the novel discovery that administration of certain MPIs to a cell, when combined with various compounds disclosed herein, provides a novel synergistic effect relating to inhibition of Her-2 cleavage to produce the p95 stub.

Although exemplary kits are described below, the contents of other useful kits will be apparent to the skilled artisan in light of the present disclosure. Each of these kits is included within the invention.

In one aspect, the invention includes a kit for alleviating a disease mediated by overexpression of a Her-2 receptor. The kit is used pursuant to the methods disclosed in the invention. Briefly, the kit may be used to contact a cell with a nucleic acid complementary to a nucleic acid encoding a Her-2 receptor where the nucleic acid is in an antisense orientation with respect to transcription to reduce expression of the receptor, or with an antibody that specifically binds with such receptor or a nucleic acid encoding the antibody, wherein inhibition or reduction in cleavage of Her-2 mediates a beneficial effect, or with a compound that inhibits cleavage of Her-2 by the ADAM, or combinations thereof. Moreover, the kit comprises an applicator and an instructional material for the use of the kit. These instructions simply embody the examples provided herein.

The kit can further include a synergistic amount of an antibody that affects Her-2 cleavage, such as, but not limited to, Herceptin. Additionally, the kit can further comprise a synergistic amount of a cytotoxic agent, such as, among others, Taxol.

In another aspect, the invention includes a kit for alleviating a disease mediated by overexpression of a Her-2 receptor. The kit is used pursuant to the methods disclosed in the invention. Briefly, the kit may be used to contact a cell with a compound capable of inhibiting the ADAM-mediated cleavage of Her-2. As discussed elsewhere herein, such a compound may interact with an ADAM, with Her-2, or with both, consequently inhibiting the cleavage of Her-2 by an ADAM to form p95 and ECD105. The inhibition of Her-2 cleavage thereby mediates a beneficial effect.

The invention includes a kit comprising a synergistic amount of an antibody antagonist of Her-2, an ADAM inhibitor, an applicator, a standard, and an instructional material which describes administering the composition to a cell or an animal. This should be construed to include other embodiments of kits that are known to those skilled in the art, such as a kit comprising a standard and a (preferably sterile) solvent suitable for dissolving or suspending the composition of the invention prior to administering the compound to a cell or an animal. Preferably the animal is a mammal. More preferably, the mammal is a human.

The invention encompasses a kit for inhibiting proliferation of a Her-2 over-expressing cell. The kit comprises a synergistic amount of an antibody that is a Her-2 antagonist, and an ADAM inhibitor. The kit can further comprise a synergistic amount of a cytotoxic agent, including, but not limited to, Taxol, Cisplatin, and the like.

The skilled artisan would readily appreciate, based upon the disclosure provided herein, that the present invention includes a wide variety of kits for practicing the various methods of the invention.

In an aspect of the invention, a kit of the present invention includes a pharmaceutically-acceptable carrier. The composition is provided in an appropriate amount as set forth elsewhere herein. Further, the route of administration and the frequency of administration are as previously set forth elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Identification of ADAM10 and ADAM15 as Agents that Specifically Cleave Her-2

The data disclosed herein demonstrate, for the first time, that cleavage of Her-2 to produce an ectodomain that is released from a cell and a p95 stub that remains associated with the cell is specifically mediated by ADAM10 and by ADAM15. These data facilitate the development of potential therapeutics relating to inhibition of the cleavage of Her-2. The materials and methods are described below.

Cellular Reagents

Human breast cancer cell lines BT474 (HTB-20), SKBR3 (HTB-30), SKOV3 (HTB-77), MDA-MB-231 (HTB-26) and T47D (HTB-133) were obtained from the American Type Tissue Culture Collection (ATCC, Manassas, Va.). Cells were routinely maintained in media recommended by the ATCC with slight modifications. Cells were kept at 37° C. in a humidified incubator supplied with 5% $CO_2$. BT-474 cells were grown in RPMI 1640 (Invitrogen) supplemented with 10% fetal bovine serum (FBS), 0.01 mg/ml bovine insulin and 0.1 mM non-essential amino acids. SKBR-3 cells were grown in McCoy's 5a (Invitrogen) supplemented with 10% FBS. T47D cells were grown in RPMI 1640 (Invitrogen) supplemented with 10% FBS and 10 ug/ml bovine insulin. MDA-MB-231 (HTB-26) cells were grown in DMEM (Invitrogen) supplemented with 10% FBS. SKOV3 cells were grown in McCoy's 5a (Invitrogen) supplemented with 10% FBS. Both BT-474 and SKBR-3 cells overexpress Her-2 on the surface and have high level of Her-2 cleavage.

The results of the experiments described herein are as follows.

Identification of Proteases Responsible for Cleaving Her-2

The data disclosed herein demonstrate that ADAM10 and ADAM15 are responsible for cleavage of Her-2 to produce p95, a constitutively-active membrane-associated receptor, and ECD105, a soluble extracellular domain derived from the Her-2 receptor. The data disclosed herein demonstrate that various ADAMs are expressed in cells that shed Her-2. Moreover, the data demonstrate that ADAM10 siRNAs inhibited Her-2 shedding in cells that shed Her-2. More specifically, Her-2 shedding in BT474 and SKBr3 cell lines that shed Her-2 was inhibited by about 50-70% by ADAM10 siRNA compared with cells in the absence of siRNA.

Similarly, the data disclosed demonstrate that ADAM15 also cleaves Her-2 in that ADAM15 siRNA reduced Her-2 shedding by about 25-30% in SKBr3 cells and by about 10% in BT474 cells compared with otherwise identical cells in the absence of ADAM15 siRNA.

Additionally, the data disclosed herein demonstrate that there is a significant correlation between Her-2 "sheddase" inhibition and inhibition of certain ADAMs as assessed by determining the IC50 for numerous compounds for biochemical enzyme based inhibition and inhibition of Her-2 shedding.

There are twenty-three (23) annotated ADAM family members in humans (FIG. 1). ADAM10 and ADAM3 are annotated as pseudogenes and were excluded from further analysis since they do not encode functional ADAM family members. Twelve of the remaining human ADAM family members contain HEXGHXXGXXHD (SEQ ID NO: 45) sequences for metalloprotease active sites (ADAMs 8, 9, 10, 12, 15, 17, 19, 20, 21, 28, 30, and 33). With the exception of ADAM20 and ADAM21, the human catalytically active family members have complex intron/exon gene structures. The lack of introns in protein coding region ADAM20 and ADAM21 raises the possibility that they may also be pseudogenes (Poindexter et al., 1999, Gene 237:61-70). Additionally, an analysis of the public domain genomic and cDNA sequences for ADAM20 reveals that the open reading frame extends N-terminal of the consensus start methionine and contains 50 N-terminal residues that lack a signal peptide.

Based on this latter analysis, ADAM20 may encode a non-functional ADAM.

qPCR Analysis Of Breast Cancer Cell Lines

The expression pattern of catalytically active ADAMs was assessed in HER2 shedding cell lines in order to narrow the list of HER2 sheddase candidates. Total RNA was isolated from cell lines using the RNeasy total RNA isolation system and DNased according to the manufacturer's (Qiagen, Valencia, Calif.) instructions. RNA purity and concentration was determined spectrophotometrically (260 nm/280 nm); RNA integrity was assessed by Agilent Bioanalyzer analysis: rRNA ratios were >2.0 for all samples assayed in this study, indicating intact, high quality RNA. Fluorescence-based real-time PCR was performed essentially as described (Gibson et al., 1996, Genome Research 6:995-1001). Primers and probes were designed to detect and discriminate mRNAs from 12 different ADAM family genes: ADAM8, ADAM9, ADAM10, ADAM12, ADAM15, ADAM17, ADAM19, ADAM20, ADAM21, ADAM28, ADAM30, and ADAM33. Oligonucleotides were synthesized by Applied Biosystems (Foster City, Calif.). All primer/probe sequences are shown in FIG. 2.

Probe sequences were modified at the 5' end with the reporter dye 6-FAM, and at the 3' end with the quencher dye TAMRA. Probes detecting human 18s rRNA were modified at the 5' end with VIC and at the 3' end with TAMRA (Applied Biosystems, Foster City, Calif.). Template cDNA was generated using the Advantage RT-PCR kit according to the manufacturer's (Clontech, Palo Alto, Calif.) instructions using random hexamers and 1 μg of DNaseI-treated total RNA. Taqman-based real-time PCR expression profiling was performed using 25 ng of each cDNA according to the manufacturer's (Applied Biosystems, Foster City, Calif.) instructions with fluorescence being monitored in real-time with an ABI Prism 7900 (Applied Biosystems, Foster City, Calif.). Relative expression levels were determined essentially as described (Gibson, 1996) using standard curves for each transcript. Relative abundance values for each cell type were corrected for background amplification by subtracting mRNA abundance levels obtained from control reactions performed in the absence of reverse transcriptase. Normalization between cell types was performed using assays specific to 18s rRNA, an invariant control RNA species present in all samples. All expression measurements were performed in triplicate.

qPCR analysis demonstrated that various cell lines that shed Her-2 at various levels, express certain ADAMs. That is, Her-2 shedding was assessed using an ELISA assay to detect she ECD in conditioned medium obtained from various cell cultures. The relative level of Her-2 shedding was denoted by one through four "+" signs, with "+" being low levels of shedding and "++++" being high levels of shedding (FIG. 3). Expression of ADAMs 8, 9, 10, 12, 15, 17, 19, 20, 21, 28, 30, and 33 in each cell line was determined. Two of the highest Her-2 shedding lines, having four plus signs ("++++") each, BT474 and SKBR3, did not express detectable levels of ADAM28 or ADAM30, thereby eliminating these ADAMs as potential sheddases. Further, prior studies suggested that ADAM17 (TACE) was not a HER2 sheddase candidate (Rio et al., 2002, J. Biol. Chem. 275:10379-103870). The data demonstrated that eight of the catalytically active ADAMs were expressed in all shedding cell lines examined. The data did not demonstrate a correlation between level of Her-2 shedding and expression of any particular ADAM or ADAMs. Without wishing to be bound by any particular theory, the lack of correlation between RNA and shedding level suggests that the HER-2 sheddase is not rate limiting at the expression levels seen in these cell lines.

siRNA Mediated Specific Knock-Down of ADAMs

Based on the transcriptional profiling data obtained using qPCR, siRNAs were designed and produced that specifically reduced expression of ADAMS, 9, 10, 15, 21, and 33. siRNAs to ADAM17 were also developed for use a negative controls in shedding experiments. The siRNAs are commercially available.

Transfection of siRNAs into cells was performed using Oligofectamine (Elbashir et al., 2001, Nature 411:494-498) and knockdown was assessed by western analysis. Briefly, cells were seeded into multi-well plates so that the density was no greater than 50% confluence at the time of transfection. Cells were harvested 48 to 96 hours following transfection by washing once with PBS and harvesting in PBS by scraping. Cell pellets were lysed in buffer containing 25 mM Hepes, pH 7.5; 150 mM NaCl, 1 mM EDTA, 5% glycerol, 1% Triton X-100 and a cocktail of proteinase inhibitors (Roche). After incubation on ice for 30 minutes, the cellular debris was removed by centrifugation at 14,000 rpm at 4 C. Total protein concentration was measured using the bicinchoninic acid method (Pierce), and equivalent amounts of cell extracts were resolved by SDS-PAGE and transferred to nitrocellulose membranes.

ADAM proteins were detected by immunoblotting using commercially available antibodies specific to each protein (anti-ADAMS, Ab-1 Oncogene Research; anti-ADAM10, Ab-1 Oncogene Research; anti-ADAMS, RP1 Triple Point Biologics; anti-ADAM15, RP1 Triple Point Biologics; anti-ADAM17, Ab-1 Oncogene Research; anti-ADAM21, Chemicon International; and anti-ADAM33, polyclonal rabbit antiserum produced internally against an immunizing peptide corresponding to amino acids 777 to 790). Filters were washed with PBS-Tween 20 and then incubated with the appropriate secondary antibody conjugated to horseradish peroxidase (Pierce), washed again, and the immunoconjugates were developed using enhance chemiluminescent reagents (Pierce) and visualized by exposure to X-ray film. In many experiments, the same filter was stripped with Restore reagent (Pierce) and reprobed with a different anti-ADAM antibody or with anti-glyceraldehyde phosphate dehydrogenase (RDI) for normalization of protein loading.

Initially pools of 4 siRNA oligonucleotides were used against each target ("Smart Pool Technology", Dharmacon). For siRNA pools that effectively reduced Her2 shedding (ADAM10 and ADAM15), the individual siRNA oligos comprising each Smart Pool were obtained together with their corresponding sequence information. The individual siRNAs were then transfected separately and their ability to reduce Her-2 shedding was evaluated as described in order to identify the efficacious siRNA oligonucleotides. The sequence of the siRNAs that effectively reduced ADAM10 protein called ADAM10-3is 5'-GGACAAACTTAACAACAAT (SEQ ID NO:7) that corresponds to nucleotides 1272 to 1300 (relative to ATG) of the full length sequence of ADAM10 (SEQ ID NO:5). The sequence of the ADAM15 siRNA that was most effective ADAM15-2 is 5'-GCCCAACCCTGGTGTGGTA (SEQ ID NO:8) corresponding to nucleotides 281-299 (relative to ATG) of the full length sequence of ADAM15.

The efficacy of each siRNA to specifically inhibit expression of the ADAM for which it was designed was assessed. The data disclosed herein demonstrate that each siRNA was specific for its respective ADAM and inhibited that ADAM but did not detectably inhibit expression of other ADAMs (FIGS. 4A-4D). More specifically, ADAM10 siRNA inhibited ADAM10 but did not affect the level of ADAM9 as determined using western blot analysis (FIG. 4A). Similarly, ADAM9 siRNA did not detectably affect expression of ADAM10, but dramatically inhibited expression of ADAM9 (FIG. 4B). Moreover, ADAM15 siRNA specifically inhibited expression of ADAM15, but did not detectably inhibit expression of ADAM17 (FIGS. 4C and 4D). ADAM17 siRNA was also shown to inhibit expression of ADAM17 (FIG. 4D).

Further, the data demonstrated that ADAM8 and ADAM21 had minimal effect on protein levels. Further, ADAM33 protein was not detectable in untreated, control BT474 or SKBr3 cell extracts and was not investigated further.

Therefore, the data disclosed herein demonstrate the successful design and production of siRNAs that specifically inhibit an ADAM but not the other ADAMs when expressed in a cell that sheds Her-2. In addition, the siRNAs each reduced the level of its specific ADAM by about 75% compared with an identical cell in the absence of the siRNA.

siRNA Inhibition of Her-2 Shedding

Next, the various siRNAs were examined to see what effect, if any, of the inhibition of the various ADAMs had on Her-2 shedding. To detect the cleaved Her2 ECD, cells were seeded into 24-well dishes at approximately 50% confluence. After an overnight incubation to allow cell attachment, cells were transfected with siRNAs using Oligofectamine (Elbashir et al., 2001, Nature 411:494-498). Twenty four hours later, cells were again fed with fresh medium. After an additional 24 hour incubation, the medium was removed, cells were washed once with phosphate buffered saline, and fresh medium was added to each well. After 48 hours incubation, the conditioned medium was collected, centrifuged at 5000 rpm for 5 minutes, and the supernatant was removed for immediate analysis by ELISA or frozen at −20° C. until such analysis could be performed. Detection of Her2 ECD was performed using a commercial ELISA kit for c-erbB2/c-neu (Oncogene Research Products, Catalog no QIA10) according to manufacturer's protocol.

The data disclosed herein demonstrate that ADAM10 siRNA reduced Her-2 shedding by about 50-70% in both BT474 and SKBr3 cells (FIGS. 5A and 5B, respectively). siRNAs to ADAM8, 9, 17 and 33 did not detectably affect Her-2 shedding in either cell line (FIGS. 5A and 5B). However, ADAM15 siRNA reduced Her-2 shedding in BT474 cells by about 10%. More strikingly, the same siRNA reduced Her-2 shedding by about 25-30% in SKBr3 cell, demonstrating that the effects of the ADAM15 siRNA was cell dependent.

The data disclosed herein demonstrate that ADAM10 and ADAM15 mediate Her-2 shedding such that inhibiting the ADAM in a cell causes a detectable decrease in Her-2 shedding by the cell.

Correlation of Her-2 Sheddase Inhibition and ADAMs Inhibition

Source of enzymes for biochemical assays: Except for ADAM17 and MT1-MMP, all recombinant human MMPs and ADAMs were obtained from R&D Systems (Minneapolis, Minn.). Their catalog numbers are as following: MMP1 (901-MP), MMP2 (902-MP), MMP3 (513-MP), MMP7 (907-MP), MMP8 (908-MP), MMP9 (911-MP), MMP10 (910-MP), MMP12 (919-MP), MMP13 (511-MM), ADAM9 (939-AD), and ADAM10 (936-AD). MT1-MMP was obtained from US Biological (Swampscott, Mass.) with a catalog number of M2429. Porcine ADAM17 was purified in house from porcine spleen.

Substrates for biochemical assays: Fluorogenic Peptide substrate, (7-methoxycoumarin-4-yl)acetyl-Pro-Leu-Gly-Leu-(3-[2,4-dinitrophenyl]-L-2,3-diaminopropionyl)-Ala-Arg-NH$_2$ (SEQ ID NO: 46), was obtained from R&D Systems (Minneapolis, Minn.) with a catalog number of ES001. It was used as substrate for MMP1, MMP2, MMP7, MMP8, MMP9, MMP12, MMP13, and MT1-MMP. Fluorogenic Peptide substrate, (7-methoxycoumarin-4-yl)acetyl-Arg-Pro-Lys-Pro-Val-Glu-Nva-Trp-Arg-Lys(2,4-dinitrophenyl)-NH$_2$ (SEQ ID NO: 47), was obtained from R&D Systems with a catalog number of ES002. It was used as substrate for MMP3 and MMP10. Fluorogenic Peptide substrate, (7-methoxycourmarin-4-yl)-acetyl-Pro-Leu-Ala-Gln-Ala-Val-(3-[2,4-dinitrophenyl]-L-2,3-diaminopropionyl)-Arg-Ser-Ser-Ser-Arg-NH$_2$ (SEQ ID NO: 48), was obtained from R&D Systems with a catalog number of ES003. It was used as substrate for ADAM10 and ADAM17.

Biochemical Assays: In general, assay buffer conditions were chosen based on obtaining optimal enzymatic activities. The specific assay buffer conditions are summarized as following. For MMP1, MMP2, MMP3, MMP7, and MMP12, the assay buffer contains 50 mM Tricine, 10 mM NaCl, 10 mM CaCl$_2$, 1.0 mM ZnCl$_2$, pH 7.4.

For MMP8 and MMP13, the assay buffer contains 50 mM Tricine, 10 mM NaCl, 10 mM CaCl$_2$, 1.0 mM ZnCl$_2$, 0.001% Brij35, pH 7.4. For MMP9 and MMP10, the assay buffer contains 50 mM Tris-HCl, 150 mM NaCl, 10 mM CaCl$_2$, 0.001% Brij35, pH 7.5. For MT1-MMP, the assay buffer contains 100 mM Tris-HCl, 100 mM NaCl, 10 mM CaCl$_2$, 0.001 Brij35, pH 7.5.

For ADAM9, the assay buffer contains 25 mM Tris, 2.5 uM ZnCl$_2$, and 0.001% Brij35, 0.1 mg/mlBSA, pH 9.0. For ADAM10, the assay buffer contains 25 mM Tris, 2.5 uM ZnCl2, and 0.005% Brij35, pH 9.0. For ADAM17, the assay buffer contains 25 mM Tris, 2.5 μM ZnCl$_2$, and 0.001% Brij35, pH 9.0.

To activate MMP enzymes, 10 or 20 μg of lyophilized Pro-MMPs are dissolved in 100 μL of water. 100 mM p-aminophenylmercuric acetate (APMA) stock in DMSO is added to Pro-MMPs to give 1.0 mM final concentration. Incubate enzyme with APMA at 37° C. for a period time specified below. For MMP1, MMP7, and MMP8, the incubation time is 1 hour. For MMP10 and MMP13, the incubation time is 2 hours. For MMP3 and MMP9, the incubation time is 24 hours.

In general, 5 mM compound stock was prepared in DMSO. Two-fold serial dilution starting with a specific concentration was performed to give the compound plate. 1.0 μL of compound in DMSO was transferred from compound plate to the assay plate. Enzyme solution was prepared in assay buffer with a concentration specified below. Substrate solution was prepared in assay buffer with a concentration of 20 μM. 50 μL of enzyme solution was added to the assay plate. The assay plate was incubated for 5 minutes. 50 μL of substrate solution was then added to the assay plate. The plate was protected from light and the reaction was incubated at room temperature or 37° C. for a period of time specified below. The reaction was stopped by adding 10 μL of 500 mM EDTA solution. The plate was read on a plate reader with excitation of 320 nm and emission of 405 nm. Percentage of inhibition was calculated for each concentration and IC50 value was generated from curve fitting.

Specific conditions for each assay are as following: MMP1 enzyme concentration 1000 ng/mL, room temperature, 1 hour incubation; MMP2 enzyme concentration 200 ng/mL, room temperature, 1 hour incubation; MMP3 enzyme concentration 1000 ng/mL, room temperature 1 hour incubation; MMP7 enzyme concentration 100 ng/mL, room temperature 1 hour incubation; MMP8 enzyme concentration 500 ng/mL, room temperature, 2 hours incubation; MMP9 enzyme concentration 100 ng/mL, room temperature, 1 hour incubation; MMP10 enzyme concentration 1000 ng/mL, room temperature, 2 hours incubation; MMP12 enzyme concentration 200 ng/mL, room temperature, 1 hour incubation; MMP13 enzyme concentration 200 ng/mL, room temperature, 1.5 hours incubation; MT1-MMP enzyme concentration 200 ng/mL, room temperature, 1 hour incubation; ADAM9 enzyme concentration 4000 ng/mL, incubated at 37° C. 6 hours; ADAM10 enzyme concentration 700 ng/mL, incubated at 37° C. 6 hours; ADAM17 enzyme concentration 600 ng/mL, incubated at 37° C. 1 hour.

Correlation Studies Between Shedding and Biochemical Assays

Because Her-2 shedding occurs at the cell surface, a good correlation was expected between cell-based Her-2 sheddase inhibition and biochemical enzyme based inhibition. Accordingly, approximately 500 compounds were assayed against ADAM10 and ADAM17 (also referred to as TACE), as well as ten (10) matrix metalloproteinases (MMPs), e.g., MMP1, MMP2, MMP3, MMP7, MMP8, MMP9, MMP10, MMP12, MMP13, and MT1-MMP.

For each potential sheddase assayed, a log IC50 plot was produced graphing the IC50 for inhibition of the potential sheddase versus inhibition of Her-2 shedding. The data disclosed herein, shown in FIGS. 6-10, demonstrate that there was no correlation between enzyme inhibition and inhibition of Her-2 shedding with regard to MMP2 (FIG. 6), MMP12 (FIG. 7), ADAM17 (FIG. 8), ADAMS (FIG. 9), demonstrating that these enzymes were not potential sheddases. Points falling outside of the upper and lower parallel lines are greater than 10-fold divergent from the ideal correlation curve (middle line).

Figure 10:
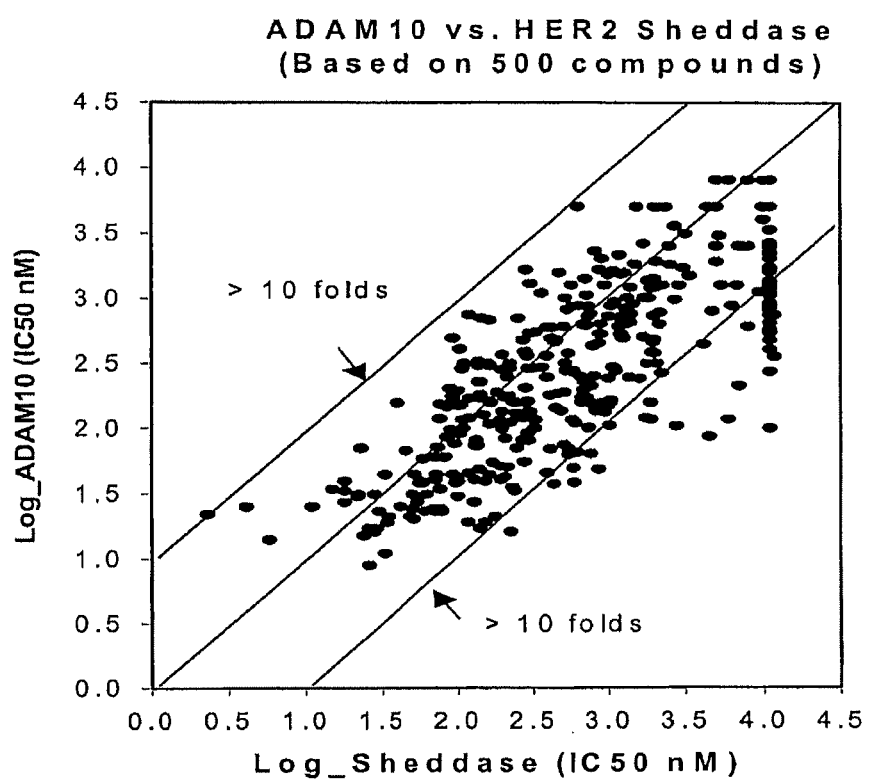
FIG. 10 is a graph depicting the strong correlation between inhibition of sheddase and inhibition of ADAM10 using over 500 compounds. The figure sets forth a graph depicting a logarithmic plot of the IC50 values of various compounds for inhibition of ADAM10 versus the IC50 values of the same compounds for inhibition of Her-2 sheddase activity. Points falling outside of the upper and lower parallel lines are greater than 10-fold divergent from the ideal correlation curve (middle line).
Figure 11:
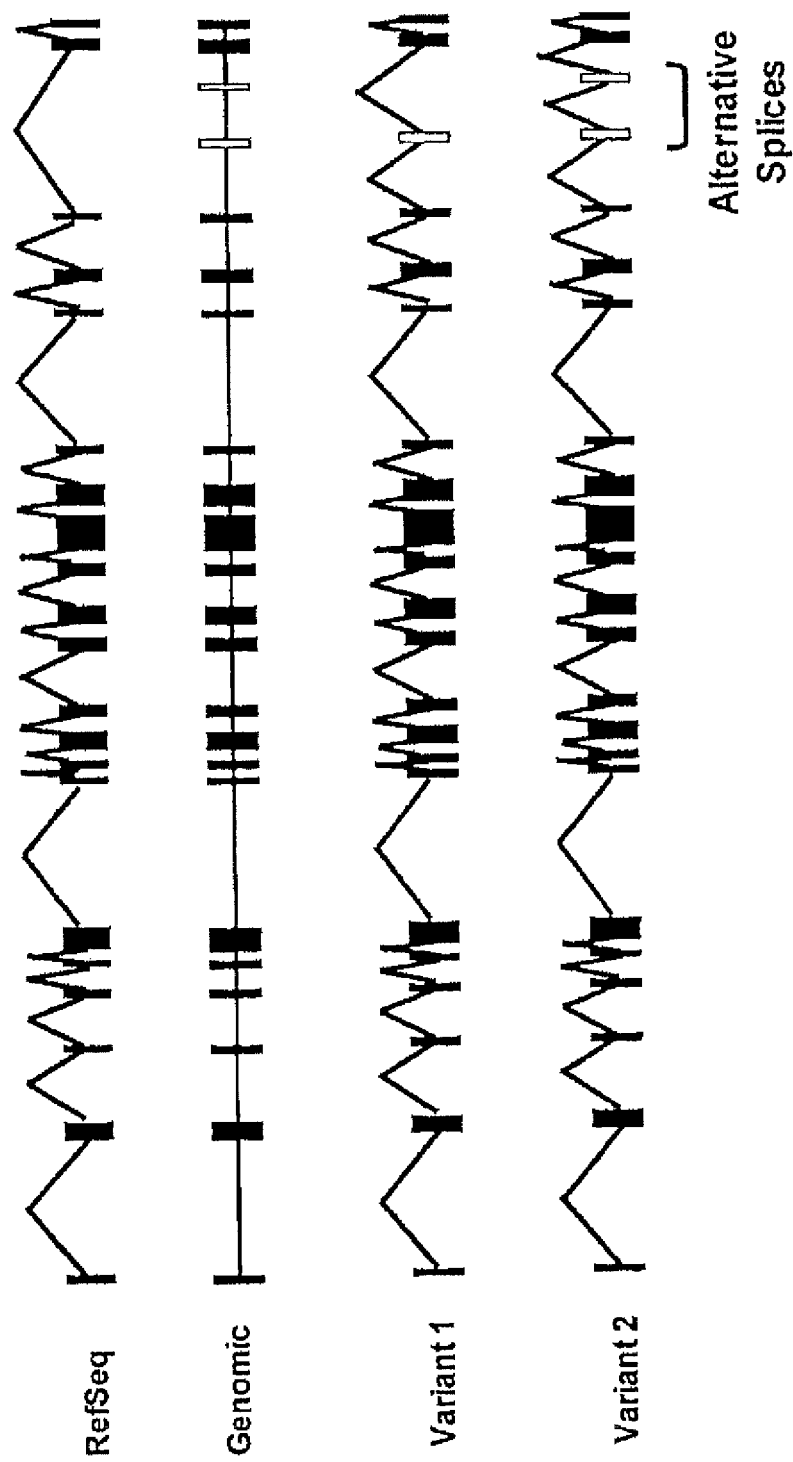
FIG. 11 is a schematic depicting alternative splicing in the human ADAM15 gene. Boxes denote exons with lines showing position of introns. The splicing pattern of the published human sequence is shown on the top just above the genome exon/intron structure. The two alternatively spliced variants are shown below the genomic structure with unshaded boxes delineating alternatively spliced exons.

The data disclosed demonstrate a strong correlation between the IC50 of compounds that inhibited ADAM10 and the IC50 of the same compounds for inhibition of Her-2 shedding (FIG. 10). These data demonstrate that ADAM10 is a sheddase.

In sum, expression of various ADAMs could be selectively inhibited using various siRNAs. Further, in cell lines that shed Her-2, ADAM10 and ADAM15, reduced Her-2 shedding. Further, biochemical inhibition data demonstrated that ADAM10 is a sheddase since compounds that inhibit Her-2 shedding also inhibited ADAM10 to the same extent. These data amply demonstrate, for the first time, that ADAM10 mediates cleavage of Her-2 to produce ECD and p95 in a cell. Thus, ADAM10 is a potential therapeutic target for treatment of diseases, disorders or conditions mediated by cleavage of Her-2 to produce ECD, p95, or both.

Identification of Novel ADAM15 Splice Variants

The data disclosed herein demonstrate alternative splicing in the coding region of ADAM15 (FIGS. 13A, 13B, 14A, and 14B). The published sequence of ADAM15 represents a shorter form than the sequence disclosed herein. Two versions of ADAM15 were cloned, the first had one additional exon (FIGS. 13A and 13B) versus the previously known published sequence and the second had two additional exons (FIGS. 14A and 14B).

RT-PCR was used to demonstrate that the version with one extra exon (variant 1) is the most abundant in the HER2 shedding and non-shedding cell lines. The nucleic acid sequence of human ADAM15 variant 1 is depicted in FIG. 13A-1 and 13A-2 (SEQ ID NO:1), while the amino acid sequence of the variant (SEQ ID NO:2) is set forth in FIG. 13B. The nucleic acid sequence of the longest variant of human ADAM15 variant 2, is set forth in FIG. 14A (SEQ ID NO:3) and the amino acid sequence of variant 2 (SEQ ID NO:4) is provided in FIG. 14B.

Comparison of the two alternatively spliced exons to rat and mouse genomic sequences indicated that the exons are conserved across species. The alternative splice forms alter the cytoplasmic tail of ADAM15. Sequences encoded by the alternatively spliced exons contain proline-rich domains with multiple consensus Src homology 3 (SH3) domain binding sequences (Mayer and Eck, 1995, Current Biology 5:364-367). These alternatively spliced sequences provide sites for protein-protein interactions between ADAM15 and SH3 domain containing proteins. Indeed, a recent description of similar splice variants in mouse (Shimizu et al., 2003, Biochem. Biophys. Res. Commun. 309: 779-785) indicates that the alternatively spliced sequences alter the binding affinity of murine ADAM15 for Src family proteins Lck and Src. Without wishing to be bound by any particular theory, the various novel splice variants of ADAM15 may relate to cleavage of Her-2 and provide potential targets for development of useful therapeutics relating to inhibition of Her-2 cleavage. This is especially true where one of the variants, human ADAM15 variant 1, appears to be correlated with Her-2 shedding.

Example 2

Synergistic Anti-Tumor Effect between MPI and a Her-2 Antagonist Antibody

The data disclosed herein demonstrate successful inhibition of tumor cell growth using newly identified inhibitors, e.g., MPIs, of the enzymatic processing of Her-2 (p185). These inhibitors can be potential therapeutics for development of therapy for Her-2 overexpressing and/or ECD shedding cancers. Briefly, cell lines in which Herceptin™ induces arrest of malignant cell growth arrest were studied. Inhibition of Her-2 receptor processing by metalloprotease inhibitors alone, or in combination with suboptimal concentrations of Herceptin™ can arrest the growth and impact the susceptibility to apoptosis of Her-2 overexpressing breast cancer cell line cells. Further, the data disclosed herein demonstrate the surprising synergy of Herceptin™ and MPI in arresting the cell growth of malignant cells that overexpress Her-2.

The materials and methods are now described.

Cells, Compounds, Drugs and Other Reagents

Human breast cancer cell lines BT-474 (# HTB-20), SKBR-3 (#HTB-30) and MCF-7 (# HTB-22) were obtained from the American Type Tissue Culture Collection (ATCC, Manassas, Va.). Cells were routinely maintained in media recommended by the ATCC with slight modifications. Cells were kept at 37° C. in a humidified incubator supplied with 5% $CO_2$. BT-474 cells were grown in RPMI 1640 (Invitrogen) supplemented with 10% fetal bovine serum (FBS), 0.01 mg/ml bovine insulin, 10 mM HEPES and 0.1 mM non-essential amino acids. SKBR-3 cells were grown in McCoy's 5a (Invitrogen) supplemented with 10% FBS. MCF-7 cells were kept in Eagle's minimal essential medium (ATCC) supplemented with 10% FBS and 0.01 mg/ml bovine insulin. Both BT-474 and SKBR-3 cells overexpress Her-2 on the surface and have high level of Her-2 cleavage, but MCF-7 cells do not overexpress Her-2. Herceptin™, Paclitaxel™ (Taxol™) and Cisplatin™ were purchased from Hanna Pharmaceuticals (Wilmington, Del.). Herceptin™ was prepared as a stock solution (1 mg/mL) in sterile water once every four weeks to maintain its activity.

Compounds (MPIs) used in the below experiments included Compound 5 (((6S,7S)-N-hydroxy-5-methyl-6-{[4-

(2-methyl-4-nitrophenyl)piperazin-1-yl]-carbonyl}-5-azaspiro[2.5]octane-7-carboxamide), Compound 6 ((6S,7S)-N-hydroxy-5-methyl-6-({4-[5-(trifluoromethyl)pyridin-2-yl]piperazin-1-ylcarbonyl)-5-azaspiro[2.5]octane-7-carboxamide), Compound 8 ((1S,2S)-2-(4-(4-fluorophenyl)piperazin-1-yl)carbonyl)-N-hydroxycyclohexanecarboxamide), Compound 4 ((3R)-N-hydroxy-2-((4-methoxyphenyl)sulfonyl)-1,2,3,4-tetrahydroisoquinoline-3-carboxamide), and Compound 7 (Prinomastat), each of which can be obtained commercially, made according to the literature, or prepared according to the methods described in U.S. Ser. No. 60/534,501, the disclosure of which is incorporated herein by reference in its entirety. All compounds used in these studies were routinely prepared as 5 mM stocks in 100% DMSO (Sigma).

Tumor specimens were obtained by Oncotech (Tustin, Calif.) according to their IRB approved protocol using standard procedures known in the art. Cell cultures were maintained in tissue culture flasks. Cells intended for experimental treatment were harvested in log phase with EDTA and were plated at a density of $1 \times 10^5$ cells/well in 24-well polystyrene plates in 0.5 ml RPMI with 10% FCS. Experiments to determine the effects of MPIs on shed Her-2 receptor were performed as described below for BT-474 cells.

Cell Proliferation Assays

Proliferation assays were routinely performed with two protocols: cell counting and BrdU incorporation assay. For cell counting, cells ($1 \times 10^5$) were seeded in each well of 12 well plates and cultured overnight. Then, cells were treated for 6 days with drugs and compounds as indicated in individual experiments. Culture media were replaced with fresh media containing the same concentrations of drugs and compounds after the first 3 days of treatment. Viable cells were counted with hemacytometers immediately after trypan blue staining.

The BrdU incorporation assay was performed using a colorimetric Cell Proliferation ELISA kit per manufacturer's instruction (#1647229, Roche Molecular Biochemicals), measuring DNA synthesis in proliferating cells. Briefly, cells ($5-10 \times 10^3$) were seeded in each well of 96 well plates and cultured overnight. The next day, culture media were replaced with fresh media containing drugs and compounds as indicated for individual experiments. After 2-6 day treatment, 10 µM (final concentration) of BrdU labeling solution was added into the medium and the cells were incubated for an additional 4-5 hours at 37° C. The labeling medium was removed, and 200 µl/well FixDenat added to the cells and incubated for 30 minutes at room temperature. The FixDenat solution was thoroughly removed, and 100 µl/well anti-BrdU-POD antibody conjugate working solution added and incubated for 90 minutes at room temperature. Then the antibody conjugate was removed and the cells were rinsed three times with 200 µl/well washing solution. Finally, 100 µl/well of substrate solution was added and the results were obtained using a microplate reader (Spectra Max PLUS, Molecular Devices) during color development. Multiple readings at various time points were obtained and results in the linear range of the assay were obtained. The data disclosed herein represent average numbers and standard deviations of representative, replicated experiments are presented. Appropriate controls were included for the assays.

Apoptosis Assays

Apoptosis assays were performed with a Cell Death Detection ELISA$^{PLUS}$ kit (cat. no. 1774425, Roche Molecular Biochemicals) measuring DNA fragmentation in apoptotic cells. Briefly, cells ($1 \times 10^4$) were seeded in each well of 96 well plates and cultured overnight. On the next day, culture media were replaced with fresh media containing drugs and compounds as indicated in individual experiments. After 3 day treatment, the cells were spun down at 200×g for 10 minutes and the supernatant was removed carefully. The cell pellet was resuspended in 200 µL lysis buffer and incubated for 30 minutes at room temperature. The lysate was centrifuged at 200×g for 10 minutes. 20 µL of the supernatant was transferred into another microplate. 80 µL of the appropriate immunoreagent was added to each well. The microplate was covered with an adhesive cover foil and shaken gently for about 2 hours at room temperature. The solution was removed and the plate was rinsed 3 times with 250 µL/well incubation buffer. Finally, 100 µL/well ABTS solution was added and the results were read with a microplate reader Spectra Max PLUS (Molecular Devices) during color development. Multiple readings at various time points were obtained and results in the linear range of the assay were obtained. Average numbers and standard deviations of representative, replicated experiments are presented. Appropriate controls were included in the assays.

Her-2 ELISA

BT474 cells were seeded in 100 µL of RPMI medium containing 10% FCS+10 µg/ml insulin in 96 well plates at $2 \times 10^4$ cells/well. The cells were incubated overnight at 37° C. The following morning, the media was removed and 100 µL of fresh media with or without compound was added back. The cells were incubated for about 72 hours at 37° C. After about 72 hours, the supernatants were removed. The samples were diluted 1:10 and analyzed using a commercially available Her-2 ELISA kit per manufacturer's instructions (Oncogene Research, catalog #QIA 10).

Western Blot

BT474 cells were seeded in 1 mL of RPMI medium containing 10% FCS+10 µg/ml insulin in 12 well plates at $1 \times 10^5$ cells/well. The cells were incubated overnight at 37° C. The following morning, the media was removed and 1 mL of fresh serum-free RPMI media+/− compound was added back. The cells were incubated for 5 days at 37° C. After 5 days, the supernatants were removed. 15 µL of supernatant was added to 15 µL of sample buffer (Novex, catalog #LC2676) and the samples were loaded onto a 4-12% Tris-Glycine gradient gel (Novex, EC6035). The samples were separated for 2 hours at 125 volts. The gels were then transferred onto PVDF membrane (NEN, catalog #NEF-100) at 30 volts overnight in the cold. The following morning, the blots were blocked in 5% milk/PBS/0.05% Tween-20 for 1 hour at room temperature. Her-2 antibody (NeoMarkers, catalog #MS-1350-P1) was diluted 1:200 in 5% milk/PBS/0.05% Tween-20 and incubated with the blots for 2 hours at room temperature. The blots were washed 5 times (10 minutes each wash) in PBS/0.05% Tween-20. An HRP-conjugated goat anti-mouse IgG antibody was diluted 1:2000 and added to the blots for 1 hour at room temperature, The blots were washed 5 times (10 minutes each wash) in PBS/0.05% Tween-20. The blots were then incubated for 5 minutes with SuperSignal West Pico Chemiluminescent substrate (Pierce, catalog #34080) and exposed to film.

In experiments to determine the effects of MPI treatment on cell signaling, BT474 cells were plated at 1×105 cells/mL in 2 mL of media (RPMI+10% FCS+10 µg/mL insulin) in 12-well plates. The following morning, the media was replaced and the cells were treated with MPI or Herceptin for 5 days, changing the media and replacing MPI on day 3. After 5 days, the cells were harvested, lysed in 200 µL ice-cold lysis buffer containing 10 mM Tris, pH 7.2, 150 mM NaCl, 1% Triton X-100, 1% deoxycholic acid, 0.1% SDS, 50 µg/mL leupeptin, 50 µg/mL aprotinin, 1 mM sodium vanadate, 50 mM sodium fluoride, 1 mM PMSF. After 10 minutes on ice, the samples were microfuged at 13,000 rpm for 10 minutes at 4° C. and the supernatants collected. For analysis, 15 µL of 2× Laemmli sample buffer (BioRad, cat#161-0737) was added to 15 µL of extract, samples boiled for 5 minutes and loaded onto 12-well 12% Tris-Glycine gels (Novex, cat# EC60052). Gels were run in 1× Tris-Glycine-SDS buffer (Gibco BRL) using Novex minigel apparatus for approximately 1.5 hours. Following electrophoresis, proteins were transferred onto PVDF membrane (NEN, cat#NEF1000) in 1× Tris-Glycine buffer (Biorad, cat#161-0734) containing 20% MeOH for 2-3 hours using BioRad miniblot transfer system. After transfer, membranes were blocked in PBS+5% milk+0.1% Tween-20 for 1 h at RT. Primary antibody (anti-pERK, 1:1000, NEB, cat#9101 or anti-phospho-AKT, 1:1000, NEB, cat#9271) was added in 15 mL of PBS+5% milk+0.1% Tween-20 and incubated overnight in the cold. The blots were washed 3×, 15 minutes each in PBS+0.1% Tween-20. Horseradish peroxidase-conjugated secondary antibody (goat anti-rabbit IgG, 1:2000, NEB, cat#7074) was diluted in 15 mL of PBS+5% milk+0.1% Tween-20 and incubated with the blot for 1 hour at RT. The blots were washed 3×, minutes each in PBS+0.1% Tween-20. Chemiluminescent detection reagent (Pierce, cat#34080) was added to the blot and incubated 5 minutes at RT before exposing to film.

Identification of Her-2 Sheddase Inhibitors

A series of hydroxamic acid-based metalloproteaase inhibitors (MPIs) were tested, including, but not limited to, TAPI, Compound 5, Compound 6, Compound 8, Compound 4, and Compound 7. These inhibitors were added, at varying concentrations, to cultures of BT474 cells, a Her-2 overexpressing breast cancer cell line known to enzymatically process cell surface Her-2 (p185) and release the extracellular domain (ECD) into the culture supernatant, i.e., shedding of ECD. After 72 hours, cell culture supernatants were harvested and assayed for Her-2 ECD content using an ELISA assay.

Figure 15:
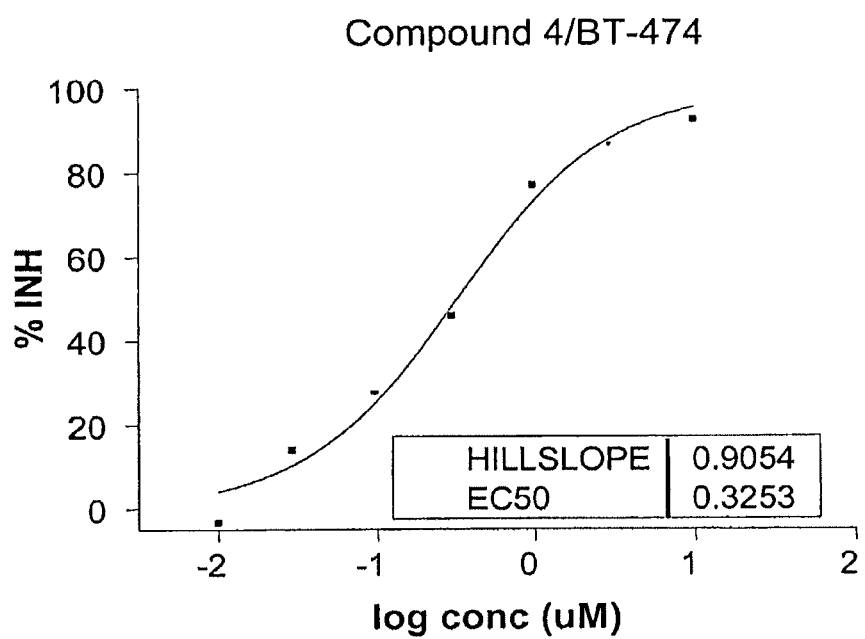
FIG. 15 is a graph depicting inhibition of Her-2 cleavage by a representative MPI (Compound 4) in Her-2 overexpressing BT-474 cells.
Figure 16:
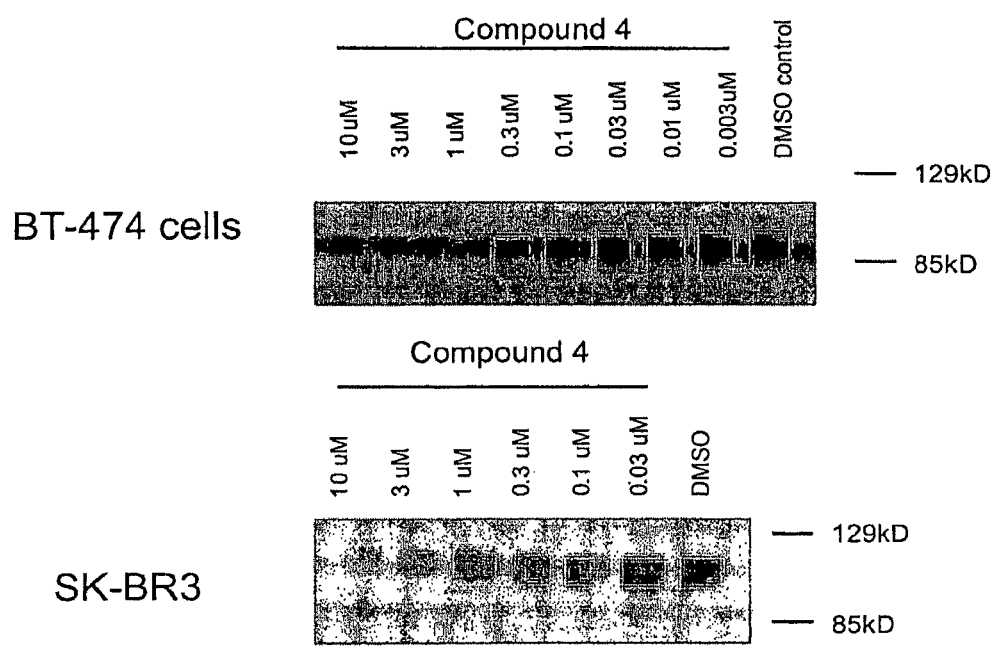
FIG. 16 is an image of a Western Blot depicting inhibition of Her-2 cleavage in BT-474 cells (top panel) and in SK-BR3 cells (bottom panel) at varying concentrations of the MPI Compound 4. Both cell lines overexpress Her-2. The Western Blot assessed the presence of a protein of about 105 kDa, the size of Her-2 ECD, in culture supernatants and confirmed the ELISA results indicated at the right of each panel.
Figure 17:
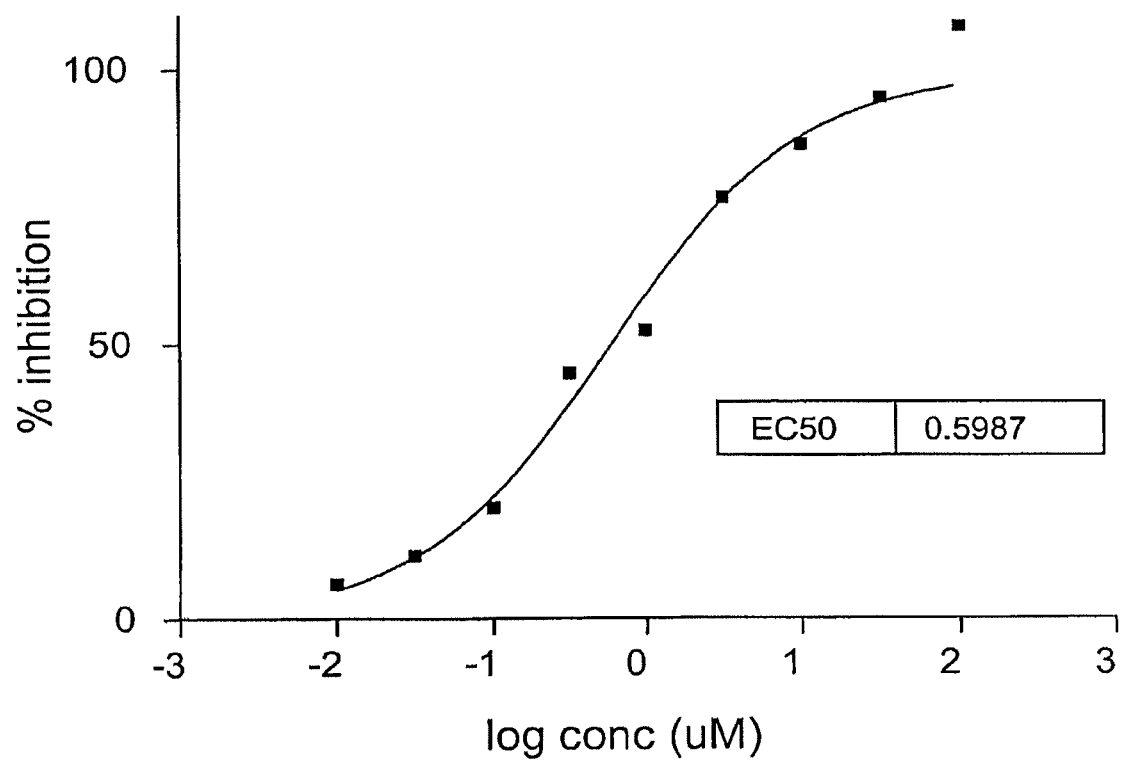
FIG. 17 is a graph depicting inhibition of Her-2 cleavage by a representative MPI (Compound 4) in a primary breast tumor cell line that over expresses Her-2.

The MPIs tested varied widely in efficacy, from almost no inhibition at 10 µM to about 50% inhibition of ECD processing at 10-50 nM. The results obtained using a representative compound is depicted in FIG. 15. ELISA results were confirmed by Western blotting. Western blotting of culture supernatants identified the presence of a protein of approximately 105 kDa, the size of the Her-2 ECD, which is recognized by an anti-Her-2 ECD reactive monoclonal antibody. The presence of this band is reduced or abolished by those MPIs scoring as effective inhibitors in the Her-2 ECD ELISA (FIG. 16). MPIs that detectably inhibited Her-2 cleavage to produce a level of ECD, which was less than the level of ECD produced in the absence of the inhibitor, are termed active inhibitors of "sheddase" in that they inhibit shedding of the ECD upon cleavage of Her-2 (p185). The compound was also effective in blocking ECD processing in a primary breast tumor cell that overexpresses Her-2 (FIG. 17).

To examine the biological consequences of Her-2 processing, varying concentrations of an active (Compound 5), or a structurally related but inactive (Compound 6) Her-2 sheddase inhibitor, were added to cultures of BT474 cells. In some cases, these cultures were also supplemented with varying concentrations of Herceptin™. After varying periods of cell culture (2-6 days), the cell cultures were harvested and cell growth was assessed by cell count and BRdU incorporation using standard protocols.

As demonstrated by the data disclosed herein, at concentrations below 5 µM, MPI alone did not detectably affecte the growth of the cancer cell line. At higher concentrations of each compound, nonspecific effects were detected which likely reflect chemical toxicity.

Administration of Herceptin™ to the cells led to growth inhibition in a concentration dependent manner, with a maximal effect of approximately 50% inhibition at concentrations above 1 µg/ml. At 0.2 µg/ml, Herceptin™ was without significant effect on BT474 cell growth.

Figure 19:
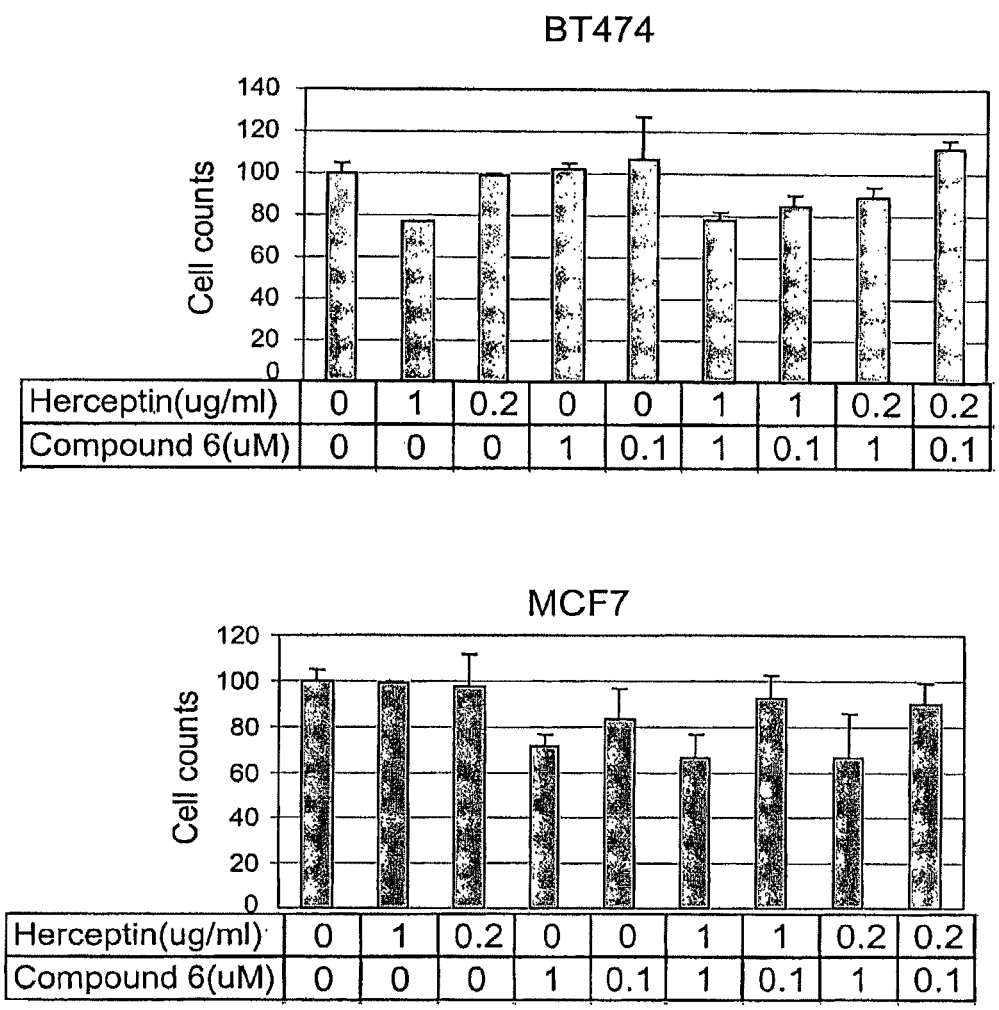
FIG. 19 is a diagram depicting that at the concentrations indicated, Her-2 sheddase inactive inhibitor Compound 6 (but MMP-active) does not enhance the antiproliferative activity of a suboptimal dose of Herceptin™ in either Her-2 overexpressing BT474 (top panel) or MCF7 cells which do not overexpress Her-2 (bottom panel). Compound 6: Her-2 sheddase (inactive), MMP12 IC50 (1.95 nM), MMP2 IC50 (0.65 nM).

Surprisingly, the combination of suboptimal doses of Herceptin™ and an active Her-2 sheddase inhibitor, but not the structurally related, but inactive, Her-2 sheddase inhibitor, reduced BT474 cell growth more efficiently than optimal concentrations of Herceptin™ alone or the sheddase inhibitor alone (FIGS. 18 and 19). This synergistic pattern was also observed with SKBR3, another Her-2 overexpressing breast cancer cell line which sheds Her-2 ECD.

In contrast, the growth of MCF7 breast cancer cell line, which expresses basal levels of Her-2 and does not shed ECD in vitro, was not significantly impacted by Herceptin™, the active Her-2 sheddase inhibitor, or the combination of Herceptin™ antibody and active sheddase inhibitor (FIGS. 18 and 19). These results demonstrate that MPI-mediated inhibition of Her-2 ECD shedding can synergize with suboptimal concentrations of Herceptin™ to induce growth arrest of Her-2 overexpressing breast cancer cell line cells. Further, the data disclosed herein demonstrate that the synergistic effect is mediated by, or is associated with, inhibition of the processing of full-length Her-2 (p185) into an ECD domain that can be shed and a cell-associated constitutively active kinase portion (p95) since, unlike cells that overexpress p185 and shed ECD, cells that do not over-express Her-2 or shed ECD, are not growth-inhibited by treatment with Herceptin™ and/ or an active MPI of sheddase.

Figure 22:
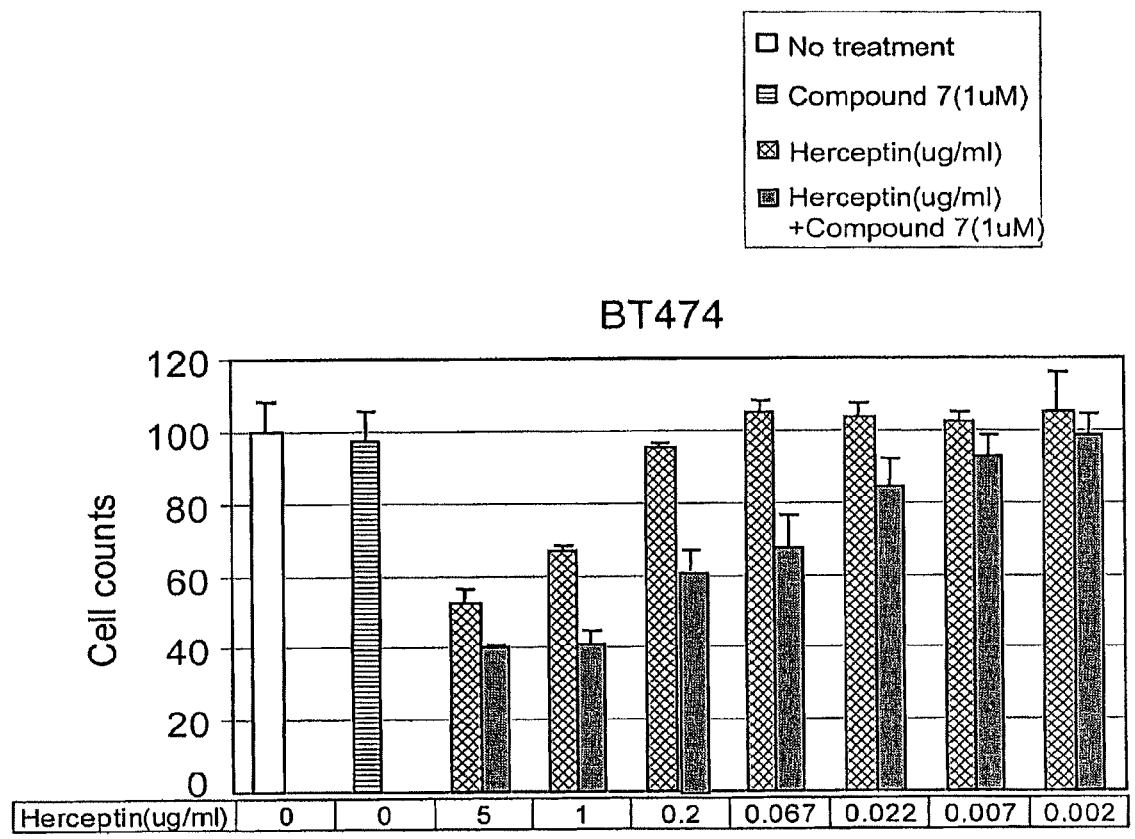
FIG. 22 is a graph depicting that a broad specificity MP inhibitor, Compound 7, synergistically enhances the antiproliferative activity of a suboptimal dose of Herceptin™ in Her-2 overexpressing BT474 cells. Synergistic enhancement has been detected when cells were treated with suboptimal doses of Herceptin™ ranging from 0.067 to 5 μg/ml and an efficacious dose (1 μM) of Compound 7. Compound 7: Her-2 sheddase IC50 (20-100 nM).

In a separate study, a broad specificity sheddase inhibitor (Compound 7) was shown to synergistically enhance the antiproliferative activity of suboptimal doses of Herceptin™ in Her-2 overexpressing BT474 cells. Synergistic enhancement of the anti-proliferative effect was detected when cells were treated with suboptimal doses of Herceptin™ ranging from 0.067 to 5 µg/ml and an efficacious dose (1 µM) of Compound 7 (FIG. 22).

Her-2 Downstream Signaling Studies

It has been shown by previous studies that overexpression of Her-2 leads to the phosphorylation and activation of the MAP kinase and AKT signal transduction pathways, and that this event is critical for cell proliferation and survival. In addition, treatment of cancer cells using optimal concentrations of Herceptin™ has been shown to block activation of both pathways, presumably resulting in the growth arrest observed. Since the sheddase inhibitor in combination with low doses of Herceptin™, led to growth inhibition of Her-2 overexpressing cells at a surprising level indicating synergism, the effect of this treatment on the MAP kinase and AKT signaling pathways was examined.

Figure 20:
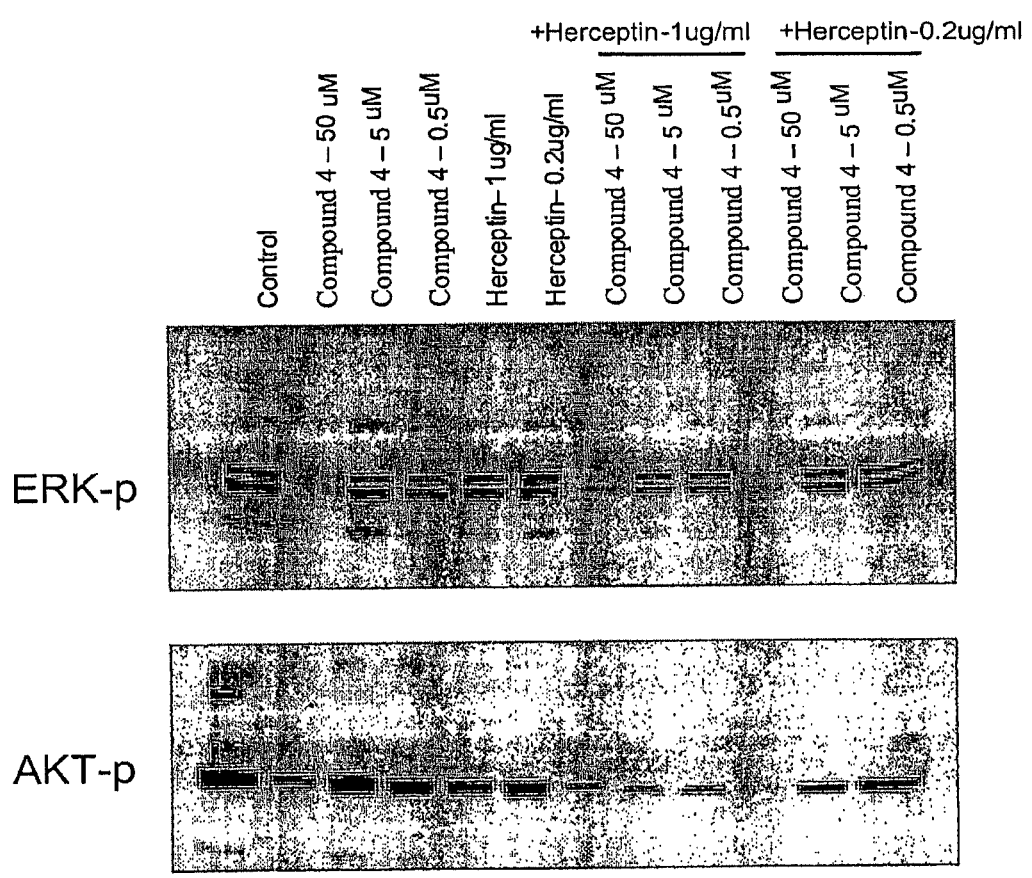
FIG. 20 is an image of a gel depicting the synergistic inhibition of ERK (top panel) and AKT (bottom panel) phosphorylation in Her-2 overexpressing BT474 cells by Herceptin and the MPI Compound 4, at the concentrations indicated.

Phosphorylation of AKT and the MAP kinase ERK were monitored by western blot analysis using phospho-specific antibodies. Cultures of BT474 cells were treated for 6 days with varying concentrations of the sheddase inhibitor alone or in combination with Herceptin™. Similar to the results observed on cell growth, treatment of BT474 cells with 0.2 µg/ml Herceptin™ in combination with the sheddase inhibitor (Compound 4) led to a detectable reduction in phosphorylation of both AKT and ERK. Treatment of cells with either the sheddase inhibitor at concentrations of less than 5 µM or 0.2 µg/ml Herceptin™ alone did not demonstrate a detectable effect on AKT or ERK phosphorylation (FIG. 20). Further, these pathways were not impacted in the Her-2 non-overexpressing MCF7 cells following treatment with Herceptin™, the sheddase inhibitor or the synergistic combination of these compounds.

Without wishing to be bound by any particular theory, the data disclosed herein demonstrate that the synergy observed with Herceptin™ and the sheddase inhibitor on cell growth has a biochemical basis, apparently resulting, at least in part, from inhibition of the AKT and/or MAP kinase pathway(s).

Figure 21:
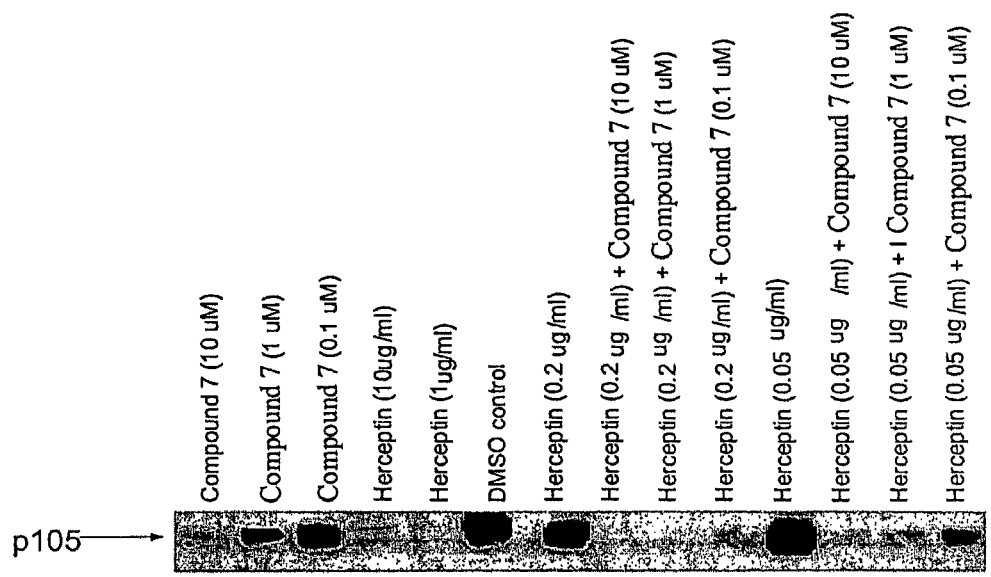
FIG. 21 is an image of a Western blot depicting inhibition of Her-2 cleavage in BT-474 cells at varying concentrations of a representative MPI (Compound 4) alone, Herceptin alone or the MPI in combination with Herceptin. The Western blot assessed the presence of a protein of about 105 kDa, the size of the Her-2 ECD in culture supernatants and demonstrates an additive effect of Herceptin and the MPI in blocking Her-2 cleavage.

Consistent with published reports, saturating amounts of Herceptin prevent Her-2 cleavage in vitro (FIG. 21). However, at suboptimal doses of Herceptin, this does not occur. The MPI together with low doses of Herceptin are at least additive in preventing Her-2 cleavage. This occurs at the same doses where synergistic effects of Herceptin and the MPI are observed on cell growth.

The studies disclosed herein demonstrate, for the first time, that a Her-2 sheddase inhibitor potentiates the effects of Herceptin™ in blocking the growth of Her-2 overexpressing breast cell lines in vitro, and appears to inhibit the AKT and/or MAP kinase pathway(s). These data demonstrate that an inhibitor of Her-2 processing can be a useful therapeutic in patients with Her-2 overexpressing breast cancer as part of a multidrug treatment regimen, which treatment can include Herceptin™.

Figure 23:
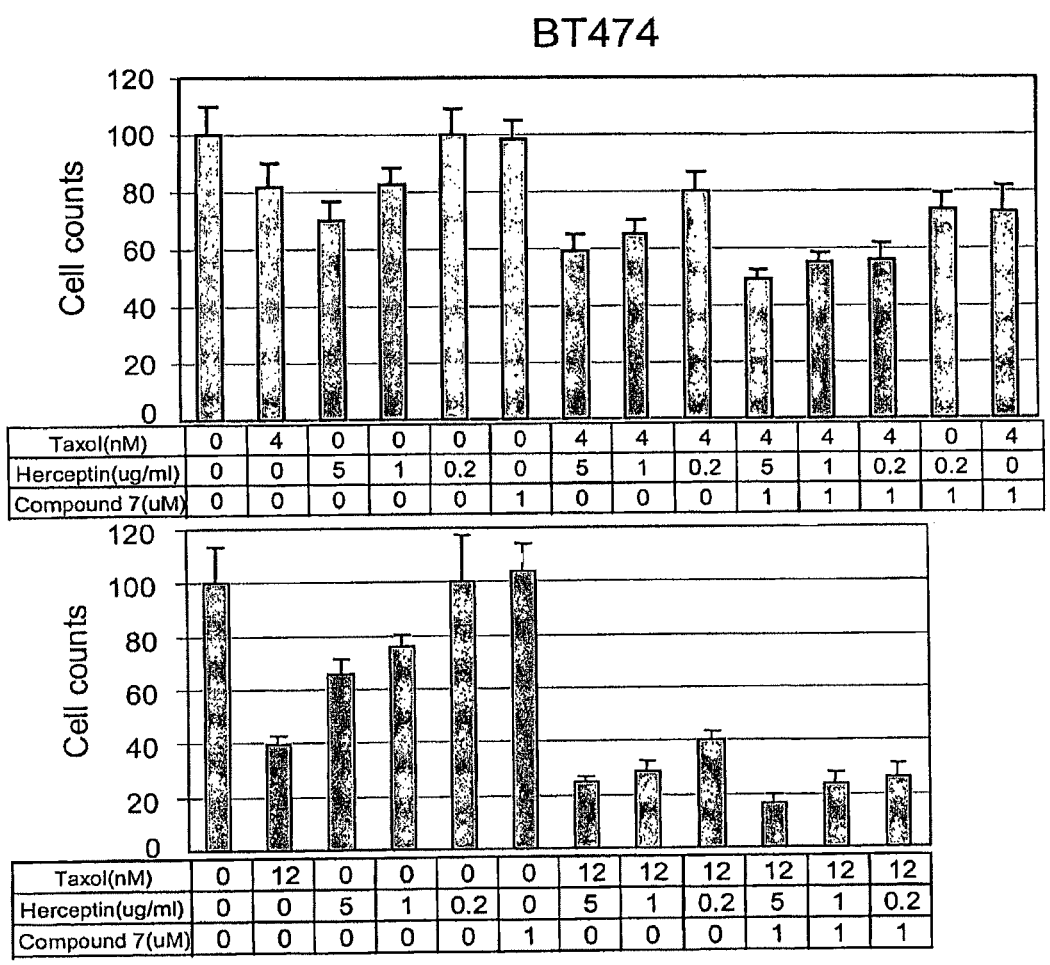
FIG. 23 is a graph depicting that at the concentrations indicated, combinations of Compound 7 and Herceptin™ significantly enhance the antitumor activity of Taxol™ in Her-2 overexpressing BT474 cells. Significant enhancement was also detected in similar studies in which Taxol™ was replaced with other chemotherapeutic agents (e.g., Cisplatin™), as well as in other Her-2 overexpressing breast cancer cell lines (e.g., SKBR3). Compound 7: Her-2 sheddase IC50 (20-100 nM).
Figure 24:
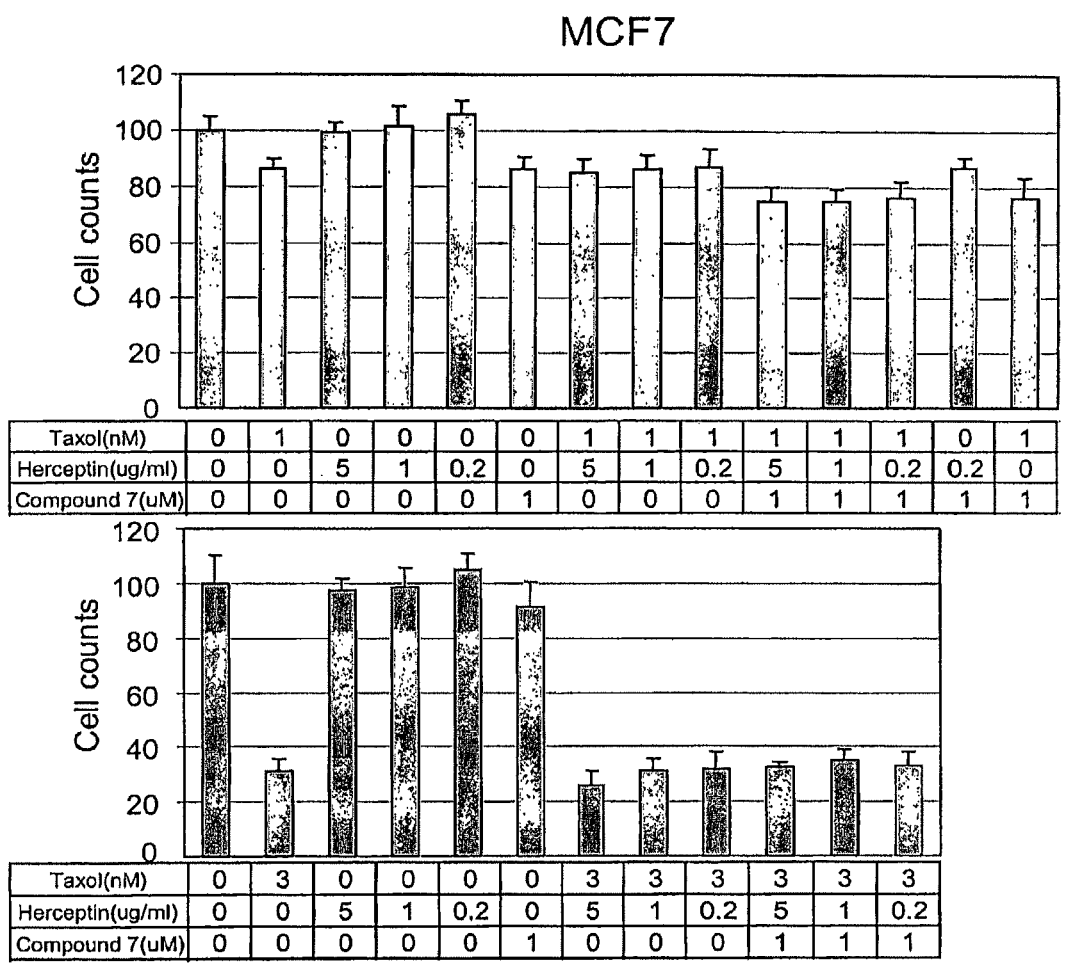
FIG. 24 is a graph depicting that at the concentrations indicated, combinations of Compound 7 and Herceptin™ have no effect on antitumor activity of Taxol™ in MCF7 cells that do not overexpress Her-2. Similarly, no effect was detected in similar studies in which Taxol™ was replaced with other chemotherapeutic agents (e.g., Cisplatin™) in MCF7 cells.
Figure 25:
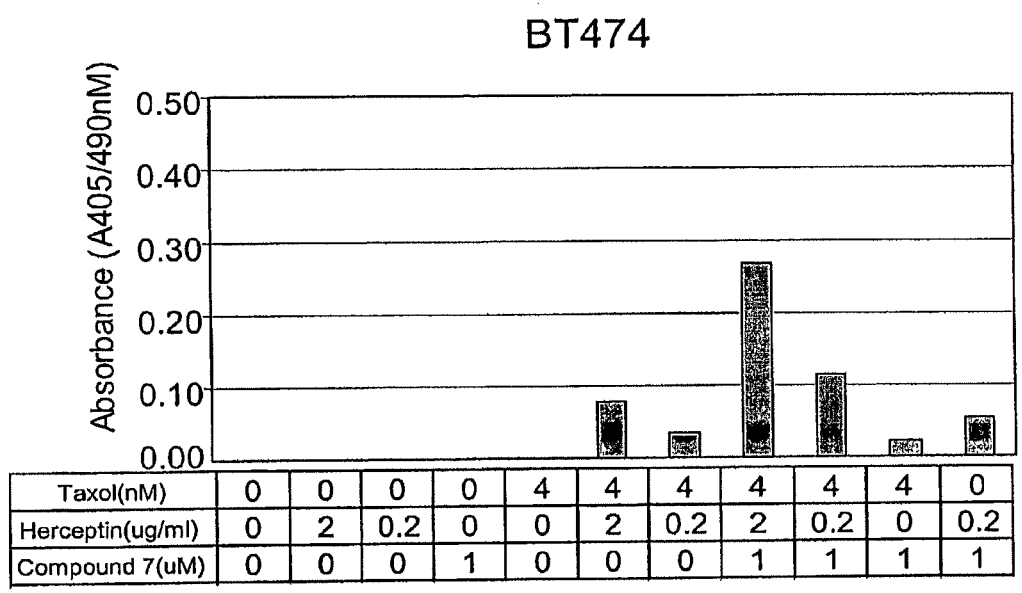
FIG. 25 is a graph depicting that at the concentrations indicated, combinations of Compound 7 and Herceptin™ significantly enhance Taxol™-inducing apoptosis of Her-2 overexpressing BT474 cells. The increased level of apoptosis was also detected in similar studies in which Taxol™ was replaced with other chemotherapeutic agents (e.g., Cisplatin) in BT474 cells, as well as in other Her-2 overexpressing breast cancer cell lines (e.g., SKBR3), but not in MCF7 cells, which do not overexpress Her-2. Compound 7 Her-2 sheddase IC50 (20-100 nM).

Combinations of Sheddase Inhibitors and Herceptin™ Enhance the Antitumor Activity of Chemotherapeutic Agents in Her-2 Overexpressing Breast Cancer Cells To further explore potential clinical applications of the synergism disclosed herein between sheddase inhibitors and Herceptin™, antitumor activity of standard chemotherapeutic agents (e.g., Taxol™ and Cisplatin™) was evaluated in combination with sheddase inhibitors (e.g., Compound 7) and Herceptin™ in breast cancer cell lines BT474, SKBR3 and MCF7 cells. The results show that combinations of Compound 7 and Herceptin™ significantly enhance the antitumor activity of Taxol™ and Cisplatin™ in Her-2 overexpressing BT474 and SKBR3 cells, but not in MCF7 cells that do not overexpress Her-2 (FIGS. 23 and 24).

Without wishing to be bound by any particular theory, the results suggest the enhanced synergistic antitumor activity by combinations of Herceptin™ and sheddase inhibitors (e.g., Compound 7) is mediated through a specific effect (e.g., inhibition of Her-2 cleavage) on Her-2 by the sheddase inhibitor in Her-2 overexpressing cells. The results further demonstrate that triple combinations of cytotoxic agent(s) (e.g., Taxol™ or Cisplatin™), Herceptin™ and sheddase inhibitors (e.g., Compound 7) have superior antitumor activity compared with any agent used singly, or combinations of any two of the three agents.

It has been reported previously that chemotherapeutic agents (e.g., Taxol™ and Cisplatin™) can induce programmed cell death or apoptosis in breast cancer cells. Accordingly, studies were conducted to determine whether the synergism between sheddase inhibitor(s) and Herceptin™ could affect apoptosis induced by Taxol™ or Cisplatin™ in breast cancer cells. Surprisingly, the combinations of sheddase inhibitor Compound 7 and Herceptin™ synergistically enhanced apoptosis induced by Taxol™ or Cisplatin™ in Her-2 overexpressing BT474 and SKBR3 cells, but not in MCF7 cells that do not overexpress Her-2.

These results indicate that the enhanced apoptosis induced by combinations of a cytotoxic agent (e.g., Taxol™), an antagonistic antibody (e.g., Herceptin™), and a sheddase inhibitor (e.g., Compound 7) is mediated through a specific effect (e.g., inhibition of Her-2 cleavage) on Her-2 by the sheddase inhibitor in Her-2 overexpressing cells. The results further demonstrate that triple combinations of cytotoxic agent(s) (e.g., Taxol™ or Cisplatin™), antagonistic antibody (exemplified by Herceptin™), and a sheddase inhibitor (e.g., Compound 7) induce the highest level of apoptosis over any single agents of the three or combinations of any two of the three agents. Conceivably, this combined synergistic effect of the three agents on the induction of apoptosis can partially contribute to overall enhanced antitumor activity.

Example 3

Synergistic Effect of MPIs and Inhibitors of EGFR Tyrosine Kinase Family Members The data disclosed herein demonstrate, for the first time, that combinations of sheddase inhibitors and Herceptin™ enhance antiproliferative activity of Iressa™ (an EGFR1 selective kinase inhibitor) in Her-2 overexpressing breast cancer cells.

From a genetics point of view, cancer is a type of diseases resulting from abnormal and complicated actions of multiple genes (or their encoded proteins) that play important roles in the formation, progression and maintenance of the disease (Ponder, 2001, Nature 411:336-341). Those genes are commonly classified into, but not limited to, proto-oncogenes, oncogenes and tumor suppressor genes. The actions of the genes or their encoded proteins include, but are not limited to, alterations of their genetic codes or in the level of their expression and/or activity in cancerous cells. Many receptor tyrosine kinases (e.g., EGFR family kinases) belong to the class of proto-oncogenes (Blume-Jensen. et al., 2001, Nature 411:355-365). When mutated or activated alone or with other cancer-related genes, they can cause the transformation of normal cells into cancerous cells. Alterations and activation of these cancer-causing genes are frequently detected in cell lines and primary tissues isolated from cancer patients. Accordingly, these types of genes are often targeted for cancer prevention and intervention. Nonetheless, to date, effective cancer therapy based on control of cancer genes has not been achieved, and there remains a large unmet need for such therapies. Moreover, there is a long-felt need for tools for the development of such therapies.

To explore the potential utility of the synergism detected between sheddase inhibitors and Herceptin™, studies were conducted to determine whether combinations of sheddase inhibitors and Herceptin™ could enhance the antiproliferative activity of Iressa™, a synthetic small molecule kinase inhibitor selectively active against EGF receptor-1. Iressa™, developed by AstraZeneca, has demonstrated antitumor activity against a variety of cancer cells including, but not limited to, breast cancer cells. Iressa™ acts to antagonize cancer cell growth by inhibiting EGFR1-mediated signaling and mitogenesis. Recently, Iressa™ was approved for the treatment of non-small cell lung cancer patients in Japan, Australia, and the United States.

Figure 26:
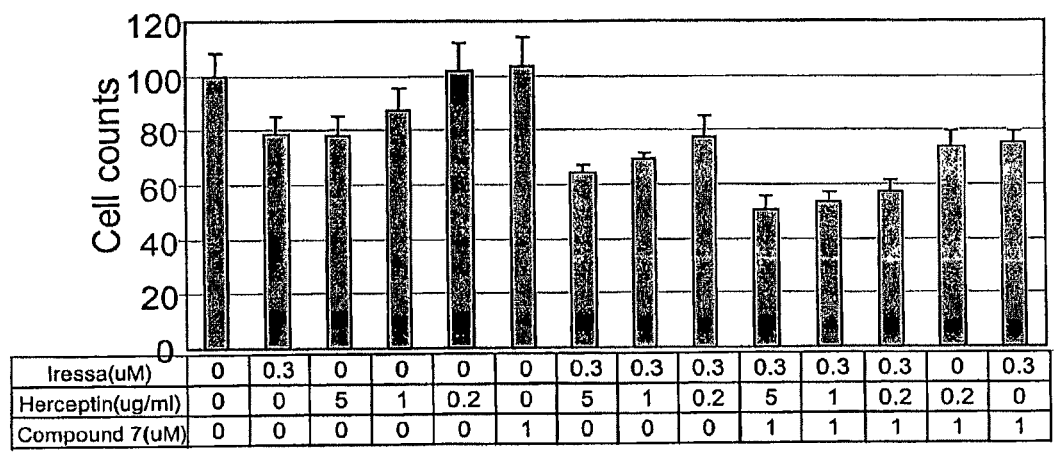
FIG. 26 is a graph depicting that at the concentrations indicated, combinations of Compound 7 and Herceptin™ enhance the antiproliferative activity of Iressa™ in Her-2 overexpressing BT474 cells. No enhanced antiproliferative activity of Iressa™ has been detected in MCF7 cells that do not overexpress Her-2. Iressa™ is a synthetic small molecule kinase inhibitor that selectively inhibits epidermal growth factor receptor-1. Compound 7: sheddase IC50 (20-100 nM).

The results from the proliferation assay (FIG. 26) demonstrate that combinations of sheddase inhibitor (e.g., Compound 7) and Herceptin™ synergistically enhanced the antiproliferative activity of Iressa™ in Her-2 overexpressing breast cancer BT474 cells, but not in MCF7 cells that do not overexpress Her-2. The result presents a different therapeutic strategy than the one that combines cytotoxic agent(s) (e.g., Taxol and Cisblastin), Herceptin™ and sheddase inhibitor(s).

The data disclosed herein demonstrates that in a Her-2 overexpressing tumor, combining sheddase inhibitors (e.g., Compound 7), a Her-2 antagonistic antibody (e.g, Herceptin™), and a third therapeutic agent (cytotoxic or cytostatic, gene/protein target-based, including, but not limited to, Iressa™), which by itself at least also possesses detectable antitumor activity, greater synergistic anti-tumor activity was achieved.

Example 4

In Vivo Activity of MPIs

This example describes in vivo studies carried out with selective inhibitors of Her-2 shedding including, Compound 1 (methyl (6S,7S)-7-[(hydroxyamino)carbonyl]-6-[(4-phenyl-3,6-dihydropyridin-1(2H)-yl)carbonyl]-5-azaspiro[2.5]octane-5-carboxylate) and Compound 2 (methyl (6S,7S)-7-[(hydroxyamino)carbonyl]-6-[(4-phenylpiperazin-1-yl)carbonyl]-5-azaspiro[2.5]octane-5-carboxylate), in a breast cancer xenograft model with a cell line overexpressing Her-2. These results, indicating a strong correlation between the inhibition of Her-2 shedding and anti-tumor activity, support that inhibition of Her-2 shedding offers a novel approach to the treatment of Her-2 overexpressing cancers. The term "selective" indicates the compounds tested were more effective inhibitors of one or more members of the ADAM family of metalloproteases than of members of the matrix metalloproteases (MMPs).

The sheddase inhibitors tested below can be prepared by any of numerous methods known in the art and are described in U.S. Ser. No. 60/534,501, the disclosure of which is incorporated herein by reference in its entirety.

Xenograft Studies

For the BT-474-SC1 tumor model (see Results below), slow-release estrogen pellets (Innovative Research of America) were inserted subcutaneously (s.c.) into the flank of each mouse 24 hours prior to tumor cell inoculation. Balb/C nude and SCID-bg mice were obtained from Charles River Laboratories. Cells were harvested from their tissue culture plates, counted, centrifuged, and resuspended in serum free growth media and BD Matrigel™ at a 1:1 ratio immediately prior to implantation. In either one or two locations, $1-2 \times 10^7$ viable BT-474-SC1 cells were injected s.c. into the upper flank of each mouse. For all models, tumors were measured on a weekly basis and their volumes calculated using the formula [volume=(length×width$^2$)÷2]. Once the mean tumor volume of the required number of mice reached the desired size (usually >150 mm$^3$), they were randomized into treatment groups usually containing between 6 and 12 mice. Animals were then treated with compound or vehicle (10% DMAC, 30% propylene glycol) by mini-osmotic pump (Alzet, Cupertino, Calif.) implanted i.p. or s.c. for 7 to 28 days to achieve the desired compound exposure—controlled by altering the pump flow rate and/or the concentration of compound inside the pumps. Tumor size and body weights (a measure of animal health) were monitored weekly. Blood samples were also drawn (retro-orbital) while the osmotic pumps were functional and plasma was separated by centrifugation and stored at −80° C. for later pharmacokinetic and/or ELISA analysis, to determine the levels of circulating Her-2 ECD (described above). Note that in experiments designed to evaluate the effects of compound treatment on levels circulating Her-2 ECD, blood samples were drawn on the day osmostic pumps were implanted (day 0) and then again six days later (day 6).

Measurement of Plasma ECD Levels

To measure levels of circulating Her-2 ECD in mice, plasmas were isolated from the blood samples described above and analyzed shortly after harvesting or stored frozen at −80° C. until analysis. To assess Her-2 ECD levels, plasma samples were diluted 1:5 and analyzed using a commercially available Her-2 ELISA kit per manufacturer's instructions (Oncogene Research, catalog #QIA10).

Immunohistochemistry and Western Blotting

For Western/immunoblot analysis, flash frozen tumor samples were pulverized and lysed in standard RIPA buffer using a dounce homogenizer and/or a polytron machine. Samples were incubated on ice for 15 minutes and centrifuged at 10,000×g for 15 min in a cold room. Supernatants were removed, protein concentrations were determined, and 20 micrograms of protein was subjected to standard immunoblotting procedures (described above). Primary antibodies used were purchased from Cell Signaling Technologies (Beverly, Mass.). Total (#9102) and phosphorylated (#9102) ERK1/2 antibodies were used at a 1:1000 dilution as were antibodies for total (#9272) and phosphorylated (#9271) Akt/PKB. For IHC, the tissues were dehydrated through a series of alcohols and 100% xylene (Poly Scientific), in a Thermo-Shandon Excelsior model processor. Subsequently, the tissues were placed in base molds (Tissue-Tek), and embedded in paraffin wax with the aid of a Histocentre2 (Thermo-Shandon, Pittsburgh, Pa.). The blocks were faced and 5 µM sections cut with a conventional microtome (e.g. Leica RM2155), floated in a warm water bath and adhered to pre-cleaned microslides (Superfrost, VWR, West Chester, Pa.). Prior to staining, slides were heated at 55-60 C for 1 hour, and then cooled to room temperature. They were deparaffinized by three passes of 5 minutes each through xylene, and rehydrated by passage through 100% and 95% ethanol (3 passes, 1 minute each, followed by 5-1 minute washes in distilled water.

Endogenous peroxidase was quenched by incubation at room temperature in 1% $H_2O_2$ for 15 minutes, followed by two washes in distilled/deionized $H_2O$ (dd$H_2O$). Antigen retrieval was achieved with pre-heated citrate buffer (Antigen Unmasking Solution, Vector Laboratories, Burlingame, Calif.) in a standard microwave unmasking protocol—10 minutes full power. Slides were cooled for 1 hour, rinsed in dd$H_2O$, and placed into phosphate-buffered saline solution (PBS) (Mediatech, Herndon, Va.). The tissue sections were encircled with a hydrophopic barrier pen (Vector Labs), and endogenous avidin and blocked (avidin and biotin) following manufacturer's protocols (Blocking Kit, Vector Labs). The slides were washed with PBS followed by the addition of 10% goat serum (Vector Labs) in PBS for 30 minutes. Antibodies were diluted into 0.5% BSA (Vector Labs)/PBS, as follows:

Rabbit anti-Ki67 (Novocastra Laboratories, Newcastle upon Tyne, UK) 1:3000

Rabbit anti-phospho-AKT:Ser473 (Cell Signaling, Beverly, Mass.) 1:200.

Antibody was added and slides incubated in a humidified chamber at 4° C. overnight. The antibody was then aspirated and the slides washed with PBS. Biotinylated secondary antibody (goat anti-rabbit, Vector Labs) was diluted 1:500 in 0.5% BSA/PBS, and added to each section for 30 minutes at room temperature. The slides were washed again with PBS and covered with an avidin-biotin-conjugated horseradish peroxidase solution (R.T.U. Vectastain Elite ABC Reagent, Vector Labs) for 30 minutes and washed a final time in PBS. Slides were developed using artificial peroxidase substrate, typically NovaRed (Vector Labs) following manufacturer's protocols. Slides were counterstained with Mayer's hematoxylin (Sigma St. Louis, Mo.) and slides were subjected to a standard dehydrating procedure and coverslipped with (Cytoseal 60, Richard Allen) and observed using a Nikon Eclipse E800. Images were captured with ACT-1 software (Nikon Corporation, Melville, N.Y.).

Results

A. Xenograft Model

In order to carry out the in vivo studies, a suitable model was identified and characterized that overexpressed Her-2 and shed significant levels of Her-2 ECD. Additionally, while Her-2 may be upregulated in a variety of cancer cell lines by multiple mechanisms, a cell line was chosen in which Her-2 overexpression results from genomic amplification of the gene encoding Her-2 because it is believed that this type of genetic mutation more strongly supports a role for Her-2 in the transformed phenotype of the cell type. While the literature describes a number of cell lines possessing this 'shedding' phenotype, the BT-474 model was chosen based on its ability to form tumors in immune compromised mice (van Slooten, H. J., et al., 1995, British J Cancer 72:22-30).

A subclone of BT-474, herein referred to as BT474-SC1, that had both improved tumor take and increased growth kinetics was derived according to routine methods. Using plasma obtained from mouse bearing BT474-SC1 tumors, it was established that this subclone sheds Her-2 similar to the parental cell line. This cell line was used for the experiments described below.

B. Inhibition of Her-2 Shedding In Vivo

Figure 27:
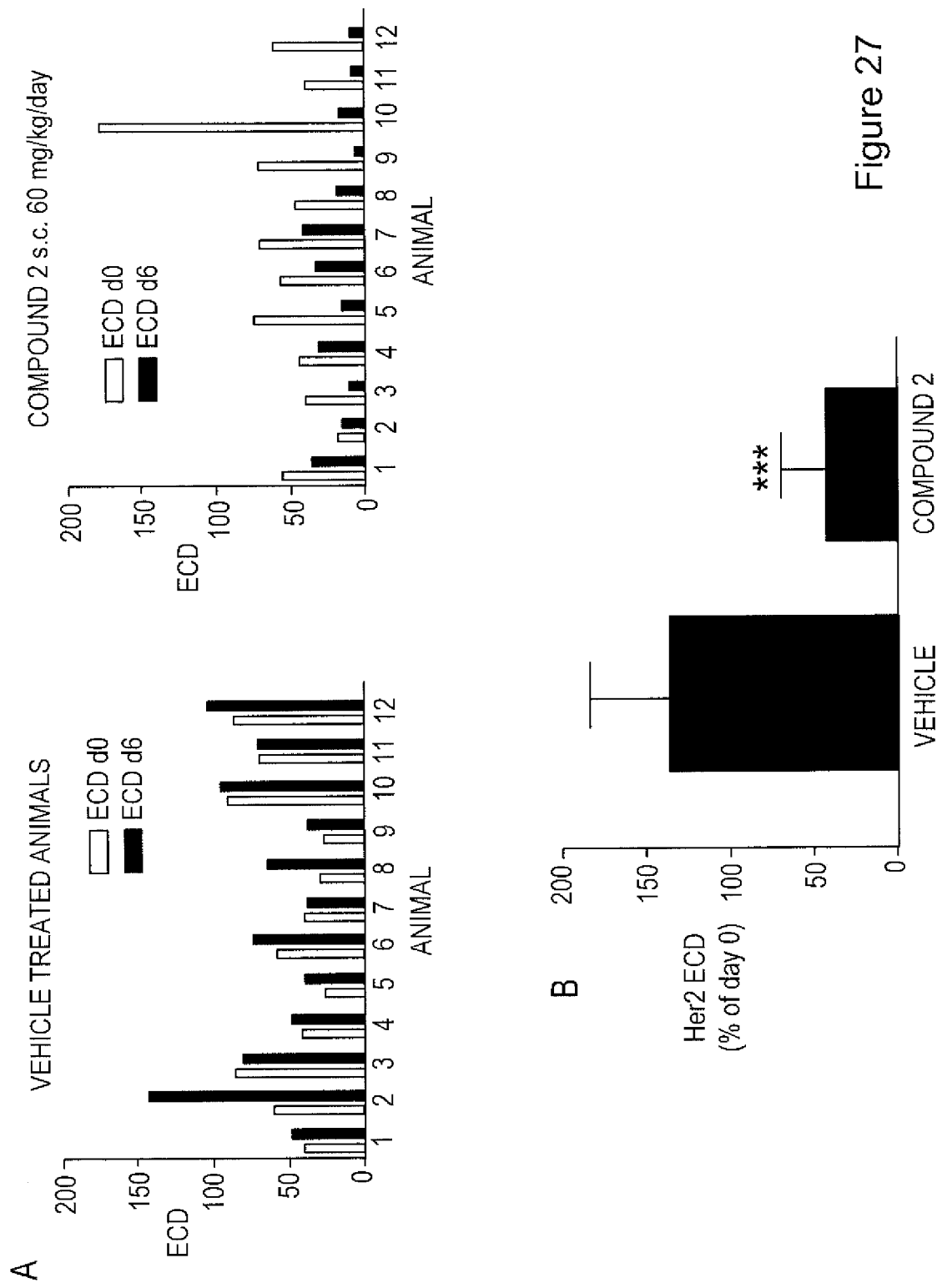
FIG. 27A presents graphical data showing that Compound 2 effectively reduces Her-2 shedding in BT-474-SC1 tumor bearing mice.
FIG. 27B provides a statistical comparison of vehicle and Compound 2 treated BT-474-SC1 tumor bearing mice groups showing that Compound 2 reduced levels of Her-2 ECD.

The ability of Her-2 shedding inhibitors, Compound 1 and Compound 2, was first tested to reduce the circulating levels of Her-2 ECD in the plasma of mice bearing BT-474-SC1 human breast cancer tumor xenografts. Immune compromised mice were injected with BT-474-SC1 cells mixed with Matrigel™ subcutaneously into the upper flanks of the mice. From previous experiments, it was determined that when the tumor burden exceeded roughly 200 mm$^3$, the levels of circulating Her-2 ECD were detectable (in plasma samples using the ELISA assay referred to previously) and significant enough that a window for potential quantifiable inhibition existed (data not shown). As such, tumors were measured weekly and when the desired number of mice had tumors of the required size, they were randomly assigned into one of two treatment groups, vehicle or compound. All mice were then bled prior to the implantation of the miniature osmotic pumps to determine a baseline level of circulating ECD (day 0). Six days after the treatment was initiated (day 6), the mice were euthanized and tissues of interest were collected, including blood and tumors. Plasma samples from days 0 and 6 were analyzed by ELISA to determine the levels of Her-2 ECD (FIG. 27). Using this method, each mouse was able to serve as its own control. The majority of animals treated with vehicle showed a modest increase in their shed ECD levels over the six day timeframe; however, mice treated with a selective sheddase inhibitor (Compound 2) had a significantly lower level of circulating ECD on day 6 compared to vehicle treated animals (p<0.0001), as well as on an individual basis (comparing days 0 and 6).

C. Inhibition Tumor Growth

Figure 28:
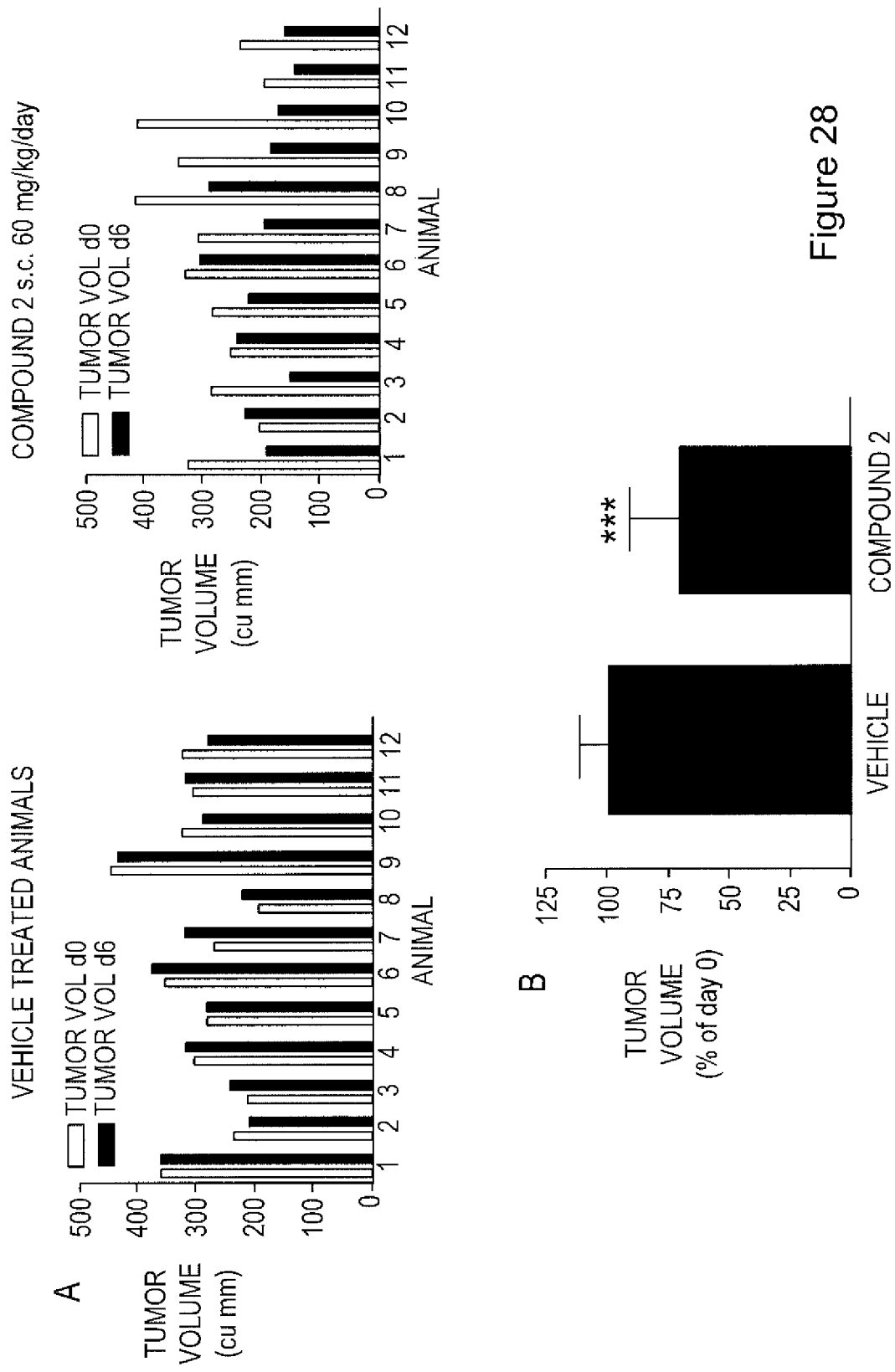
FIG. 28A presents graphical data showing that Compound 2 effectively reduces tumor volume in BT-474-SC1 tumor bearing mice.
FIG. 28B provides a statistical comparison of vehicle and Compound 2 treated BT-474-SC1 tumor bearing mice groups showing that Compound 2 reduced tumor volume.

To determine the effect of the inhibition of Her-2 shedding on tumor growth, we evaluated the effect of Compound 2 treatment on tumor size in the BT474-SC1 xenograft model. As shown in FIG. 28, Compound 2 treated tumors were significantly smaller on day 6 than vehicle tumors (p=0.0001) and, multiple tumors demonstrated a partial remission (greater than a 25% reduction in tumor volume). A comparison of the magnitude of change in ECD (56%) and tumor volume (27%) indicated that the decreased ECD levels were not a reflection of decreased tumor volume.

Figure 29:
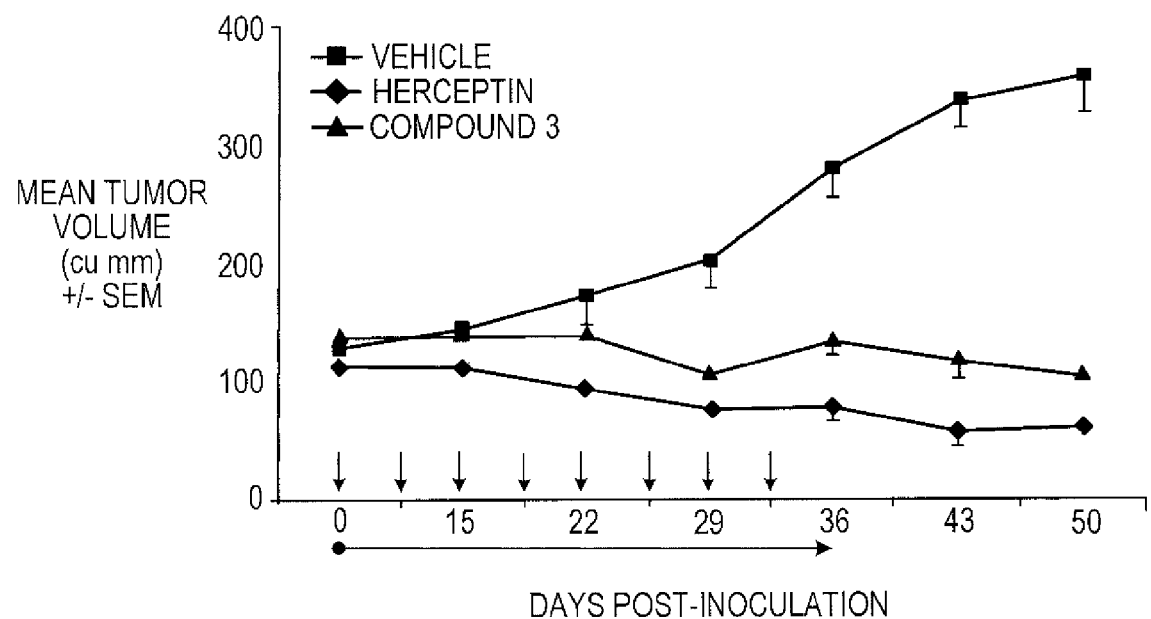
FIG. 29 shows reduction of tumor volume in BT-474-SC1 tumor bearing mice for Herceptin and Compound 3 compared with vehicle control.

The in vivo studies described above demonstrate the ability of sheddase including selective sheddase inhibition, to reduce the shedding of Her-2 from tumor cells and impact tumor burden in an acute manner. In order to characterize the therapeutic efficacy of selective sheddase inhibitors, experiments were performed in the same model system exposing the mice to prolonged treatment. In one such experiment, another selective sheddase inhibitor, Compound 3 ((6S,7S)-6-{[4-phenyl-3,6-dihydropyridin-1(2H)-yl]carbonyl}-N-hydroxy-5-azaspiro[2.5]octane-7-carboxamide), was evaluated in the same BT474-SC1 model over a 28-day period. While the tumors in vehicle treated mice tripled in size of the experimental period, a complete suppression of tumor growth was noted in the mice treated with Compound 3 (FIG. 29). For comparison, another group of mice were treated with Trastuzumab/Herceptin™, a humanized antibody that binds Her-2 directly. Note that both treatments produced similar changes to the growth kinetics of the BT-474-SC1 tumors and the lack of overlap in the growth curve merely reflects a larger mean tumor volume for the Compound 3 treated animals at the initiation of the experiments. Taken together, the data indicate that administration of sheddase inhibitors, including selective sheddase inhibitors, decreases circulating levels of shed Her-2 ECD, acutely reduces tumor burden, and effectively prevents tumor growth during, and even (e.g., at least two weeks) after administration ceased.

D. Inhibition of Her-2 Signaling Pathways

Figure 30:
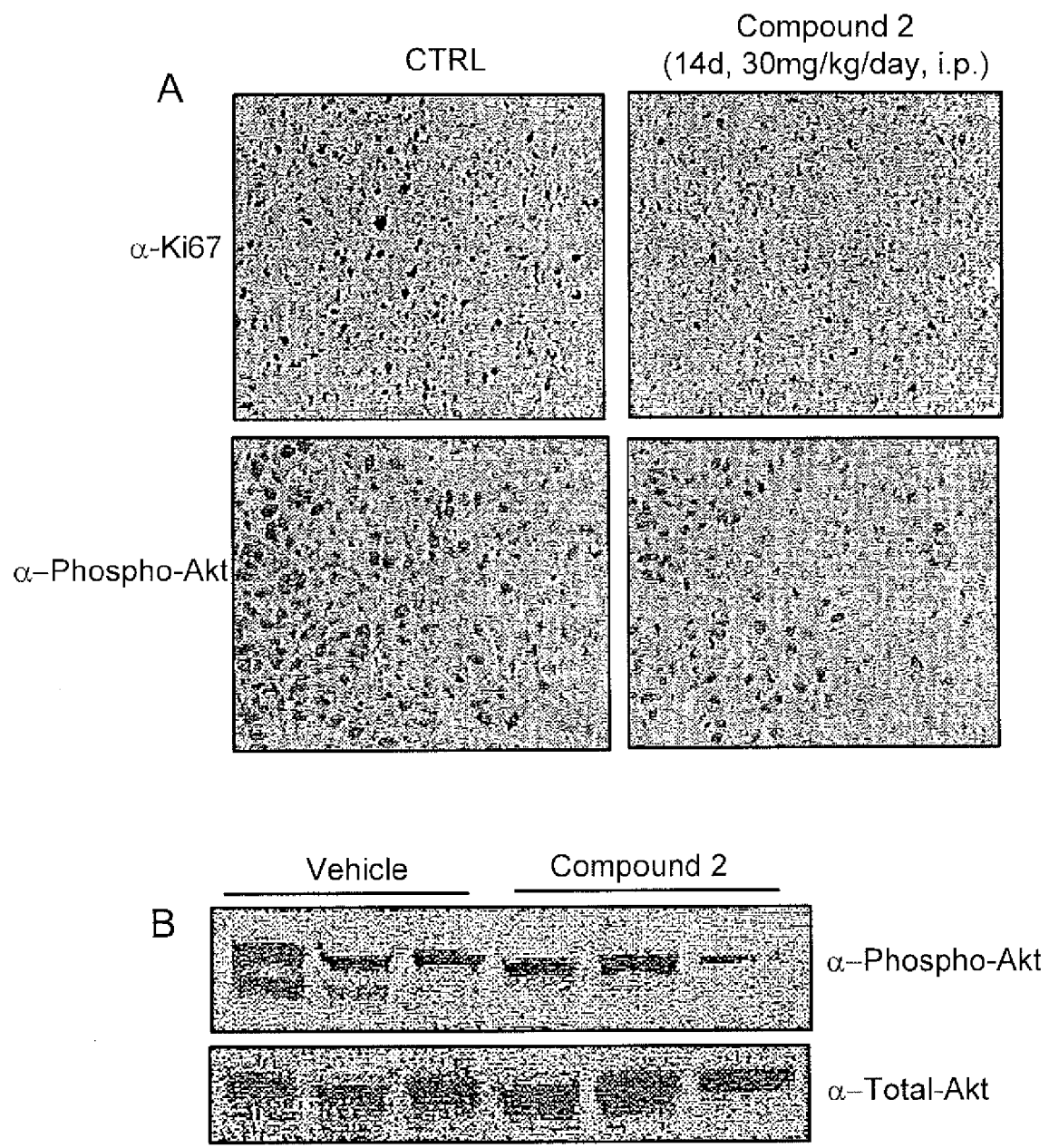
FIG. 30A shows tumor tissue stained with antibodies for Ki67 (upper) or phosphorylated Akt (lower), marker for cellular proliferation.
FIG. 30B shows immunoblots of for equal amounts of phosphorylated Akt or total Akt in tumor tissue samples treated with either vehicle or Compound 2.

Tumors removed from Compound 2 and vehicle treated groups were subjected to immunohistochemical and western blotting analysis. Her-2 signaling normally leads to the activation of pathways that control cellular proliferation and survival. To first determine if sheddase inhibitors were able to impact the proliferative index of human breast cancer xenografts, mice bearing BT-474-SC1 tumors were treated with selective sheddase inhibitors for 14 days at which time they were sacrificed and their tumors removed and divided into portions for freezing and fixation (for paraffin embedding and immunohistochemistry). Paraffin embedded tumor sections were mounted on slides and used for immunohistochemistry (IHC) to stain for Ki-67, a marker of active cell cycling (FIG. 30A, upper panel). Tumors treated with sheddase inhibitors had significantly fewer cells staining positive for Ki-67 indicating decreased cellular proliferation.

Furthermore, signaling from Her-2, has been shown to activate the Akt/PKB pathway, it is believed indirectly, through the phosphorylation of specific residues. Activation of this pathway has been shown to affect tumor cell survival and proliferation pathways (see, e.g., Datta, S. R., et al., 1999, Genes and Development 13:2905-2927) and cells expressing high levels of Her-2 appear to be sensitive to perturbations in this pathway (Hermanto, U., et al., 2001, Oncogene, 20:7551-7562). Thus, it is believed that inhibiting Akt activity will potentially decrease tumor cell proliferation while at the same time increasing the sensitivity of cells to stresses that induce apoptosis (e.g. cancer chemotherapeuctics).

To analyze the effects of sheddase inhibition on Akt activity, IHC specific for phosphorylated Akt was performed on control or treated tumor samples (described above) (FIG. 30A, lower panel). In addition, to examine the effects of sheddase inhibition on Akt phosphorylation in the whole tumor, the levels of total and phospho-Akt were also examined by immunoblot analysis using specific antibodies (FIG. 30B). Both IHC and immunoblotting indicated that treatment with selective shedding inhibitors decreases the amount of phosphorylated Akt in tumors.

Summary

In summary, treatment of mice bearing BT-474-SC1 tumor xenografts, a model of human breast cancer with high expression of Her-2, with sheddase inhibitors decreased the levels of Her-2 ECD shedding in circulation. Such inhibition of Her-2 shedding is shown to be associated with tumor growth inhibition. Molecular effects of shedding inhibition included decreases in the proliferative index treated tumors, as assessed by Ki67 staining, and decreases in survival pathway signaling in tumor cells, as was exemplified by decreased levels of phosphorylated Akt. This latter effect allows these molecules to be synergistic with other therapeutic treatments when administered in conjunction.

The above results indicate that selective sheddase inhibitors decrease circulating Her-2 ECD levels in an animal model of human breast cancer. This decrease is associated with suppression of survival and cell cycle signaling and a tumor growth inhibitory effect.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating breast cancer in a patient, wherein said cancer overexpresses Her-2, comprising inhibiting the proliferation of cancer cells that overexpress Her-2 in the patient by:
  administering to said patient a therapeutically effective amount of a metalloprotease inhibitor that is an ADAM10 inhibitor that inhibits Her-2 cleavage; and
  administering to the patient a therapeutically effective amount of an anti-Her-2 antibody.

2. The method of claim 1, wherein said metalloprotease inhibitor is a hydroxamate compound.

3. The method of claim 1 wherein said metalloprotease inhibitor is selective for ADAM10.

4. The method of claim 1 wherein said ADAM10 inhibitor inhibits cleavage of Her-2 in vivo.

5. The method of claim 1 wherein said antibody is administered simultaneously with said ADAM10 inhibitor.

6. The method of claim 1 further comprising administering to said patient a cytotoxin.

7. The method of claim 1 further comprising administering to said patient an EGFR tyrosine kinase inhibitor.

8. The method of claim 6, wherein said cytotoxin is selected from the group consisting of paclitaxel, docetaxel, 7-O-methylthiomethyl-paclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, [1S-[1R*,3R*(E),7R*,10S *,11R*,12R*,16S *]]-3-[2-[2-(aminomethyl)-4-thiazoly 1]-1-methylethenyl]-7,11-dihydroxy-8,8,10,12,16-pentamethyl-4,17-dioxabicyc lo[14.1.0]heptadecane-5,9-dione, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, vindesine, leurosine, estramustine, cisplatin, carboplatin, cyclophosphamide, bleomycin, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, a pyridobenzoindole, an interferon and an interleukin.

9. The method of claim 6 wherein said antibody is trastuzumab.

10. The method of claim 6, wherein said cytotoxin is selected from the group consisting of paclitaxel and cisplatin.

11. The method of claim 7 wherein said kinase inhibitor is gefitinib.

12. A method of treating breast cancer in a patient, wherein said cancer overexpresses Her-2, comprising:
  detecting that the cancer overexpresses Her-2; and
  inhibiting the proliferation of cancer cells that overexpress Her-2 in the patient by:
  administering to the patient a therapeutically effective amount of a metalloprotease inhibitor that is an ADAM10 inhibitor that inhibits Her-2 cleavage; and
  administering to the patient a therapeutically effective amount of an anti-Her-2 antibody.

13. The method of claim 12, wherein said ADAM10 inhibitor is methyl (6S,7S)-7-[(hydroxyamino)carbonyl]-6-[(4-phenylpiperazin-1-yl)carbonyl]-5-azaspiro[2.5]octane-5-carboxylate.

14. The method of claim 12, wherein said anti-Her-2 antibody is trastuzumab.

15. The method of claim 13, wherein said anti-Her-2 antibody is trastuzumab.

* * * * *